United States Patent
Blaber et al.

(10) Patent No.: US 10,022,426 B2
(45) Date of Patent: *Jul. 17, 2018

(54) FIBROBLAST GROWTH FACTOR MUTANTS HAVING IMPROVED FUNCTIONAL HALF-LIFE AND METHODS OF THEIR USE

(71) Applicant: Florida State University Research Foundation, Inc., Tallahassee, FL (US)

(72) Inventors: Michael Blaber, Tallahassee, FL (US); Jihun Lee, Rockville, MD (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/295,774

(22) Filed: Oct. 17, 2016

(65) Prior Publication Data

US 2017/0095532 A1    Apr. 6, 2017

Related U.S. Application Data

(60) Division of application No. 14/593,107, filed on Jan. 9, 2015, now Pat. No. 9,469,680, which is a division of application No. 13/669,856, filed on Nov. 6, 2012, now Pat. No. 8,962,557, which is a continuation-in-part of application No. 12/783,005, filed on May 19, 2010, now Pat. No. 8,461,111.

(60) Provisional application No. 61/309,590, filed on Mar. 2, 2010, provisional application No. 61/179,751, filed on May 20, 2009.

(51) Int. Cl.
*A61K 38/18*    (2006.01)
*C07K 14/50*    (2006.01)

(52) U.S. Cl.
CPC .......... *A61K 38/1825* (2013.01); *C07K 14/50* (2013.01); *C07K 14/501* (2013.01)

(58) Field of Classification Search
None
See application file for complete search history.

(56) References Cited

U.S. PATENT DOCUMENTS

| 8,461,111 B2* | 6/2013 | Blaber | A61K 38/18 |
| | | | 514/9.1 |
| 8,962,557 B2* | 2/2015 | Blaber | A61K 38/18 |
| | | | 514/9.1 |
| 9,469,680 B2* | 10/2016 | Blaber | A61K 38/18 |

* cited by examiner

*Primary Examiner* — Marianne P Allen
(74) *Attorney, Agent, or Firm* — Christopher M. Ramsey; GrayRobinson, P.A.

(57) ABSTRACT

Mutant fibroblast growth factor (FGF) proteins having a polypeptide sequence with a high sequence identity to proteins encoded by members of the Fgf-1 subfamily of genes from a mammalian species, such as human, and with a specific amino acid substitution of an alanine at a position corresponding to amino acid position 66 of human FGF-1 with a cysteine and/or a specific amino acid substitution of a phenylalanine at a position corresponding to amino acid position 132 of human FGF-1 with a tryptophan (based on the 140 amino acid numbering scheme of human FGF-1) are provided. Other amino acid mutations or substitutions may be combined. Polynucleotide sequences encoding the mutant FGF proteins and host cells containing such polynucleotide sequences are provided. Methods of administering a mutant FGF protein to an individual to treat an ischemic condition or disease or a wound or tissue injury are also provided.

4 Claims, 27 Drawing Sheets

```
1                  10                  20                  30
MAEGEITTFTALTEK F N L P P G N Y K K P K L L Y
                   40                  50                  60
C S N G G H F L R I L P D G T V D G T R D R S D Q H I Q L Q
                   70                  80                  90
L S A E S V G E V Y I K S T E T G Q Y L A M D T D G L L Y G
                  100                 110                 120
S Q T P N E E C L F L E R L E E N H Y N T Y I S K K H A E K
                  130                 140                 150
N W F V G L K K N G S C K R G P R T H Y G Q K A I L F L P L
    155
P V S S D
```

| Protein | ΔG (kJ/mol) | m-value (kJ/mol) | $C_m$ (M) | ΔΔG[a] (kJ/mol) |
|---|---|---|---|---|
| Wild Type | 26.6 ± 0.9 | 20.3 ± 0.7 | 1.29 ± 0.01 | – |
| K12V/C117V | 33.9 ± 0.4 | 20.0 ± 0.2 | 1.69 ± 0.01 | −8.1 |
| C83A | 20.8 ± 0.7 | 20.5 ± 0.3 | 1.01 ± 0.02 | 5.7 |
| C83S | 20.0 ± 0.8 | 20.9 ± 0.7 | 0.96 ± 0.01 | 6.9 |
| C83T | 20.5 ± 0.9 | 19.8 ± 0.6 | 1.03 ± 0.02 | 5.2 |
| C83V | 14.7 ± 0.5 | 20.9 ± 0.7 | 0.70 ± 0.01 | 12.1 |
| C83I/K12V/C117V | 20.9 ± 0.4 | 19.7 ± 0.4 | 1.06 ± 0.02 | 12.6[b] |
| A66C (reduced)[c] | 16.4 ± 0.2 | 16.3 ± 0.1 | 1.01 ± 0.01 | 5.1 |
| A66C (oxidized)[d] | 28.7 ± 1.9 | 15.4 ± 1.0 | 1.87 ± 0.01 | −10.4 (−13.6[e]) |

[a] ΔΔG = $(C_{mWT} - C_{m\ mutant})(m_{mWT} + m_{mutant})/2$ as described by Pace and Scholtz. A negative value of ΔΔG indicates a more stable mutation, and error is stated as the standard error from multiple data sets.
[b] ΔΔG value calculated with respect to background mutant, Lys12→Val/Cys117→Val
[c] Determined in crystal buffer containing 10mM DTT.
[d] Determined from a global fit of the oxidized component of the 12-168 hr air-oxidized samples in buffer without DTT.
[e] ΔΔG of the oxidized form of A66C in reference to the reduced form of A66C.

FIG.6

| | Cys83→Ala | Cys83→Ser | Cys83→Thr | Cys83→Val | Lys12→Val/ Cys83→Ile/ Cys117→Val | Ala66→Cys (reduced) | Ala66→Cys (oxidized) |
|---|---|---|---|---|---|---|---|
| Space Group | C222₁ | C222₁ | C222₁ | C222₁ | P2₁ | P2₁ | C222₁ |
| Cell constants | a=74.4 b=95.4 c=108.9 | a=75.4 b=94.4 c=108.7 | a=74.2 b=95.9 c=109.1 | a=74.7 b=97.4 c=108.2 | a=50.8 b=108.1 c=67.7 β=103.7 | a=51.4 b=110.8 c=67.3 β=105.3 | a=74.0 b=96.9 c=108.9 |
| Max Resolution (Å) | 1.90 | 2.10 | 1.90 | 1.90 | 2.55 | 2.15 | 2.30 |
| Mosaicity (°) | 1.1 | 0.5 | 1.0 | 0.6 | 1.3 | 1.2 | 1.4 |
| Redundancy | 10.2 | 10.1 | 11.7 | 12.8 | 3.6 | 3.4 | 6.8 |
| Mol/ASU | 2 | 2 | 2 | 2 | 4 | 4 | 2 |
| Matthew coeff. (Å/Da) | 2.93 | 2.93 | 2.94 | 2.98 | 2.73 | 2.80 | 2.96 |
| Total reflections | 311,775 | 231,997 | 354,786 | 396,203 | 79,101 | 133,744 | 103,847 |
| Unique reflections | 30,504 | 22,991 | 30,327 | 31,013 | 21,754 | 39,339 | 15,240 |
| I/σ | 30.6 (3.0) | 37.1 (6.8) | 48.3 (7.5) | 58.5 (6.0) | 6.0 (3.0) | 18.0 (3.1) | 24.8 (3.3) |
| Completion (%) | 98.2 (85.2) | 100 (100) | 97.4 (90.9) | 98.5 (84.8) | 94.8 (93.1) | 99.7 (100) | 85.7 (84.4) |

FIG. 7-1

| | | | | | | | |
|---|---|---|---|---|---|---|---|
| R-merge (%) | 7.7 (30.1) | 7.7 (24.8) | 6.7 (29.2) | 5.7 (31.1) | 9.5 (25.6) | 9.6 (38.0) | 8.6 (38.3) |
| Nonhydrogen protein atoms | 2,270 | 2,272 | 2,284 | 2,274 | 4,538 | 4,558 | 2,274 |
| Solvent molecules/ion | 268/19 | 159/17 | 312/9 | 277/23 | 106/10 | 178/16 | 96/11 |
| $R_{cryst}$ (%)/$R_{free}$ (%) | 17.8/21.8 | 19.8/23.5 | 18.6/22.4 | 18.9/23.3 | 21.2/26.3 | 22.5/26.7 | 19.8/23.4 |
| R.M.S.D. bond length (Å) | 0.01 | 0.01 | 0.01 | 0.01 | 0.01 | 0.01 | 0.01 |
| R.M.S.D. bond angle (°) | 1.5 | 1.4 | 1.5 | 1.5 | 1.3 | 1.5 | 1.3 |
| Ramachandran plot: | | | | | | | |
| most favored (%) | 92.1 | 92.1 | 92.5 | 91.2 | 84.6 | 90.1 | 89.0 |
| additional allowed (%) | 7.9 | 7.5 | 6.6 | 7.5 | 15.1 | 8.8 | 11.0 |
| generously allowed (%) | 0.0 | 0.4 | 0.9 | 1.3 | 0.2 | 1.1 | 0.0 |
| disallowed region (%) | 0.0 | 0.0 | 0.0 | 0.0 | 0.0 | 0.0 | 0.0 |
| PDB accession | 3FJH | 3FJE | 3FJF | 3FJJ | 3FJI | 3FJK | 3HOM |

FIG. 7-2

| | L44W | F85W | F132W | V31I | C117I | L44F/ F132W | C83T/C117V/ L44F/F132W |
|---|---|---|---|---|---|---|---|
| Space Group | C222$_1$ | C222$_1$ | C222$_1$ | C222$_1$ | C222$_1$ | C222$_1$ | C222$_1$ |
| Cell constants (Å) | a=73.8 b=97.6 c=108.8 | a=74.2 b=95.8 c=109.6 | a=74.4 b=96.0 c=108.9 | a=73.9 b=97.4 c=108.8 | a=74.7 b=97.2 c=108.1 | a=73.2 b=97.6 c=108.5 | a=74.4 b=96.0 c=108.4 |
| Max Resolution (Å) | 2.0 | 1.9 | 1.95 | 2.0 | 2.0 | 1.9 | 1.95 |
| Mosaicity (°) | 0.53 | 1.00 | 0.96 | 0.44 | 0.50 | 0.60 | 0.68 |
| Redundancy | 6.5 | 7.0 | 5.8 | 5.6 | 9.0 | 12.9 | 13.2 |
| Mol/ASU | 2 | 2 | 2 | 2 | 4 | 4 | 2 |
| Matthew coeff. (Å$^3$/Da) | 2.97 | 2.95 | 2.95 | 2.97 | 2.98 | 2.94 | 2.93 |
| Total reflections | 169,561 | 214,161 | 164,516 | 146,083 | 242,167 | 398,874 | 368,957 |
| Unique reflections | 25,975 | 30,761 | 28,568 | 26,232 | 26,839 | 30,802 | 27,994 |
| I/σ (overall) | 42.4 | 32.2 | 30.2 | 32.0 | 30.4 | 35.7 | 56.2 |
| I/σ (highest shell) | 7.3 | 3.6 | 3.6 | 3.7 | 3.3 | 3.8 | 8.6 |
| Completion overall (%) | 96.2 | 98.7 | 99.1 | 97.2 | 99.4 | 99.3 | 97.3 |
| Completion highest shell (%) | 70.7 | 89.2 | 99.1 | 95.6 | 94.5 | 91.9 | 78.6 |
| R-merge overall (%) | 6.2 | 7.9 | 6.2 | 7.8 | 9.1 | 7.3 | 5.6 |
| R-merge highest shell (%) | 18.3 | 37.9 | 31.0 | 28.8 | 38.7 | 35 | 19.4 |

FIG.13-1

| | | | | | | | |
|---|---|---|---|---|---|---|---|
| Nonhydrogen protein atoms | 2,284 | 2,278 | 2,278 | 2,254 | 2,276 | 2,284 | 2,288 |
| Solvent molecules/ion | 174/17 | 238/15 | 235/12 | 186/10 | 187/15 | 199/14 | 224/14 |
| $R_{cryst}$ (%) | 20.7 | 18.8 | 19.0 | 19.9 | 19.8 | 19.0 | 20.6 |
| $R_{free}$ (%) | 24.3 | 22.8 | 21.3 | 23.3 | 23.1 | 22.1 | 23.8 |
| R.M.S.D. bond length (Å) | 0.009 | 0.009 | 0.008 | 0.010 | 0.009 | 0.009 | 0.006 |
| R.M.S.D. bond angle (°) | 1.4 | 1.5 | 1.4 | 1.5 | 1.5 | 1.4 | 1.3 |
| Ramachandran plot: | | | | | | | |
| most favored (%) | 90.4 | 92.5 | 93.4 | 89.5 | 89.5 | 92.5 | 90.4 |
| additional allowed (%) | 9.2 | 7.5 | 6.6 | 9.6 | 10.1 | 7.0 | 9.6 |
| generously allowed (%) | 0.4 | 0.0 | 0.0 | 0.9 | 0.4 | 0.4 | 0.0 |
| disallowed region (%) | 0.0 | 0.0 | 0.0 | 0.0 | 0.0 | 0.0 | 0.0 |
| PDB accession | 3FJC | 3FJ9 | 3FJA | 3FJB | 3FJ8 | 3FJD | 3FGM |

FIG.13-2

| Protein | ΔG (kJ/mol) | M-value (kJ/mol M) | $C_m$ (M) | ΔΔG[a] (kj/mol) |
|---|---|---|---|---|
| Reference proteins | | | | |
| Wild-type[b] | 21.1 ± 0.6 | 18.9 ± 0.6 | 1.11 ± 0.01 | – |
| C117V[b] | 21.0 ± 0.3 | 20.1 ± 0.1 | 1.05 ± 0.01 | 1.2 |
| K12V/C117V[c] | 27.7 ± 0.5 | 18.1 ± 0.3 | 1.53 ± 0.01 | –7.8 |
| Cavity filling core mutations | | | | |
| L44W | 1.51 ± 0.9 | 16.5 ± 0.7 | 0.92 ± 0.02 | 3.4 |
| F85W | 22.3 ± 0.1 | 19.7 ± 0.3 | 1.13 ± 0.01 | –0.4 |
| F132W | 26.1 ± 0.4 | 22.0 ± 0.5 | 1.19 ± 0.01 | –1.6 |
| V31I | 18.8 ± 0.1 | 20.7 ± 0.1 | 0.91 ± 0.00 | 4.0 |
| C117I | 20.1 ± 0.5 | 19.6 ± 0.3 | 1.03 ± 0.01 | 1.5 |
| L44F[b] | 25.1 ± 0.3 | 20.4 ± 0.2 | 1.23 ± 0.01 | –2.4 |
| L44F/F132W | 24.0 ± 1.0 | 18.1 ± 0.8 | 1.32 ± 0.01 | –3.9 |
| Buried free-cysteine removal mutations | | | | |
| C83T/C117V | 17.5 ± 0.8 | 21.7 ± 0.9 | 0.81 ± 0.01 | 6.1 |
| C83T/C117V/L44F/F132W | 21.4 ± 0.8 | 18.9 ± 0.6 | 1.13 ± 0.01 | –0.4 |
| C83T/C117V/K12V | 24.1 ± 0.5 | 19.9 ± 0.4 | 1.21 ± 0.01 | –1.9 |

[a] ΔΔG = ($C_{m\ wild-type}$ – $C_{m\ mutant}$)($m_{wild-type}$ + $m_{mutant}$)/2 as described by Pace and Scholtz cited in the text. A negative value of ΔΔG indicates a more stable mutation.
[b] Thermodynamic parameters reported by Brych et al. (2003) cited in the text.
[c] Thermodynamic parameters reported by Dubey et al. (2007) cited in the text.

FIG. 14

| Protein | ΔG (kJ/mol) | M-value (kJ/mol) | $T_m$ (K) | $\Delta T_m$ (K) | $\Delta \Delta G^a$ (kJ/mol) |
|---|---|---|---|---|---|
| Wild Type | 275 ± 2 | 0.88 | 312.9 ± 0.1 | – | – |
| L44F | 327 ± 2 | 1.03 | 316.0 ± 0.1 | 3.1 | -3.0 |
| F85W | 266 ± 4 | 0.85 | 312.6 ± 0.4 | -0.3 | 0.3 |
| F132W | 289 ± 2 | 0.92 | 314.1 ± 0.1 | 1.3 | -1.2 |
| L44F/F132W | 330 ± 4 | 1.04 | 317.0 ± 0.1 | 4.2 | -4.1 |

FIG.15

| Protein | $EC_{50}$ (ng/ml) | | Unconditioned medium half-life (hr) | 200:1 trypsin digestion half-life (min) |
|---|---|---|---|---|
| | (–) Heparin | (+) Heparin | | |
| Wild-type | 58.4 ± 25.4 | 0.48 ± 0.08 | 1.0 | 9.8 |
| C117V | 18.0 ± 12.9 | 0.61 ± 0.12 | 9.4 | 9.1 |
| C83T/C117V | 0.98 ± 0.78 | 0.35 ± 0.25 | 14.9 | 6.4 |
| C83T/C117V/L44F/F132W | 0.74 ± 0.19 | 0.51 ± 0.15 | 42.6 | 12.4 |
| C83T/C117V/K12V | 0.93 ± 0.25 | 0.36 ± 0.12 | 40.4 | 19.1 |

FIG.16

| Protein | $EC_{50}$ (ng/ml) | | Unconditioned medium half-life (hr) |
|---|---|---|---|
| | (–) Heparin | (+) Heparin | |
| Wild-type FGF-1 | 58.4 ± 25.4 | 0.48 ± 0.08 | 1.0 |
| A66C | 5.43 ± 3.96 | 0.36 ± 0.20 | 14.2 |

SEQUENCE LISTING

<160> NUMBER OF SEQ ID NOS: 19

<210> SEQ ID NO 1
<211> LENGTH: 140
<212> TYPE: PRT
<213> ORGANISM: Homo sapiens

<400> SEQUENCE: 1

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 2
<211> LENGTH: 155
<212> TYPE: PRT
<213> ORGANISM: Homo sapiens

<400> SEQUENCE: 2

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 3
<211> LENGTH: 154
<212> TYPE: PRT

<213> ORGANISM: Homo sapiens

<400> SEQUENCE: 3

```
Ala Glu Gly Glu Ile Thr Thr Phe Thr Ala Leu Thr Glu Lys Phe Asn
1               5                   10                  15
Leu Pro Pro Gly Asn Tyr Lys Lys Pro Lys Leu Leu Tyr Cys Ser Asn
            20                  25                  30
Gly Gly His Phe Leu Arg Ile Leu Pro Asp Gly Thr Val Asp Gly Thr
        35                  40                  45
Arg Asp Arg Ser Asp Gln His Ile Gln Leu Gln Leu Ser Ala Glu Ser
    50                  55                  60
Val Gly Glu Val Tyr Ile Lys Ser Thr Glu Thr Gly Gln Tyr Leu Ala
65                  70                  75                  80
Met Asp Thr Asp Gly Leu Leu Tyr Gly Ser Gln Thr Pro Asn Glu Glu
                85                  90                  95
Cys Leu Phe Leu Glu Arg Leu Glu Glu Asn His Tyr Asn Thr Tyr Ile
            100                 105                 110
Ser Lys Lys His Ala Glu Lys Asn Trp Phe Val Gly Leu Lys Lys Asn
        115                 120                 125
Gly Ser Cys Lys Arg Gly Pro Arg Thr His Tyr Gly Gln Lys Ala Ile
    130                 135                 140
Leu Phe Leu Pro Leu Pro Val Ser Ser Asp
145                 150
```

<210> SEQ ID NO 4
<211> LENGTH: 155
<212> TYPE: PRT
<213> ORGANISM: Homo sapiens

<400> SEQUENCE: 4

```
Met Ala Ala Gly Ser Ile Thr Thr Leu Pro Ala Leu Pro Glu Asp Gly
1               5                   10                  15
Gly Ser Gly Ala Phe Pro Pro Gly His Phe Lys Asp Pro Lys Arg Leu
            20                  25                  30
Tyr Cys Lys Asn Gly Gly Phe Phe Leu Arg Ile His Pro Asp Gly Arg
        35                  40                  45
Val Asp Gly Val Arg Glu Lys Ser Asp Pro His Ile Lys Leu Gln Leu
    50                  55                  60
Gln Ala Glu Glu Arg Gly Val Val Ser Ile Lys Gly Val Cys Ala Asn
65                  70                  75                  80
Arg Tyr Leu Ala Met Lys Glu Asp Gly Arg Leu Leu Ala Ser Lys Cys
                85                  90                  95
Val Thr Asp Glu Cys Phe Phe Phe Glu Arg Leu Glu Ser Asn Asn Tyr
            100                 105                 110
Asn Thr Tyr Arg Ser Arg Lys Tyr Thr Ser Trp Tyr Val Ala Leu Lys
        115                 120                 125
Arg Thr Gly Gln Tyr Lys Leu Gly Ser Lys Thr Gly Pro Gly Gln Lys
    130                 135                 140
Ala Ile Leu Phe Leu Pro Met Ser Ala Lys Ser
145                 150                 155
```

<210> SEQ ID NO 5
<211> LENGTH: 140
<212> TYPE: PRT
<213> ORGANISM: Artificial Sequence
<220> FEATURE:
<223> OTHER INFORMATION: Description of Artificial Sequence: Synthetic

```
                        polypeptide
<220> FEATURE:
<223> OTHER INFORMATION: Mutant FGF-1 protein

<400> SEQUENCE: 5

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 6
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant FGF-2 protein

<400> SEQUENCE: 6

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Cys Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 7
<211> LENGTH: 140
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant FGF-1 protein

<400> SEQUENCE: 7

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Trp Leu Pro Leu Pro Val Ser Ser Asp
    130                 135                 140

<210> SEQ ID NO 8
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant FGF-2 protein

<400> SEQUENCE: 8

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Trp Leu Pro Met Ser Ala Lys Ser
145                 150                 155
```

<210> SEQ ID NO 9
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant FGF-1 protein

<400> SEQUENCE: 9

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Trp Leu Pro Leu Pro Val Ser Ser Asp
    130                 135                 140
```

<210> SEQ ID NO 10
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant FGF-2 protein

<400> SEQUENCE: 10

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Cys Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
```

```
                130                 135                 140
Ala Ile Leu Trp Leu Pro Met Ser Ala Lys Ser
145                 150                 155

<210> SEQ ID NO 11
<211> LENGTH: 155
<212> TYPE: PRT
<213> ORGANISM: Mus musculus

<400> SEQUENCE: 11

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 12
<211> LENGTH: 154
<212> TYPE: PRT
<213> ORGANISM: Mus musculus

<400> SEQUENCE: 12

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150
```

<210> SEQ ID NO 13
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Thr Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Trp Leu Pro Leu Pro Val Ser Ser Asp
    130                 135                 140

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Glu Glu Ala
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Asn Glu Glu Ser
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Glu Glu Thr
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Glu Glu Val
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Glu Glu Ile
1
```

FIBROBLAST GROWTH FACTOR MUTANTS HAVING IMPROVED FUNCTIONAL HALF-LIFE AND METHODS OF THEIR USE

CROSS-REFERENCE TO RELATED APPLICATIONS

This is a divisional application of U.S. patent application Ser. No. 14/593,107, filed Jan. 9, 2015, which is a divisional application of U.S. patent application Ser. No. 13/669,856, filed Nov. 6, 2012, entitled "FIBROBLAST GROWTH FACTOR MUTANTS HAVING IMPROVED; FUNCTIONAL HALF-LIE AND METHODS OF THEIR USE," which is a continuation-in-part of U.S. patent application Ser. No. 12/783,005 filed May 19, 2010 entitled "FIBROBLAST GROWTH FACTOR MUTANTS HAVING IMPROVED FUNCTIONAL HALF-LIFE; AND METHODS OF THEIR USE," which claims the benefit of priority to U.S. Provisional App. No. 61/179,751 filed May 20, 2009 entitled "FIBROBLAST GROWTH FACTOR; MUTANTS HAVING IMPROVED FUNCTIONAL HALF-LIFE AND METHODS OF THEIR USE," and U.S. Provisional App. No. 61/309,590 filed Mar. 2, 2010 entitled same, the contents and disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 2, 2012, is named 74606101.txt and is 19,710 bytes in size.

FIELD OF THE INVENTION

The present invention broadly relates to mutant fibroblast growth factor (FGF) proteins having higher thermostability and/or functional half-life for therapeutic applications. The present invention also relates to polynucleotides encoding such mutant FGF proteins and cells that may be used for expression. The present invention further broadly relates to methods of administering mutant FGF proteins to an individual, such as an individual having an ischemic or hypoxic condition or in need of wound healing or tissue repair.

BACKGROUND

Fibroblast growth factor-1 (FGF-1) is a potent mitogen and angiogenic factor suggested for use as a protein biopharmaceutical in treating a wide range of diseases and conditions. However, FGF-1 has poor thermal stability and a short half-life, and denatured or unfolded FGF-1 may form aggregates and become immunogenic. Pharmaceutical compositions of FGF-1 have been formulated with heparin to increase the stability and half-life of FGF-1. However, heparin has its own pharmacological properties, which may complicate using heparin-containing formulations of FGF-1. Therefore, a need continues in the art for new and improved compositions and methods for using modified versions of FGF-1 or related proteins having higher stability and longer functional half-life that are non-immunogenic and avoid the need for heparin.

SUMMARY

According to a first broad aspect of the present invention, a mutant fibroblast growth factor (FGF) protein is provided having a polypeptide sequence that is at least 90% identical to the polypeptide sequence of wild-type human FGF-1 protein (SEQ ID NO. 1), wherein the alanine (Ala) at an amino acid position of the mutant FGF protein corresponding to amino acid position 66 of wild-type human FGF-1 is replaced with cysteine (Cys), wherein the numbering of the amino acid positions is based on the numbering scheme for the 140 amino acid form of human FGF-1.

According to a second broad aspect of the present invention, a mutant fibroblast growth factor (FGF) protein is provided having a polypeptide sequence that is at least 90% identical to the polypeptide sequence of wild-type human FGF-1 protein (SEQ ID NO. 1), wherein the phenylalanine (Phe) at an amino acid position of the mutant FGF protein corresponding to amino acid position 132 of wild-type human FGF-1 is replaced with tryptophan (Trp), wherein the numbering of the amino acid positions is based on the numbering scheme for the 140 amino acid form of human FGF-1.

According to a third broad aspect of the present invention, a mutant fibroblast growth factor (FGF) protein is provided having a polypeptide sequence that is at least 90% identical to the polypeptide sequence of wild-type human FGF-2 protein (SEQ ID NO: 4), wherein the alanine (Ala) at an amino acid position of the mutant FGF protein corresponding to amino acid position 84 of wild-type human FGF-2 is replaced with cysteine (Cys).

According to a fourth broad aspect of the present invention, a mutant fibroblast growth factor (FGF) protein is provided having a polypeptide sequence that is at least 90% identical to the polypeptide sequence of wild-type human FGF-2 protein (SEQ ID NO: 4), wherein the phenylalanine (Phe) at an amino acid position of the mutant FGF protein corresponding to amino acid position 148 of wild-type human FGF-2 is replaced with tryptophan (Trp).

According to a fifth broad aspect of the present invention, polynucleotide sequences encoding a mutant FGF protein of the present invention and host cells containing such polynucleotide sequences are provided.

According to a sixth broad aspect of the present invention, a pharmaceutical composition comprising a mutant FGF protein of the present invention and a pharmaceutically acceptable carrier is provided.

According to a seventh broad aspect of the present invention, a method is provided comprising the following steps: (a) identifying an individual having an ischemic condition or disease; and (b) administering to the individual a composition comprising a mutant FGF protein of the present invention.

According to a eighth broad aspect of the present invention, a method is provided comprising the following steps: (a) identifying an individual having a wound or tissue damage; and (b) administering to the individual a composition comprising a mutant FGF protein of the present invention.

BRIEF DESCRIPTION OF THE DRAWINGS

Embodiments of the present invention will be described in conjunction with the accompanying drawings, in which:

FIG. 1 is the polypeptide sequence of the 155 amino acid form of wild-type human FGF-1 protein (SEQ ID NO: 2) with boxes showing alanine (A) at position 81 and phenylalanine (F) at position 147 that may each be mutated to or substituted with cysteine (C) and tryptophan (W), respectively, for mutant FGF proteins of the present invention. Shaded residues are removed (i.e., not present) in the 140 amino acid form of human FGF-1, and the underlined methionine (M) is removed (i.e., not present) in the 154 amino acid form of human FGF-1.

Figure 8:
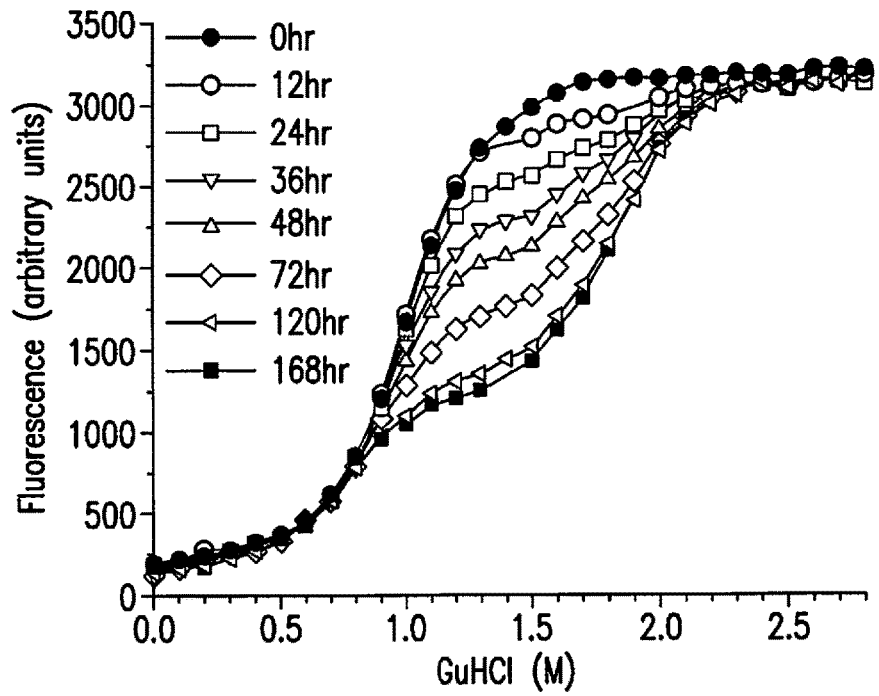

FIG. 2 is the polypeptide sequence of the 140 amino acid form of wild-type human FGF-1 protein (SEQ ID NO: 1) with boxes showing alanine (A) at position 66 and phenylalanine (F) at position 132 that may each be mutated to or substituted with cysteine (C) and tryptophan (W), respectively, for mutant FGF proteins of the present invention.

FIG. 3 is the polypeptide sequence of the 155 amino acid form of wild-type mouse FGF-1 protein (SEQ ID NO: 11) with boxes showing alanine (A) at position 81 and phenylalanine (F) at position 147 that may each be mutated or substituted to cysteine (C) and tryptophan (W), respectively, for mutant FGF proteins of the present invention.

FIG. 4 is the polypeptide sequence of the 155 amino acid form of wild-type human FGF-2 protein (SEQ ID NO: 4) with boxes showing alanine (A) at position 84 and phenylalanine (F) at position 148 that may each be mutated to or substituted with cysteine (C) and tryptophan (W), respectively, for mutant FGF proteins of the present invention.

FIG. 5 is the polypeptide sequence of the 154 amino acid form of wild-type mouse FGF-2 protein (SEQ ID NO: 12) with boxes showing alanine (A) at position 83 and phenylalanine (F) at position 147 that may each be mutated to or substituted with cysteine (C) and tryptophan (W), respectively, for mutant FGF proteins of the present invention.

FIG. 6 is a table showing the thermodynamic parameters for wild-type and mutant FGF-1 proteins in a crystallization buffer as determined by isothermal equilibrium denaturation using GuHCl and monitored using fluorescence spectroscopy.

FIG. 7-1 is a table showing crystallographic data collection and refinement statistics for mutant FGF-1 proteins.

FIG. 7-2 is a continuation of the table in FIG. 7-1.

FIG. 8 is graph showing isothermal equilibrium denaturation profiles for the Ala66→Cys mutant with air oxidation for the indicated time periods with the time-dependent conversion of the reduced form to the oxidized form associated with significantly enhanced stability.

Figure 9:
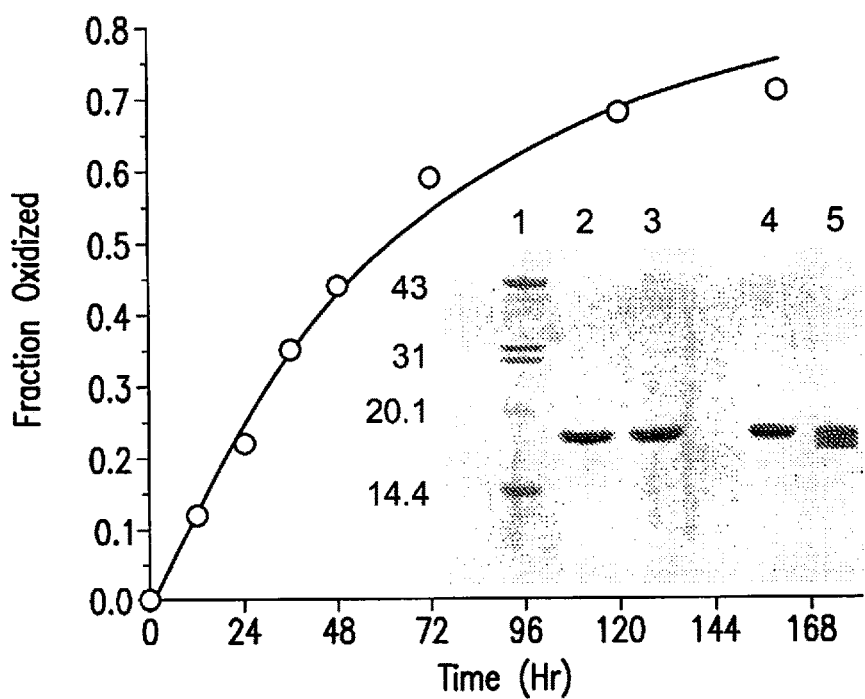

FIG. 9 is a graph showing a progress curve for the fractional increase in the oxidized form of the Ala66→Cys mutant protein from the isothermal equilibrium data in FIG. 8 with the fitted function having a first order exponential fit and yielding a first-order rate constant (i.e., half-life) of about 60 hours. An inset of a Coomassie blue-stained SDS PAGE gel is shown with mass standards in lane 1, a reduced wild-type FGF-1 in lane 2, a non-reduced wild-type FGF-1 in lane 3, a reduced Ala66→Cys FGF-1 mutant incubated in air oxidizing conditions for 48 hours in lane 4, and a non-reduced Ala66→Cys FGF-1 mutant incubated in air oxidizing conditions for 48 hours in lane 5 (reduced samples exposed to DTT prior to gel loading).

Figure 10:
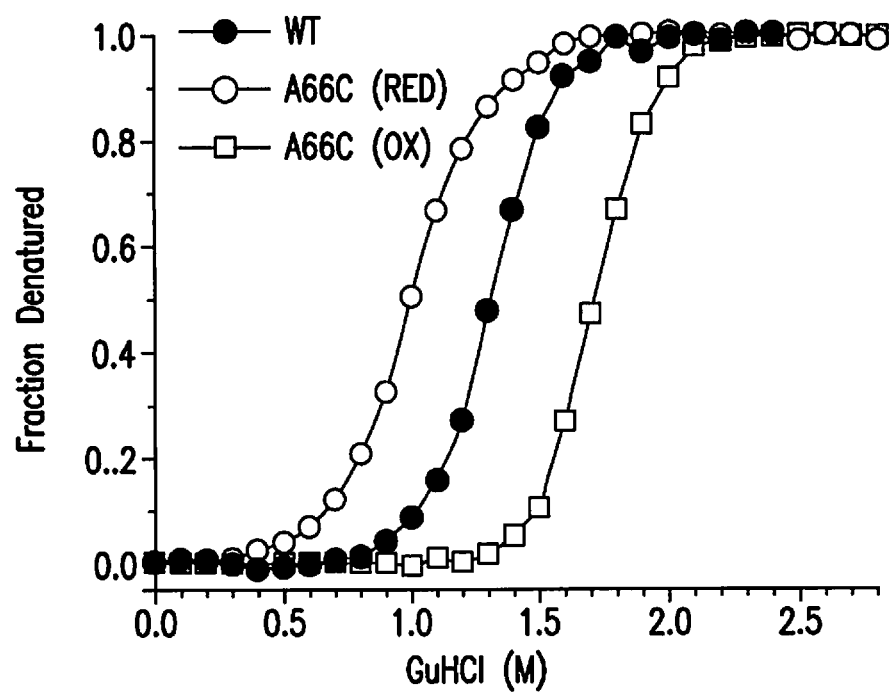

FIG. 10 is a graph showing the normalized fractional denaturation profiles for reduced and oxidized forms of the Ala66→Cys mutant FGF-1 protein and overlaid with the profile for wild-type FGF-1 with the denaturation profile for the oxidized form of the Ala66→Cys mutant FGF-1 protein obtained from a global fit to the oxidized component in the denaturation profiles shown in FIG. 8.

FIGS. 11A, 11B, 11C, 11D and 11E are a set of stereo diagrams of X-ray crystal structures (molecule A in the asymmetric unit in each case) showing the structural details of mutant FGF-1 adjacent to the site of mutation at position 83 mutants of FGF-1 (CPK coloring) overlaid with the coordinates of wild-type FGF-1 (1JQZ; grey coloring) with the Cys83→Ala mutation (FIG. 11A), the Cys83→Ser mutation (FIG. 11B), the Cys83→Thr mutation (FIG. 11C), the Cys83→Val mutation (FIG. 11D), and the Cys83→Ile mutation (FIG. 11E) shown. FIGS. 11A, 11B, 11C, 11D and 11E disclose "NEEA," "NEES," "NEET," "NEEV," and "NEEI" as SEQ ID NOS 15-19, respectively.

Figure 12:
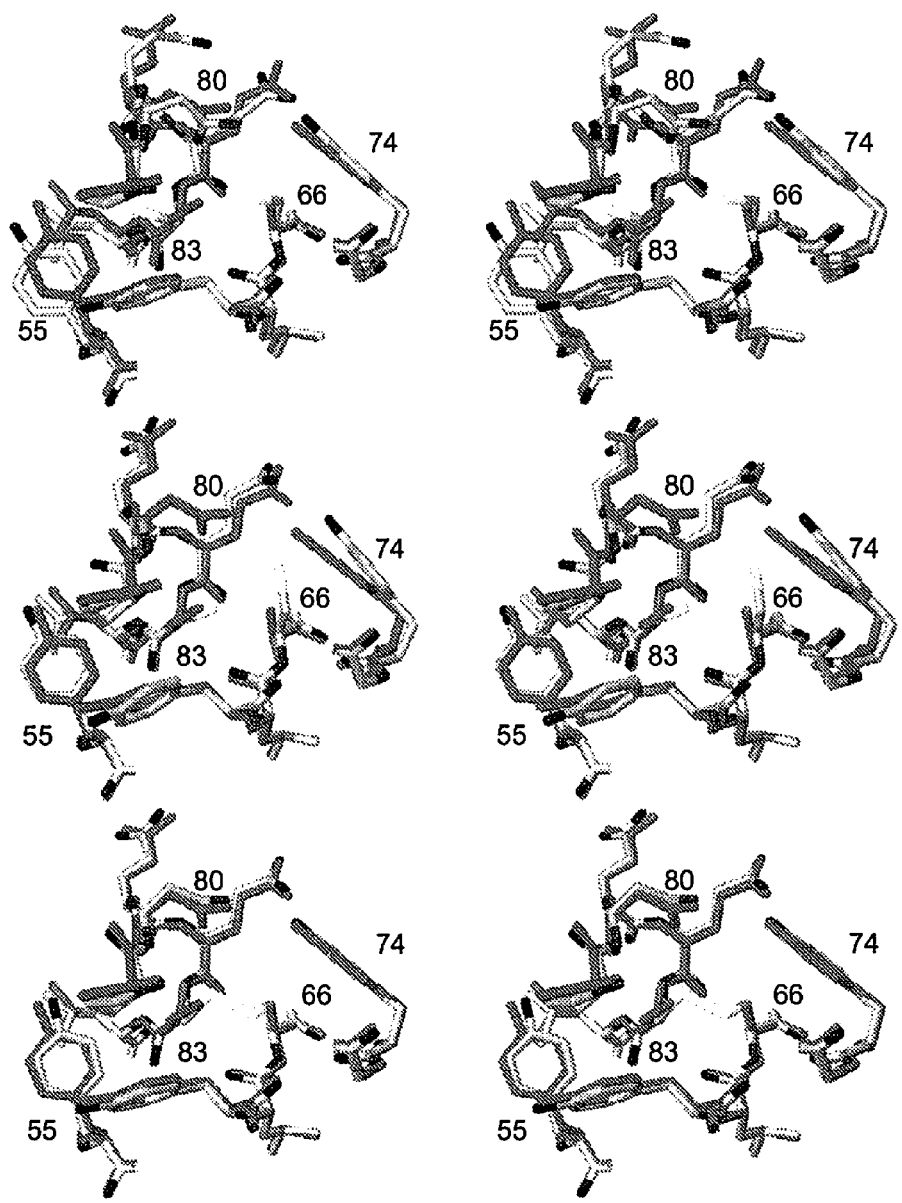

FIG. 12 is a relaxed stereo diagram of the X-ray crystal structures of the reduced and oxidized forms of the Ala66→Cys mutant. (top): molecule A in the asymmetric unit of reduced Ala66→Cys overlaid with wild-type FGF-1 (1JQZ; light gray). (middle): molecule B in the asymmetric unit of reduced Ala66→Cys overlaid with wild-type FGF-1 (1JQZ; light gray). (bottom): molecule A of oxidized Ala66→Cys overlaid with wild-type FGF-1 (1JQZ; light gray).

FIG. 13-1 is a table showing crystallographic data collection and refinement statistics for mutant FGF-1 proteins.

FIG. 13-2 is a continuation of the table of FIG. 13-1.

FIG. 14 is a table showing thermodynamic parameters for FGF-1 mutants determined from isothermal equilibrium denaturation using GuHCl in ADA buffer.

FIG. 15 is a table showing DSC data in ADA buffer in the presence of 0.7M GuHCl.

FIG. 16 is a table showing mitogenic activity of wild-type and mutant FGF-1 proteins in the absence and presence of 10 U/ml heparin on NIH 3T3 fibroblasts, protein functional half-life in unconditioned medium, and protein half-life with 200:1 trypsin digestion.

FIG. 17 is a table showing the mitogenic activity and functional half-life of the wild-type FGF-1 and Ala66→Cys (oxidized form) mutant.

Figure 18:
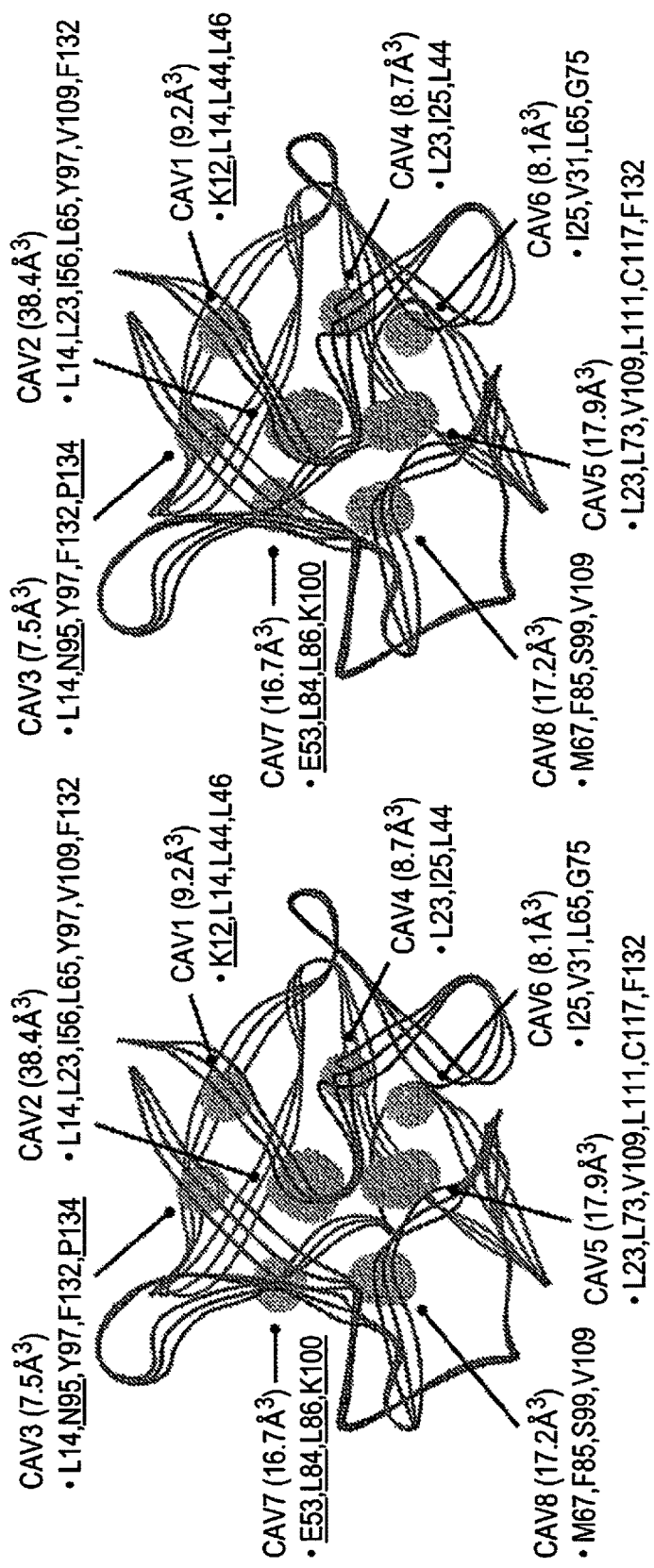

FIG. 18 is a relaxed stereo ribbon diagram of wild-type FGF-1 (1JQZ; molecule A) indicating the location of the eight solvent-excluded cavities identified using a 1.2 Å radius probe with residues bordering the cavities indicated in single letter amino acid code, and underlined residues having solvent accessibility.

FIGS. 19A, 19B, 19C, 19D and 19E are a set of relaxed stereo diagrams of the Leu44→Trp mutant (FIG. 19A), Phe85→Trp mutant (FIG. 19B), Phe132→Trp mutant (FIG. 19C), Val31→Ile mutant (FIG. 19D), and Cys117→Ile mutant (FIG. 19E) with each overlaid onto the wild-type FGF-1 (1JQZ) structure (dark gray) and with the cavities adjacent to these mutant positions within the wild-type structure that are detectable using a 1.2 Å radius probe shown.

Figure 20A:
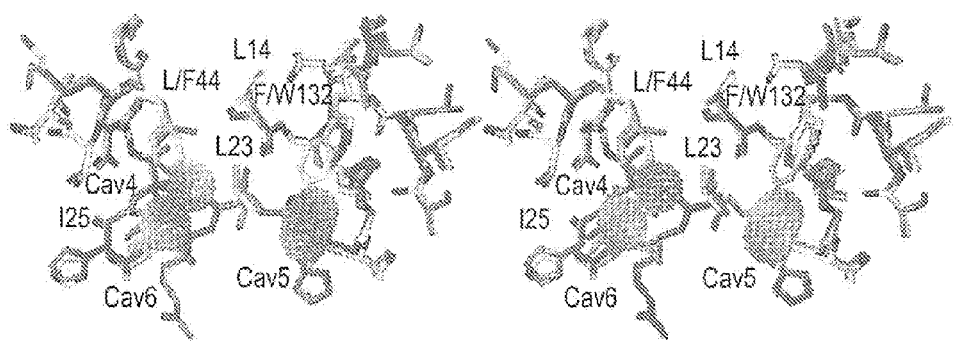
Figure 20B:
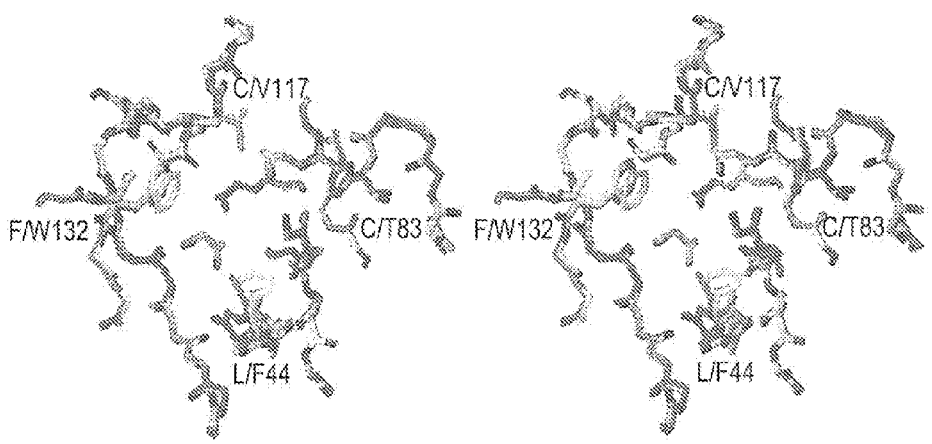

FIGS. 20A and 20B are a set of relaxed stereo diagrams of the Leu44→Phe+Phe132→Trp double mutant of FGF-1 FIG. A, and the Leu44→Phe+Cys83→Thr+Cys117→Val+Phe132→Trp quadruple mutant of FGF-1 FIG. B overlaid onto the wild-type (1JQZ) FGF-1 structure (dark gray) with FIG. A showing the location of the three cavities (cav4, cav5 and cav6) that are filled in response to the Leu44→Phe+Phe132→Trp double mutation and with FIG. B the overlaid with the wild-type structure and showing only the main chain atoms within 5 Å of positions 44, 83, 117, and 132.

Figure 21:
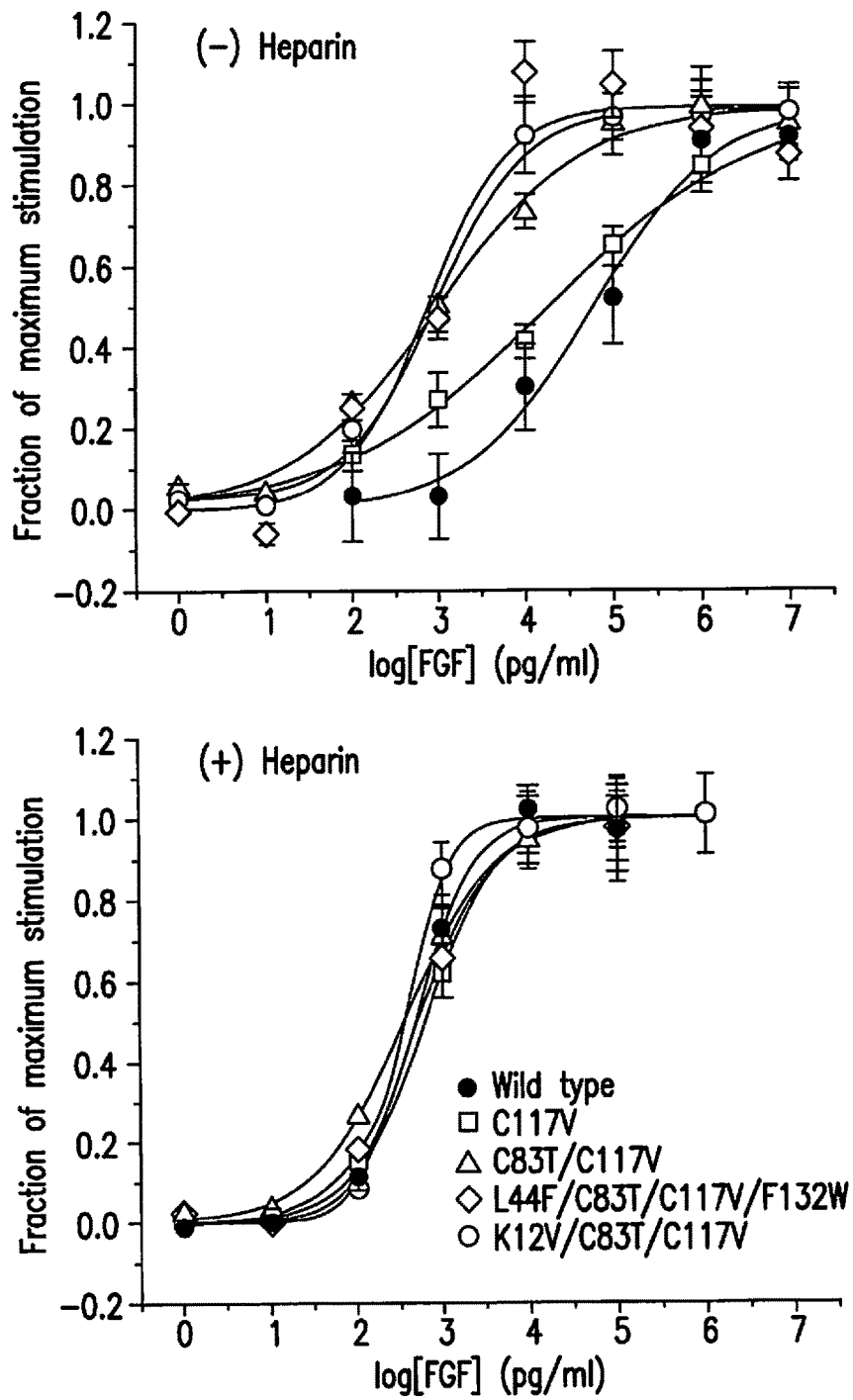

FIG. 21 is a set of graphs of a NIH 3T3 fibroblast mitogenic assay of wild-type and mutant forms of FGF-1 in the absence (top) and presence (bottom) of 10 U/ml heparin.

Figure 22A:
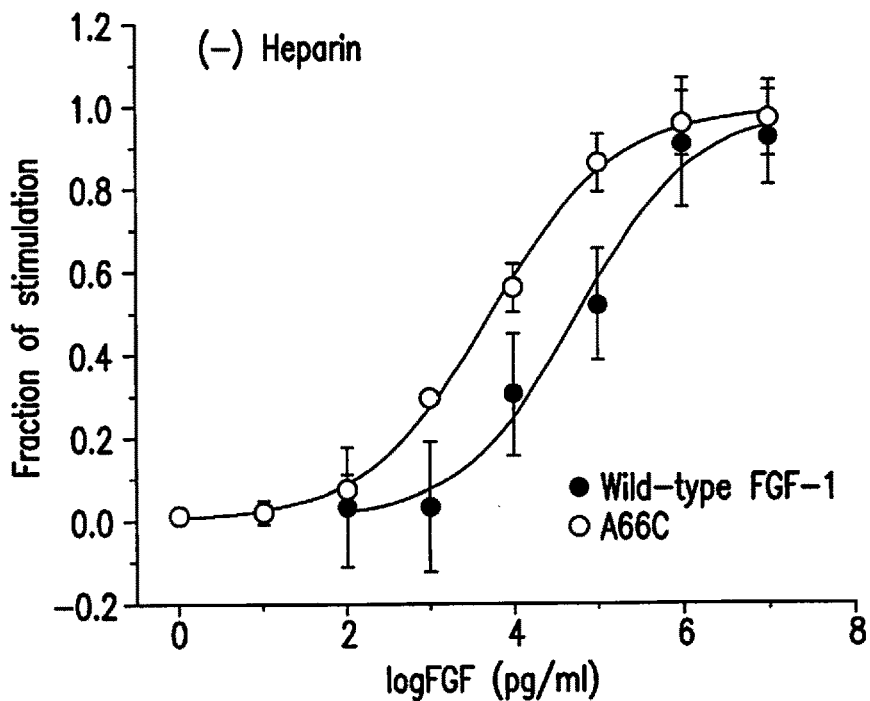
Figure 22B:
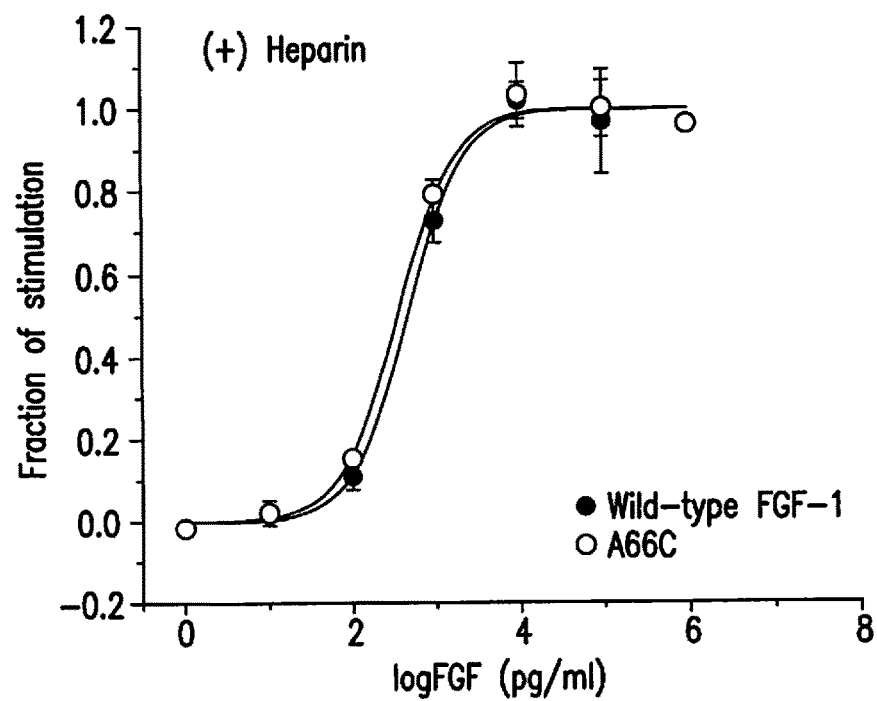

FIGS. 22A and 22B are a set of graphs showing mitogenic activity of wild-type FGF-1 (filled circles) and Ala66→Cys mutant (open circles) in the absence (FIG. 22A) or presence (FIG. 22B) of 10 U/ml heparin.

Figure 23:
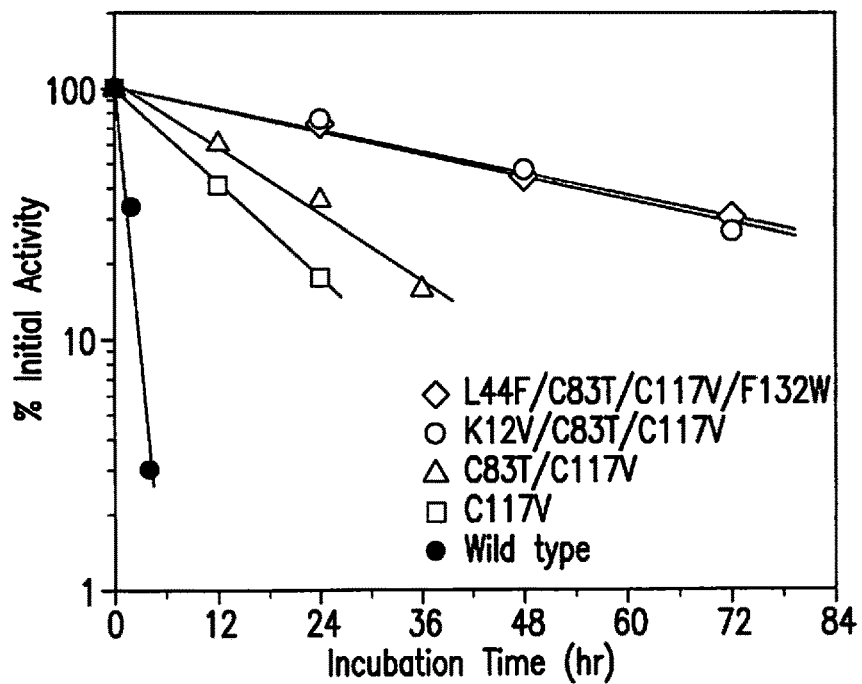

FIG. 23 is a graph showing the log of the percent initial mitogenic activity plotted as a function of incubation time (i.e., functional half-life) prior to measurement of mitogenic activity providing inactivation rates of wild-type and mutant forms of FGF-1 in unconditioned DMEM at 37° C.

Figure 24:
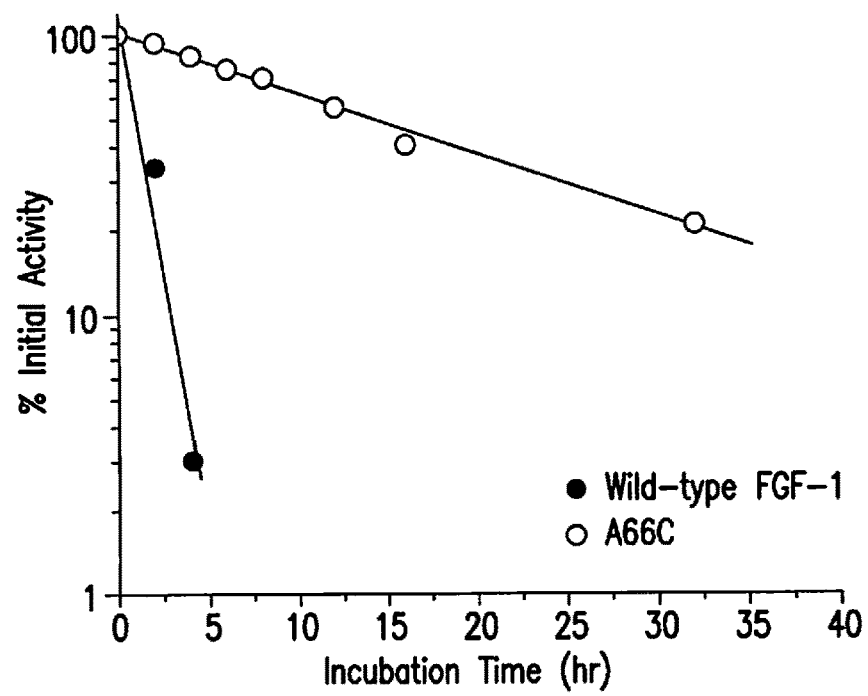
Figure 25A:
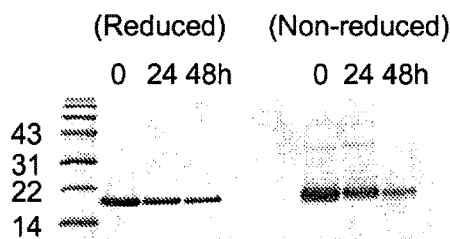
Figure 25B:
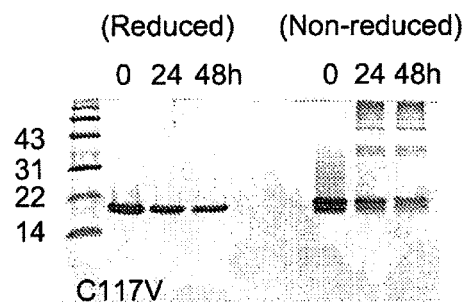
Figure 25C:
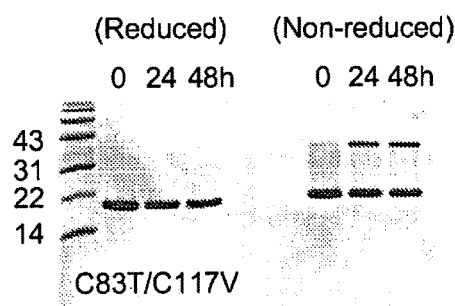
Figure 25D:
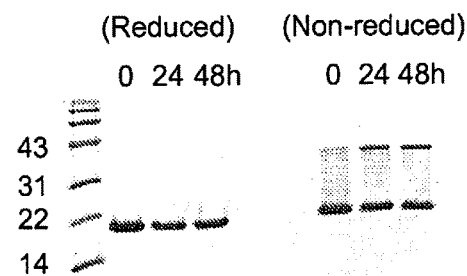
Figure 25E:
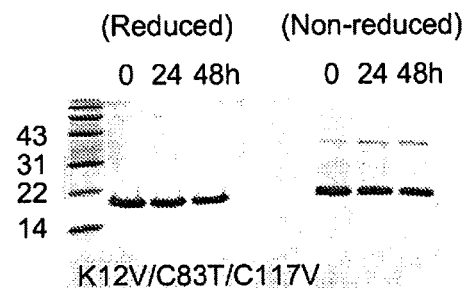

FIG. 24 is a graph showing the functional half-life assay for wild-type FGF-1 (filled circles) and Ala66→Cys mutant (open circles).

FIGS. 25A, 25B, 25C, 25D and 25E are a set of images of Coomassie Brilliant Blue stained 16.5% Tricine SDS-PAGE gels of a time-course incubation in TBS of wild-type FGF-1 (FIG. 25A), Cys117→Val mutant FGF-1 (FIG. 25B), Cys83→Thr+Cys117→Val mutant FGF-1 (FIG. 25C), Leu44→Phe+Cys83→Thr+Cys117→Val+Phe132→Trp mutant FGF-1 (FIG. 25D), and Lys12→Val+Cys83→Thr+Cys117→Val (FIG. 25E) with samples labeled "reduced" made in 5% BME prior to gel loading.

Figure 26:
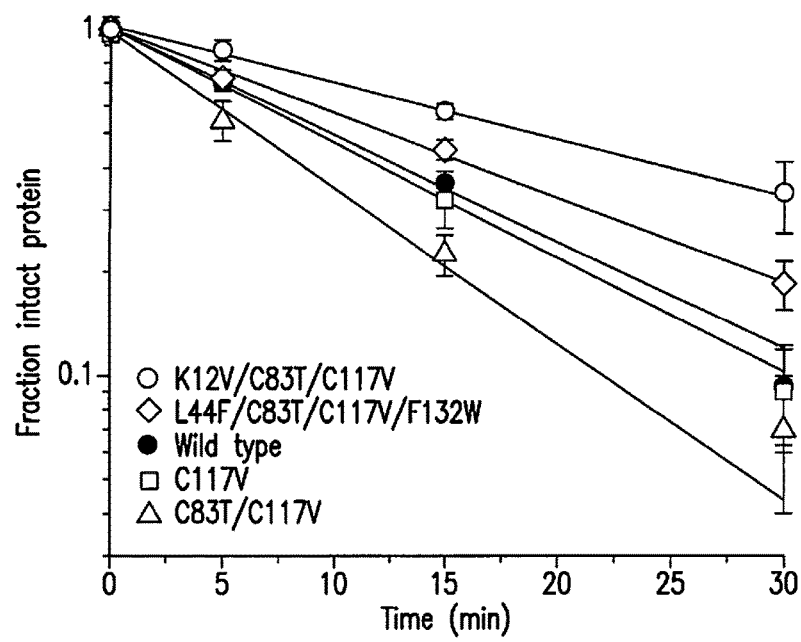

FIG. 26 is a time course plot of the proteolytic digestion of the wild-type and mutant forms of FGF-1 by trypsin (200:1 molar ratio, respectively) in TBS pH 7.4 at 37° C. showing the fraction of intact protein quantified by scanning densitometry of Coomassie Blue stained Tricine SDS PAGE gels.

Figure 27:
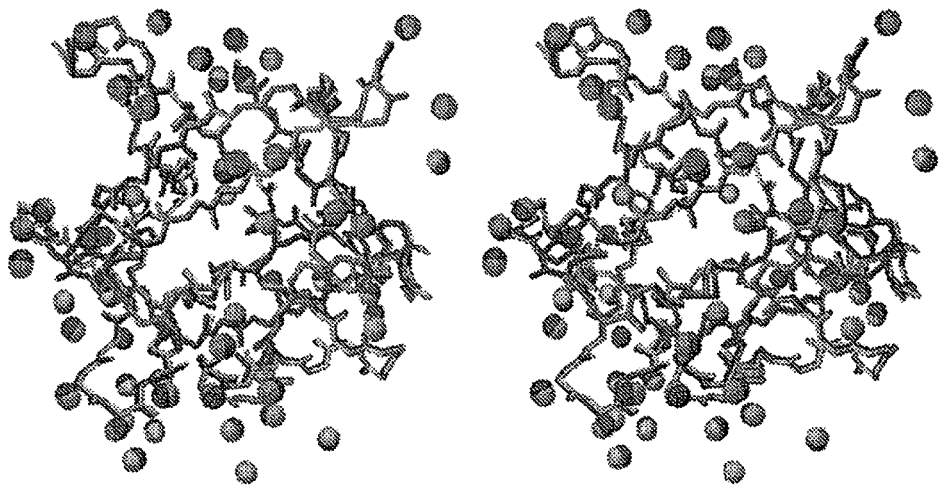

FIG. 27 is a relaxed stereo diagram showing an overlay of the main chain atoms of the Leu44→Phe+Cys83→Thr+Cys117→Val+Phe132→Trp mutant (light gray) with wild-type FGF-1 (dark gray) with this set of atoms overlaid with a root-mean-square deviation of 0.25 Å and with conserved solvent molecules shown as spherical representations.

Figure 28:
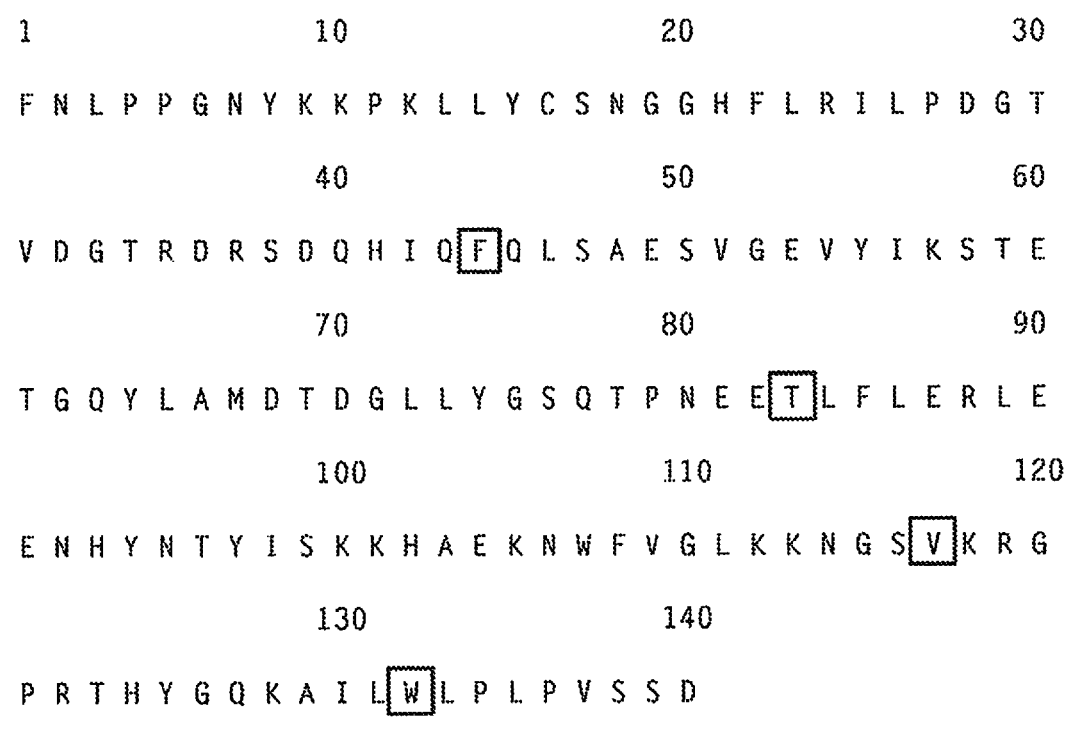

FIG. 28 is the polypeptide sequence of the 140 amino acid form of wild-type human FGF-1 protein with boxes showing cysteine (C) at position 83, cysteine (C) at position 117, leucine (L) at position 44 and phenylalanine (F) at position 132 that are each mutated to or substituted with threonine (T), valine (V), phenylalanine (F) and tryptophan (W), respectively, for mutant FGF proteins of the present invention (SEQ ID NO: 13).

DETAILED DESCRIPTION

Definitions

Where the definition of terms departs from the commonly used meaning of the term, applicant intends to utilize the definitions provided below, unless specifically indicated.

For purposes of the present invention, the terms "thermodynamic stability" or "thermostability" of a protein refer interchangeably to the ability of a protein to maintain its tertiary structure (i.e., to resist denaturation or unfolding) at a given temperature or in the presence of a denaturant. The thermostability of a protein (e.g., a mutant FGF protein) may be expressed in terms of the Gibb's free energy equation relative to a standard (e.g., wild-type FGF protein) according to known methods.

For purposes of the present invention, the term "functional half-life" of a FGF protein refers to the amount of time it takes for the activity or effect of a FGF protein (e.g., a mutant FGF protein) to become reduced by half. For example, the functional half-life may be based on the activity of a FGF protein over time in inducing growth, proliferation, and/or survival of cells, such as according to a cultured fibroblast proliferation assay. The functional half-life of a protein may be different than the thermostability of the same protein since these are separable properties of proteins. For example, a protein may be mutated such that the thermostability of the protein is decreased while its functional half-life is increased.

For purposes of the present invention, the terms "correspond" or "corresponding" in reference to a protein sequence refer interchangeably to an amino acid position(s) of a protein, such as a mutant FGF protein, that is equivalent or corresponds to an amino acid position(s) of one or more other protein(s), such as a wild-type FGF protein, according to any standard criteria known in the art. An amino acid at a position of a protein may be found to be equivalent or corresponding to an amino acid at a position of one or more other protein(s) based on any relevant evidence, such as the primary sequence context of the each amino acid, its position in relation to the N-terminal and C-terminal ends of its respective protein, the structural and functional roles of each amino acid in its respective protein, etc. For proteins having similar or nearly identical polypeptide sequences, a "corresponding" amino acid(s) and corresponding amino acid position(s) between proteins may be determined or deduced by sequence alignment and comparison. However, "corresponding" amino acid(s) for two or more proteins may have different amino acid position numbers or numbering (e.g., when counted from the N-terminus of each protein) since the two or more proteins may have different lengths and/or one or more substitutions, insertions, deletions, etc. For example, related proteins may have deletions or insertions in relation to each other that offset the numbering of their respective or corresponding amino acid sequences (i.e., based on their primary structure or sequence). An amino acid position(s) of a protein, such as a mutant FGF protein, may "correspond" to an amino acid position(s) of one or more other protein(s) if the amino acid positions are structurally equivalent or similar when comparing the three-dimensional structures (i.e., tertiary structures) of the respective proteins. A person skilled in the art would be able to determine "corresponding" amino acids and/or "corresponding" amino acid positions of two or more proteins based on their protein sequences and/or protein folding or tertiary structure.

For purposes of the present invention, the terms "identical" or "identity" refer to the percentage of amino acid residues of two or more polypeptide sequences having the same amino acid at corresponding positions. For example, a protein that is at least 90% identical to a polypeptide sequence will have at least 90% of its residues that are the same as those in the polypeptide sequence at corresponding positions.

For purposes of the present invention, the term "Fgf-1 subfamily" refers to the subfamily of mammalian genes, and mutants thereof, that are more related in sequence to mammalian Fgf-1 genes than other mammalian Fgf subfamilies. For example, Fgf-1 subfamily members may include mammalian orthologs of Fgf-1 and Fgf-2. In addition, the term "FGF-1 subfamily" or "FGF A subfamily" refer to the subfamily of mammalian proteins, and mutants thereof, that are more related in sequence to mammalian FGF-1 proteins than other mammalian FGF subfamilies. For example, FGF-1 subfamily members may include mammalian FGF-1 and FGF-2.

For purposes of the present invention, the terms "individual," "subject," or "patient" refer interchangeably to a mammalian organism, such as a human, mouse, etc., that is administered a mutant FGF protein of the present invention for a therapeutic or experimental purpose.

Description

Protein biopharmaceuticals are an important and growing area of human therapeutics, but the intrinsic property of proteins to adopt alternative conformations (e.g., during protein unfolding) presents numerous challenges limiting their effective application as biopharmaceuticals. Although still a comparatively small percentage overall, protein biopharmaceuticals are the fastest-growing category of new drug approvals and currently target over 200 human diseases, including cancers, heart disease, Alzheimer's, diabetes, multiple sclerosis, AIDS, and arthritis. See, e.g., Crommelin, D. J. A., et al., "Shifting paradigms:

biopharmaceuticals versus low molecular weight drugs," *International Journal of Pharmaceutics* 266:3-16 (2003), the entire contents and disclosure of which are hereby incorporated by reference. The impact of protein biopharmaceuticals upon U.S. healthcare and the economy is substantial and growing rapidly. However, in comparison to traditional small molecules, proteins present new and significant challenges that need to be overcome before their full potential as therapeutic agents may be realized. One unique property of proteins is that they are able to adopt different structural conformations, and this profoundly influences critically-important properties of proteins, such as their function, solubility, bioavailability, half-life, aggregation, toxicity, immunogenicity, etc. See, e.g., Frokjaer, S. et al., "Protein drug stability: a formulation challenge," *Nature Reviews* 4:298-306 (2005); Hermeling, S. et al., "Structure-immunogenicity relationships of therapeutic proteins," *Pharmaceutical Research* 21:897-903 (2004); and Krishnamurthy, R. et al., "The stability factor: importance in formulation development," *Current Pharmaceutical Biotechnology* 3:361-371 (2002), the entire contents and disclosures of which are hereby incorporated by reference. A key intrinsic property of proteins in this regard is their thermodynamic stability ($\Delta G_{unfolding}$) which defines an equilibrium between native and denatured states of a protein.

The thermodynamic stability of a protein may be of particular significance in therapeutic applications because unfolded or aggregated forms of a protein may be potentially toxic and/or immunogenic. For example, neutralizing antibodies in patients treated with interferon-alpha 2a were observed when the protein is stored at room temperature and formed detectable aggregates, but both the formation of aggregates and immunogenicity were reduced upon storage at 4° C. (where $\Delta G_{unfolding}$ increased). See, e.g., Hochuli, E. "Interferon immunogenicity: technical evaluation of interferon-alpha 2a," *Journal of Interferon and Cytokine Research* 17:S15-S21 (1997), the entire contents and disclosure of which are hereby incorporated by reference. In a different study, persistent antibodies were generated in patients treated with human growth hormone with formulations containing 50-70% aggregates. However, when the formulation of human growth hormone was modified to contain less than 5% aggregates, only transient or no antibodies were observed. See, e.g., Moore, W. V. et al., "Role of aggregated human growth hormone (hGH) in development of antibodies to hGH," *Journal of Clinical Endocrinology and Metabolism* 51:691-697 (1980), the entire contents and disclosure of which are hereby incorporated by reference. In yet another study using recombinant clotting factor VIII in mice, the formation of aggregates was associated with the emergence of entirely novel immunogenic epitopes. See, e.g., Purohit, V. S. et al., "Influence of aggregation on immunogenicity of recombinant human Factor VIII in hemophilia A mice," *Journal of Pharmaceutical Sciences* 95:358-371 (2006), the entire contents and disclosure of which are hereby incorporated by reference. Thus, protein stability, denaturation, aggregation and immunogenicity may be critical and interrelated issues influencing the successful application of proteins as biopharmaceuticals.

Various efforts have been made to increase the thermodynamic stability and/or half-life of proteins that are intended for use as biopharmaceuticals, while reducing their aggregation and/or immunogenicity. One such approach uses covalent attachment of polyethylene glycol (PEG), a highly soluble and biocompatible polymer, to substantially increase the circulating half-life of proteins through reduced renal clearance due to a substantial increase in the molecular mass of these proteins. The attached PEG molecule may also physically mask regions of the protein that would otherwise be susceptible to proteolytic attack or immune recognition, increasing further the circulating half-life and reducing immunogenicity. However, attachment of PEG molecules ("PEGylation") typically does not increase the formal thermodynamic stability of proteins and has been noted to reduce the thermodynamic stability in some cases. See, e.g., Basu, A., et al., "Structure-function engineering of interferon-β-1b for improving stability, solubility, potency, immunogenicity, and pharmacokinetic properties by site-selective mono-PEGylation," *Bioconjugate Chemistry* 17 (2006); and Monfardini, C. et al., "A branched monomethoxypoly(ethylene glycol) for protein modification," *Bioconjugate Chemistry* 6:62-69 (1995), the entire contents and disclosure of which are hereby incorporated by reference.

Therefore, the beneficial properties of PEGylation are primarily associated with modulation of renal clearance and a reduction in proteolysis and immune recognition (i.e., PEGylation generally does not increase thermodynamic stability of a protein). One problem with PEGylation is that it may interfere with critical functional interfaces on the protein surface, often reducing receptor/ligand affinity by two or more orders of magnitude. However, PEGylation studies do show that shielding of epitopes on the protein surface may substantially reduce or eliminate the immunogenic potential of a protein, which may have important ramifications for protein engineering by suggesting that mutations at solvent-inaccessible positions within proteins may minimize their immunogenic potential.

The fibroblast growth factors (gene=Fgf; protein=FGF) are a family of polypeptides with diverse roles in development and metabolism. Fgfs have been found in many multicellular organisms, ranging from *Caenorhabditis elegans* to *Homo sapiens*. Two Fgf genes have been identified in *C. elegans*, while the mouse and human each share 22 Fgf genes. See, e.g., Itoh, N. et al., "Evolution of the Fgf and Fgfr gene families," *Trends Genet* 20 (2004); Popovici, C. et al., "An evolutionary history of the FGF superfamily," *BioEssays* 27:849-857 (2005); and Itoh, N. et al., "Functional evolutionary history of the mouse Fgf gene family," *Developmental Dynamics* 237:18-27 (2008), the entire contents and disclosures of which are hereby incorporated by reference. Fgf genes generally encode potent mitogens for a broad spectrum of cell types, including vascular cells.

Human and mouse Fgf genes and proteins may be divided into seven subfamilies based on phylogenetic analysis: Fgf-1 or FGF A subfamily (including FGF-1 and FGF-2 proteins); Fgf-4 or FGF C subfamily (including FGF-4, FGF-5, and FGF-6 proteins); Fgf-7 or FGF B subfamily (including FGF-3, FGF-7, FGF-10, and FGF-22 proteins); Fgf-8 or FGF D subfamily (including FGF-8, FGF-17, and FGF-18 proteins); Fgf-9 or FGF E subfamily (including FGF-9, FGF-16, and FGF-20 proteins); intracellular iFgf or FGF F subfamily (including FGF-11, FGF-12, FGF-13, and FGF-14 proteins); and hormone-like hFgf or FGF G subfamily (including FGF-15/FGF-19, FGF-21, and FGF-23 proteins). See, e.g., Itoh, N. et al. (2008), supra; Popovici, C. et al. (2005), supra; and Ornitz, D. M. et al., "Fibroblast growth factors," *Genome Biology* 2(3):3005.1-3005.12 (2001), the entire contents and disclosure of which are hereby incorporated by reference.

Several members of the FGF family of proteins, including Fgf-1 subfamily FGF-1 and FGF-2 proteins (also referred to as acidic FGF and basic FGF, respectively), have the potential of providing "angiogenic therapy" for the treatment of ischemic conditions or diseases (i.e., diseases caused by insufficient blood flow to one or more tissues), such as coronary artery disease, peripheral vascular disease, peripheral arterial occlusion or disease (e.g., critical limb ischemia or CLI), etc., by triggering neovascularization of affected tissues. See, e.g., Nikol, S. et al., "Therapeutic Angiogenesis With Intramuscular NV1FGF Improves Amputation-free Survival in Patients With Critical Limb Ischemia," *Mol Ther* 16(5):972-978 (2008), the entire contents and disclosure of which are hereby incorporated by reference. In addition, FGF proteins may be used for tissue repair and wound healing by triggering angiogenesis and proliferation of fibroblasts involved in healing damaged tissue and filling the wound space with new tissue.

FGF-1 has also been suggested for use in regenerating nervous system tissue following spinal cord injury or trauma, such as brachial plexus injury, neuroimmunologic disorders, such as acute or idiopathic transverse myelitis (TM), or any other disease or condition where regeneration and/or protection of neurons or neural tissue is desired, since FGF-1 is believed to stimulate neural proliferation and growth and may be neuroprotective. See, e.g., Lin P-S. et al., "Spinal Cord Implantation with Acidic Fibroblast Growth Factor as a Treatment for Root Avulsion in Obstetric Brachial Plexus Palsy," *J Chin Med Assoc* 68(8):392-396 (2005); Cheng, H. et al., "Spinal Cord Repair with Acidic Fibroblast Growth Factor as a Treatment for a Patient with Chronic Paraplegia," *SPINE* 29(14):E284-E288 (2004); and Lin, P-H., "Functional recovery of chronic complete idiopathic transverse myelitis after administration of neurotrophic factors," *Spinal Cord* 44:254-257 (2006), the entire contents and disclosures of which are hereby incorporated by reference.

Pharmaceutical or therapeutic administration of FGF proteins, such as FGF-1 and FGF-2, is limited by the fact that wild-type FGF proteins have poor thermodynamic stability and a short half-life. See, e.g., Szlachcic, A. et al., "Structure of a highly stable mutant of human fibroblast growth factor 1," *Acta Cryst*. D65:67-73 (2009), the entire contents and disclosures of which are hereby incorporated by reference. For example, FGF-1 has poor thermodynamic stability with a melting temperature (i.e., a midpoint of thermal denaturation, or $T_m$) that is only marginally above physiological temperature. See, e.g., Copeland, R. A., et al., "The structure of human acidic fibroblast growth factor and its interaction with heparin," *Archives of Biochemistry and Biophysics* 289:53-61 (1991), the entire contents and disclosure of which are hereby incorporated by reference. The functional half-life of wild-type FGF-1 in unconditioned DMEM is only about 1.0 hour according to a cultured fibroblast proliferation assay. Although incubation experiments in TBS buffer demonstrate aggregation and loss of soluble monomeric of FGF-1 over a different time scale, these studies do show that loss of soluble monomeric FGF-1 protein over time is due to irreversible aggregation with soluble FGF-1 protein showing formation of higher-mass disulfide adducts. Because of its intrinsic property of instability, FGF-1 is prone to both aggregation and proteolysis, which may cause immunogenicity. Accordingly, substantial effort has been spent on identifying appropriate formulations to counteract these intrinsic properties often with mixed success.

FGF-1 is a "heparin-binding" growth factor, and upon binding of heparin, the $T_m$ of FGF-1 increases by about 20° C., and heparin-bound FGF-1 exhibits reduced susceptibility to denaturation-induced aggregation, thiol reactivity, and proteolytic degradation. See, e.g., Copeland R. A. et al. (1991), supra; and Gospodarowicz, D. et al., "Heparin protects basic and acidic FGF from inactivation," *Journal of Cellular Physiology* 128:475-484 (1986), the entire contents and disclosures of which are hereby incorporated by reference. Therefore, one approach to overcoming the therapeutic limitation of FGF protein instability is to administer FGF-1 bound to heparin. Indeed, FGF-1 formulated with the addition of heparin as a protein biopharmaceutical is currently in phase II clinical trials (NCT00117936) for pro-angiogenic therapy in coronary heart disease. However, heparin adds considerable additional expense, has its own pharmacological properties (e.g., it is an anti-coagulant), is derived from animal tissues (with associated concerns regarding the potential for infectious agents), and causes adverse inflammatory or allergic reactions in a segment of the population. Thus, formulation efforts to modulate the physical properties of a protein are often difficult to achieve and can introduce undesired additional cost or side effects.

An alternative approach to "PEGylation" or formulation with heparin is to alter the physical properties of an FGF protein by mutagenesis. By changing its amino acid sequence, an FGF protein may have greater thermodynamic stability and/or increased functional half-life as well as increased solubility and resistance to proteolytic degradation, aggregation, or immunogenic potential. Mutating proteins to improve their properties for human therapeutic application is a viable approach. For example, over thirty mutant forms of proteins have been approved by the FDA for use as human biopharmaceuticals. See, e.g., Kurtzman, A. L. et al., "Advances in directed protein evolution by recursive genetic recombination: applications to therapeutic proteins," *Curr Opin Biotech* 12:361-370 (2001), the entire contents and disclosures of which are hereby incorporated by reference. Examples include mutations that contribute to increased yields during purification, increased in vivo functional half-life, or increased specific activity, such as mutations of buried free-cysteine residues in β-interferon (Betaseron®) and interleukin-2 (Proleukin®) as well as others hypothesized to increase thermostability. Thus, a mutational approach to improve the physical properties of proteins is a viable route to develop "second-generation" protein biopharmaceuticals having improved thermodynamic stability and/or functional half-life.

However, the concepts of thermodynamic stability and half-life are separable properties of a protein. For example, as described further below, mutation of buried free cysteine residues of proteins may increase their functional half-life despite causing a reduced thermodynamic stability because mutation of these reactive free cysteine residues avoids the irreversible formation of disulfide bonds that are incompatible with the native conformation of the protein. Therefore, combining separate mutations that eliminate free cysteines with other mutations that increase the thermostability of a protein may have a synergistic effect on the half-life of the protein by avoiding the irreversible denaturation pathway resulting from thiol reactivity of the free cysteine (e.g., disulfide formation) while simultaneously increasing the thermodynamic stability of the protein. This is especially true considering that protein unfolding, which is dependent on protein stability, is often a necessary first step for the irreversible denaturation pathway resulting from exposure of the reactive free cysteine.

The fundamental FGF protein structure is described by a ~120 amino acid domain that forms a β-trefoil architecture. See, e.g., Murzin, A. G. et al., "β-Trefoil fold. Patterns of structure and sequence in the kunitz inhibitors interleukins-1β and lot and fibroblast growth factors," *Journal of Molecular Biology* 223:531-543 (1992), the entire contents and disclosure of which are hereby incorporated by reference. Among the 22 members of the mouse/human FGF family, three positions are absolutely conserved, and include Gly71, Cys83, and Phe132 (using numbering scheme of the 140 amino acid form of FGF-1). Gly71 is located at the i+3 position in a type I β-turn and is the statistically-preferred residue at this position due to structural considerations of backbone strain. See, e.g., Hutchinson, E. G. et al., "A revised set of potentials for beta-turn formation in proteins," *Protein Sci* 3:2207-16 (1994); Guruprasad, K. et al., "Beta- and gamma-turns in proteins revisited: a new set of amino acid turn-type dependent positional preferences and potentials," *J Biosci* 25:143-56 (2000); Kim, J. et al., "Identification of a key structural element for protein folding within β-hairpin turns," *Journal of Molecular Biology* 328:951-961 (2003); and Lee, J. et al., "A logical OR redundancy with the Asx-Pro-Asx-Gly type I β-turn motif," *Journal of Molecular Biology* 377:1251-1264 (2008), the entire contents and disclosures of which are hereby incorporated by reference.

Phe132 is a large aromatic residue that forms part of the hydrophobic core of the protein. Such large hydrophobic residues within the protein interior make a substantial contribution to protein stability. See, e.g., Shortle, D. et al., "Contributions of the Large Hydrophobic Amino Acids to the Stability of Staphylococcal Nuclease," *Biochemistry* 29:8033-8041 (1990); Eriksson, A. E. et al., "Response of a protein structure to cavity-creating mutations and its relation to the hydrophobic effect," *Science* 255:178-183 (1992); and Brych, S. R. et al., "Structure and stability effects of mutations designed to increase the primary sequence symmetry within the core region of a β-trefoil," *Protein Science* 10:2587-2599 (2001), the entire contents and disclosures of which are hereby incorporated by reference. Cys83 is located at a solvent-inaccessible position in the protein and therefore has no identifiable role related to receptor-binding functionality, neither does it provide significant buried hydrophobic area that might contribute to stability.

FGF-1 contains three free-cysteine residues at positions 16, 83, and 117 (using the 140 amino acid numbering scheme of human FGF-1) that may limit the functional stability due to reactive thiol chemistry. See, e.g., Ortega, S. et al., "Conversion of cysteine to serine residues alters the activity, stability, and heparin dependence of acidic fibroblast growth factor," *Journal of Biological Chemistry* 266:5842-5846 (1991); and Estape, D., et al., "Susceptibility towards intramolecular disulphide-bond formation affects conformational stability and folding of human basic fibroblast growth factor," *Biochem J* 335:343-9 (1998), the entire contents and disclosures of which are hereby incorporated by reference.

Cysteine is the second-least abundant amino acid in proteins (after tryptophan), yet is among the most highly conserved in functionally important sites involving catalysis, regulation, cofactor binding, and stability. See, e.g., Fomenko, D. E. et al., "Functional diversity of cysteine residues in proteins and unique features of catalytic redox-active cysteines in thiol oxidoreductases," *Mol Cells* 26:228-35 (2008), the entire contents and disclosure of which are hereby incorporated by reference. The unique properties of cysteine have their basis in the side chain Sγ sulfur atom participating in a variety of different functional roles, including disulfide bond formation, metal-binding, electron donation, hydrolysis, and redox-catalysis. However, some cysteine residues do not participate in these functional roles and exist instead as structural free-cysteines within the protein. These free cysteines are approximately evenly distributed between interior and solvent exposed positions of proteins. See, e.g., Petersen, M. T. N. et al., "Amino acid neighbours and detailed conformational analysis of cysteines in proteins," *Protein Engineering* 12:535-548 (1999), the entire contents and disclosure of which are hereby incorporated by reference.

Published work has made note of the fact that free-cysteine residues within the interior of a protein may effectively limit the protein's functional half-life. Free cysteines have chemically reactive thiols that are subject to chemical modification (e.g., covalent disulfide bond formation) should they become exposed (i.e., solvent-accessible or present on the protein surface), which occurs transiently during the dynamic equilibrium process of maintaining protein structure. The chemical reactivity of these free cysteine residues may present major structural difficulties for accommodation within the native protein interior and may result in an irreversible unfolding pathway when these free cysteine residues become exposed. Free-cysteine residues are chemically reactive thiols that are subject to covalent bond formation with other reactive thiols. If present on the solvent-accessible surface of a protein, a free cysteine may potentially participate in a disulfide adduct while the protein maintains its native conformation. However, when present within the solvent-inaccessible core, substantial structural rearrangement generally must occur to permit accessibility and reactivity. Conversely, the formation of a disulfide adduct involving a buried cysteine is typically structurally incompatible with the native conformation and results in misfolded forms of the protein that may promote aggregation and increased immunogenicity.

An analysis of a set of 131 non-homologous single-domain protein X-ray structures (1.95 Å resolution or better) has shown that the prevalence of free-cysteine residues in proteins is about 0.5% (i.e., about one free-cysteine in an average size protein). Furthermore, 50% of these free-cysteines are buried within the protein interior. See, e.g., Petersen, M. T. N. et al., "Amino acid neighbours and detailed conformational analysis of cysteines in proteins," *Protein Engineering* 12:535-548 (1999), the entire contents and disclosure of which are hereby incorporated by reference. Thus, although potentially highly-problematic for protein therapeutic application, the presence of buried free-cysteines in proteins is a surprisingly common occurrence. Examples of potentially therapeutic proteins having buried free cysteines include fibroblast growth factors, interleukin-2, β-interferon, granulocyte colony stimulating factor, and insulin-like growth factor-binding protein-1 (with the majority of these being approved human therapeutics).

Due to the potential negative consequences to protein structure caused by thiol adduct formation of the buried free cysteines at positions 16 and/or 83 and/or the partially accessible free cysteine at position 117 of human FGF-1 (based on the 140 amino acid numbering scheme), mutation to eliminate one or more of these free cysteine residues has been shown to produce a notable increase in the functional half-life of FGF-1 protein. See, e.g., Culajay, J. F. et al., "Thermodynamic characterization of mutants of human fibroblast growth factor 1 with an increased physiological half-life," *Biochemistry* 39:7153-7158 (2000); Ortega, S. et al. (1991), supra; Lee, J. et al., "The interaction between thermostability and buried free cysteines in regulating the functional half-life of fibroblast growth factor-1," *J. Mol. Biol.* 393:113-127 (2009); Cuevas, P. et al., "Hypotensive activity of fibroblast growth factor." *Science* 254:1208-10 (1991); and U.S. Pat. No. 5,409,897 (Thomas et al.; issued Apr. 25, 1995), the entire contents and disclosures of which are hereby incorporated by reference.

The 22 members of the mouse/human FGF family of proteins contain a conserved cysteine residue at position 83 (using the 140 amino acid numbering scheme for human FGF-1). Sequence and available structural information suggests that this position is a free cysteine in 16 members including the FGF-1 family, such as FGF-1 and FGF-2, but participates as a half-cystine (i.e., in a disulfide bond) in at least 3 members (and possibly as many as 6). For example, position 66 (using the same 140 amino acid numbering scheme) is a cysteine residue at corresponding positions of FGF-8, 19 and 23 and has been shown to form a half-cystine with the cysteine at a position corresponding to position 83 of FGF-1.

According to embodiments of the present invention, a previously unreported mutation of alanine (Ala) at position 66 of human FGF-1 (using the 140 amino acid numbering scheme for human FGF-1) or a corresponding position of a protein encoded by a Fgf-1 subfamily member to cysteine (Cys) is provided to encourage formation of a disulfide bond with the cysteine at a position corresponding to position 83 of human FGF-1. In contrast to previous reports of stabilization of FGF proteins achieved with removal of buried free cysteine residues, replacement of the alanine at position 66 of FGF-1 with a cysteine by mutation is shown (in greater detail below) to increase the stability of FGF-1 protein under oxidizing conditions despite some strain in protein structure to accommodate the mutation. Based on these results, the absence of a cysteine residue at position 66 of some wild-type FGF proteins may ensure that the cysteine residue at position 83 remains a free cysteine that functions as a buried reactive thiol to regulate (i.e., reduce) the functional half-life of the protein. Limiting the functional half-life of FGF proteins by maintaining a free cysteine at position 83 may be important for some FGF proteins considering that FGF proteins are generally potent mitogens. Thus, mutation of alanine at position 66 of human FGF-1 (or mutation at a position of other FGF proteins corresponding to position 66 of human FGF-1) to cysteine is provided herein as a way to increase the functional half-life of FGF proteins generally for improved pharmaceutical or therapeutic application.

Despite its similarity to other FGF proteins, it is somewhat surprising that mutation of alanine at position 66 of human FGF-1 to cysteine would result in a net stabilization of the protein. Replacement of alanine at position 66 with cysteine is divergent from the wild-type human FGF-1, and random mutations are generally more likely to destabilize rather than stabilize protein structure. In fact, the Ala66→Cys mutation is itself destabilizing by about 5.1 kJ/mol under reducing conditions when the cysteine is a free cysteine, but the mutation appears to only provide net stabilization under oxidizing conditions (by about 13.6 kJ/mol) upon formation of a disulfide bond. Given that there are other structural and amino acid differences among FGF members, it cannot be assumed that a net stabilizing disulfide bond would necessarily form with mutation of Ala at position 66 of FGF-1. Thus, it is not expected necessarily that the Ala66→Cys mutation would result in two cysteine residues that are ideally juxtaposed to form a net stabilizing disulfide bond. In fact, a software program (Disulfide by Design, Version 1.2) designed to predict whether the creation of a cysteine residue at specific positions within a protein might create novel disulfide bonds did not identify positions 66 and 83 of human FGF-1 as candidates.

Furthermore, mutation of alanine at position 66 of human FGF-1 to cysteine is in contrast to the teachings of U.S. Pat. No. 5,409,897 (Thomas et al.; issued Apr. 25, 1995). The '897 Thomas patent describes the removal of free cysteines of FGF-1 by mutation at positions 16, 83, and 117 to eliminate their thiol reactivity, whereas embodiments of the present invention describe mutation of alanine at position 66 of human FGF-1 to create a cysteine residue at this position, which may contribute to an increased functional half-life of a mutant FGF protein by forming a disulfide bond with a cysteine partner. Thus, mutation of alanine at position 66 of human FGF-1 to cysteine requires the retention of a cysteine residue at position 83 to allow for disulfide bond formation in further contrast with the '897 Thomas patent. Such formation of a disulfide bond may increase the thermostability of the protein while simultaneously eliminating thiol reactivity of the free cysteine at position 83.

According to embodiments of the present invention, mutations may be introduced into a FGF protein, such as FGF-1 or FGF-2, to sufficiently increase the thermodynamic stability of the protein to avoid any need for the use of heparin. According to embodiments of the present invention, mutations may be introduced into the interior or core of a FGF protein, such as FGF-1 or FGF-2, to increase thermodynamic stability, such that structural changes may be accommodated within the protein interior without any significant structural change to the surface of the protein that might otherwise trigger immunogenicity. Greater thermostability of FGF proteins may be achieved by introducing mutations within the solvent-excluded interior of the protein that eliminate or improve upon packing defects within the wild-type structure. Significant stability gains may be realized using this strategy, and these increases in thermostability may be achieved with minimal perturbation of the overall wild-type FGF protein structure, including surface features and solvent structure. Such mutations provide a protein design strategy whereby functional half-life may be manipulated while minimizing immunogenic potential or need for the use of heparin.

Human FGF-1 has a β-trefoil tertiary structure with a pseudo-threefold β-barrel axis of symmetry composed of antiparallel β strands around a hydrophobic core. Mutations have been made to core packing residues of human FGF-1 protein to study the effects of increased symmetry between core packing residues of the three structural units. Several of these core packing mutations may increase the thermodynamic stability of human FGF-1 protein, such as by reducing microcavities within the core of the protein. For example, the following mutations have been made to the core region of human FGF-1 with varying effects on stability (positions refer to those within human FGF-1 using the 140 amino acid numbering scheme): Leu44→Phe; Met67→Ile; Leu73→Val; Val109→Leu; Leu111→Ile; Cys117→Val; and combinations thereof. Some examples of mutant combinations that have also have been made include: Sym 2) Leu73→Val+Val109→Leu; Sym 3) Leu44→Phe+Leu73→Val+Val109→Leu; Sym 4) Leu44→Phe+Leu73→Val+Val109→Leu+Cys117→Val; Sym 5) Leu44→Phe+Leu73→Val+Val109→Leu+Leu111→Ile+Cys117→Val; and Sym 6) Leu44→Phe+Met67→Ile+Leu73→Val+Val109→Leu+Leu111→Ile+Cys117→Val. See, e.g., Brych S. R., et al., "Structure and stability effects of mutations designed to increase the primary sequence symmetry within the core region of a β-trefoil," *Protein Science* 10:2587-2599 (2001); and Brych S. R., et al., "Accommodation of a highly symmetric protein superfold," *Protein Science* 12:2704-2718 (2003), the entire contents and disclosures of which are hereby incorporated by reference.

However, the Met at position 67 appears highly intolerant to substitution in the Sym6 mutant and exhibited precipitation during purification. Separately, it is believed that the instability with mutation at position 67 is the result of two apparent insertions of adjacent loops involving amino acids 104-106 and 120-122 that distort the tertiary structure of FGF-1. Therefore, deleting these insertions might impart greater stability. Indeed, combining the Sym6 mutant above with deletions of amino acid positions 104-106 and 120-122 along with Ala103→Gly and Arg119→Gly mutations Sym6ΔΔ) resulted in a FGF-1 protein having greater stability and mitogenic activity than even wild-type FGF-1. See, e.g., Brych, S. R. et al., "Symmetric Primary and Tertiary Structure Mutations within a Symmetric Superfold: A Solution, not a Constraint, to Achieve a Foldable Polypeptide," *J. Mol. Biol.* 344:769-780 (2004), the entire contents and disclosure of which are hereby incorporated by reference.

Other mutational approaches have been taken to increase the stability of FGF-1 protein. In addition to the core packing residues, there are symmetrically related pairs of buried hydrophobic residues in FGF protein (termed "mini-cores") that are not part of the central core. In human FGF-1, these include symmetry related positions 22, 64, and 108 and symmetry related positions 42, 83, and 130 (positions refer to those within human FGF-1 using the 140 amino acid numbering scheme). For example, the following mutations have been made to the mini-core regions of human FGF-1 with varying effects on stability (positions refer to those within human FGF-1 using the 140 amino acid numbering scheme): Ile42→Cys; Cys83→Ile; Ile130→Cys; Phe22→Tyr; Tyr64→Phe; and Phe108→Tyr, and combinations thereof. See, e.g., Dubey, V. K., et al., "Redesigning symmetry-related "mini-core" regions of FGF-1 to increase primary structure symmetry: Thermodynamic and functional consequences of structural symmetry," *Protein Science* 14:2315-2323 (2005), the entire contents and disclosure of which are hereby incorporated by reference.

The N-terminus and C-terminus of human FGF-1 are composed of β strands that hydrogen bond to one another between residues 13 through 17 and residues 131 through 135 (positions refer to those within human FGF-1 using the 140 amino acid numbering scheme). However, this region of human FGF-1 has two solvent-excluded microcavities that may destabilize the protein. To study the effects on stability, mutations have been made to lysine at position 12 and proline at position 134 of human FGF-1. For example, the following mutations have been made to human FGF-1 (using the 140 amino acid numbering scheme for human FGF-1): Lys12→Cys; Lys12→Thr; Lys12→Val; Pro134→Cys; Pro134→Thr; and Pro134→Val. In addition, the Lys12→Val and Pro134→Val mutations may be combined with symmetry related mutations (based on the three-fold pseudo-symmetry architecture of FGF-1) Asn95→Val (for Lys12→Val) and Leu46→Val and Glu87→Val (for Pro134→Val), and combinations thereof. These mutations generally increase the thermostability and mitogenicity of FGF-1 to varying degrees. See, e.g., Dubey, V. K. et al., "Spackling the Crack: Stabilizing Human Fibroblast Growth Factor-1 by Targeting the N and C terminus β-Strand Interactions," *J. Mol. Biol.* 371:256-268 (2007), the entire contents and disclosure of which are hereby incorporated by reference.

According to embodiments of the present invention, a previously unreported mutation of the core packing phenylalanine (Phe) at position 132 of human FGF-1 (using the 140 amino acid numbering scheme for human FGF-1) or a corresponding position of a protein encoded by a Fgf-1 subfamily member to tryptophan (Trp) is provided. Replacement of the phenylalanine (Phe) at position 132 of human FGF-1 with tryptophan (Trp) by mutation is shown (in greater detail below) to increase the stability of the FGF-1 protein.

Although the phenylalanine (Phe) at position 132 of human FGF-1 is a core packing residue which may be amenable to mutation, not all mutations that replace core packing residues of FGF-1 with other hydrophobic amino acids improve thermodynamic stability of FGF-1. There are many uncertainties that make prediction of stabilizing mutations within the core of FGF-1 difficult. With regard to the Phe132→Trp mutant, while both phenylalanine and tryptophan are large aromatic side chains that may be good choices to bury within the core of FGF-1, tryptophan is different from phenylalanine in that it has a hydrogen-bonding requirement with the hydrogen bound to the nitrogen of the five member indole ring acting as a hydrogen bond donor. On the surface of a protein, solvent molecules may act as hydrogen bond acceptors to partner with the NH donor of the indole ring. However, within the interior of the protein (as with Phe 132 of FGF-1), other structural portions of the protein must serve as the hydrogen bonding partner. Therefore, it cannot be assumed that there would be a hydrogen bonding acceptor that is already positioned and ideally juxtaposed to Phe 132 of FGF-1, such that the Phe132→Trp mutation may be accommodated with minimal structural strain. As it turns out, the lone pair of electrons on the oxygen of the main chain carbonyl group at position Val 109 is positioned to act as a hydrogen bond acceptor for the newly introduced Trp at position 132 of FGF-1.

Furthermore, the Trp residue introduced by mutation is larger than the Phe at position 132 of wild-type FGF-1, and thus it cannot be assumed that the protein environment would necessarily be able to accommodate the larger Trp while satisfying the additional hydrogen bonding requirements. For example, a symmetry-related Phe85→Trp mutation is accommodated with an actual loss of favorable van der Waals interactions. Thus, disruption of local van der Waals interactions to accommodate a larger aromatic mutant side chain may offset any gain from the additional buried area within the protein interior. In addition, Phe132 is one of only three residues that are known to be absolutely conserved among the 22 mouse/human FGF family members, which may suggest that FGF proteins would be intolerant to mutation at the Phe132 position, and large hydrophobic residues within the protein interior generally make a substantial contribution to protein stability.

However, according to X-ray structural data (see below), the Phe132→Trp mutation side chain partially fills two cavities located adjacent to positions 132 with minimal perturbation of the surrounding structure. Accordingly, the Phe132→Trp mutation is found to increase thermostability of FGF-1 presumably due to greater space filling within the core and accommodation of the hydrogen bonding requirements of Trp along with minimal perturbation of the protein structure. Thus, mutation of the phenylalanine at position 132 of human FGF-1 (or mutation at the corresponding position of other FGF proteins) to tryptophan is provided herein as a way to increase the stability and/or functional half-life of FGF proteins generally for improved pharmaceutical or therapeutic application.

Wild-type human FGF-1 may exist in multiple forms of varying length in vivo due to proteolytic processing. Human Fgf-1 mRNA encodes a 155 amino acid protein (SEQ ID NO: 2; see also FIG. 1). However, a 154 amino acid form of human FGF-1 (SEQ ID NO: 3) may be formed from the 155 amino acid form if the starting methionine is removed. (See underlined methionine in FIG. 1) In addition, the 140 amino acid form of wild-type human FGF-1 (SEQ ID NO: 1; see also FIG. 2) is formed in vivo by proteolytic processing of the longer forms of FGF-1 to remove the first 15 or 14 amino acids of the 155 amino acid or the 154 amino acid forms, respectively (see shaded sequence of FIG. 1).

According to a broad aspect of the present invention, a mutant fibroblast growth factor (FGF) protein is provided having a polypeptide sequence that is at least 90% identical to the polypeptide sequence of a mammalian FGF-1 subfamily protein, or a functional fragment thereof, wherein the alanine (Ala) at an amino acid position of the mutant FGF protein corresponding to amino acid position 66 of wild-type human FGF-1 (based on the 140 amino acid numbering scheme of human FGF-1) is replaced with cysteine (Cys).

According to embodiments of the present invention, a mutant fibroblast growth factor (FGF) protein is provided having a polypeptide sequence that is at least 90% identical to the 140 amino acid polypeptide sequence of wild-type human FGF-1 protein (SEQ ID NO: 1), or a functional fragment thereof, wherein the alanine (Ala) at an amino acid position of the mutant FGF protein corresponding to amino acid position 66 of wild-type human FGF-1 (based on the 140 amino acid numbering scheme of human FGF-1) is replaced with cysteine (Cys). Alternatively, a mutant fibroblast growth factor (FGF) protein is provided having a polypeptide sequence that is at least 95% identical to the 140 amino acid polypeptide sequence of wild-type human FGF-1 protein (SEQ ID NO: 1), or a functional fragment thereof, wherein the alanine (Ala) at an amino acid position of the mutant FGF protein corresponding to amino acid position 66 of wild-type human FGF-1 (based on the 140 amino acid numbering scheme of human FGF-1) is replaced with cysteine (Cys). For example, according to some embodiments, a mutant FGF protein may be SEQ ID NO: 5, or a functional fragment thereof.

According to some embodiments, a mutant fibroblast growth factor (FGF) protein is provided having a polypeptide sequence that is at least 90% identical to the 155 amino acid polypeptide sequence of wild-type human FGF-1 protein (SEQ ID NO: 2), or a functional fragment thereof, wherein the alanine (Ala) at a position of the mutant FGF protein corresponding to position 81 of wild-type human FGF-1 (based on the 155 amino acid numbering scheme of human FGF-1) is replaced with cysteine (Cys). According to some embodiments, the starting methionine of the 155 amino acid form of wild-type human FGF-1 may be absent in the mutant FGF protein. According to these embodiments, a mutant fibroblast growth factor (FGF) protein is provided having a polypeptide sequence that is at least 90% identical to the 154 amino acid polypeptide sequence of wild-type human FGF-1 protein (SEQ ID NO: 3), or a functional fragment thereof, wherein the alanine (Ala) at a position of the mutant FGF protein corresponding to position 80 of wild-type human FGF-1 (based on the 154 amino acid numbering scheme of human FGF-1) is replaced with cysteine (Cys).

According to some embodiments of the present invention, the Ala to Cys mutation or substitution at a position of the mutant FGF protein corresponding to position 66 of human FGF-1 (based on the 140 amino acid numbering scheme of human FGF-1) may be combined with one or more other known mutation(s), substitution(s), modification(s), deletion(s), etc. According to some embodiments, the Ala to Cys mutation or substitution at position 66 (based on the 140 amino acid numbering scheme of human FGF-1) may be combined with one or more mutation(s) or substitution(s) to replace one or both of the free Cys residues at positions 16 and 117 of wild-type human FGF-1 with a different amino acid, such as alanine (Ala), serine (Ser), threonine (Thr), valine (Val), or isoleucine (Ile), in the mutant FGF protein. Presumably, mutation of the Cys residue at position 83 would remove the benefit of the Ala66→Cys mutation/substitution in the mutant FGF-1 by eliminating its proposed cystine partner. According to similar alternative embodiments, a mutant FGF protein may include the same combinations of mutations at positions corresponding to positions Cys30, Ala80, and Cys131 (based on the 154 amino acid form of human FGF-1) or Cys31, Ala81, and Cys132 (based on the 155 amino acid form of human FGF-1). One skilled in the art would be able to determine the polypeptide sequences for mutant FGF proteins having each of these mutant combinations based on the disclosure provided herein.

According to some embodiments, the Ala to Cys mutation or substitution at a position of a mutant FGF protein corresponding to position 66 of human FGF-1 (based on the 140 amino acid numbering scheme of human FGF-1) may be combined with one or more mutation(s) or substitution(s) to replace core packing residue(s) to increase the thermodynamic stability of the mutant FGF protein. For example, the Ala to Cys mutation or substitution at position 66 (based on the 140 amino acid numbering scheme of human FGF-1) may be combined with one or more of the following mutations or substitutions of core packing residue(s): Leu44→Phe; Met67→Ile; Leu73→Val; Val109→Leu; Leu111→Ile; and/or Cys117→Val. For example, the Ala to Cys mutation or substitution at position 66 (based on the 140 amino acid numbering scheme of human FGF-1) may be combined with one or more of the mutations or substitutions of core packing residues, which may be combined with other stabilizing mutations, such as the following: Leu44→Phe+Ala66→Cys; Ala66→Cys+Leu73→Val+Val109→Leu; Leu44→Phe+Ala66→Cys+Leu73→Val+Val109→Leu; Leu44→Phe+Ala66→Cys+Leu73→Val+Val109→Leu+Cys117→Val; Leu44→Phe+Ala66→Cys+Leu73→Val+Val109→Leu+Leu111→Ile+Cys117→Val; Leu44→Phe+Ala66→Cys+Met67→Ile+Leu73→Val+Val109→Leu+Leu111→Ile+Cys117→Val; or Leu44→Phe+Ala66→Cys+Met67→Ile+Leu73→Val+Ala103→Gly+104-106 deletion+Val109→Leu+Leu111→Ile+Cys117→Val+Arg119→Gly+120-122 deletion. The same mutant combinations may be applied at corresponding positions of mutant FGF proteins having high percent identity with the 154 and 155 amino acid forms of human FGF-1. One skilled in the art would be able to determine the polypeptide sequences of these mutant FGF proteins based on the disclosure provided herein.

According to some embodiments, the Ala to Cys mutation or substitution at a position corresponding to position 66 of FGF-1 (based on the 140 amino acid numbering scheme of human FGF-1) may be combined with one or more mutation(s) or substitution(s) to replace "mini-core" residue(s) to increase the thermodynamic stability of the mutant FGF protein. The Ala to Cys mutation or substitution at position 66 (based on the 140 amino acid numbering scheme of human FGF-1) may be combined with one or more of the following mutation(s) or substitution(s) of "mini-core" residue(s): Ile42→Cys; Cys83→Ile; Ile130→Cys; Phe22→Tyr; Tyr64→Phe; and/or Phe108→Tyr. For example, the Ala to Cys mutation or substitution at position 66 (based on the 140 amino acid numbering scheme of human FGF-1) may be combined with one or more of the mutation(s) or substitution(s) of "mini-core" residue(s), such as the following: Phe22→Tyr+

Ala66→Cys+Phe108→Tyr; Ile42→Cys+Ala66→Cys+Ile130→Cys; or Phe22→Tyr+Ile42→Cys+Ala66→Cys+Phe108→Tyr+Ile130→Cys.

In addition, the Ala to Cys mutation or substitution at position 66 (based on the 140 amino acid numbering scheme of human FGF-1) may be combined with one or more of the mutation(s) or substitution(s) of "mini-core" residue(s) in further combination with core packing mutations, such as the following: Phe22→Tyr+Leu44→Phe+Ala66→Cys+Met67→Ile+Leu73→Val+Ala103→Gly+104-106 deletion+Phe108→Tyr+Val109→Leu+Leu111→Ile+Cys117→Val+Arg119→Gly+120-122 deletion; Ile42→Cys+Leu44→Phe+Ala66→Cys+Met67→Ile+Leu73→Val+Ala103→Gly+104-106 deletion+Val109→Leu+Leu111→Ile+Cys117→Val+Arg119→Gly+120-122 deletion+Ile130→Cys; or Phe22→Tyr+Ile42→Cys+Leu44→Phe+Ala66→Cys+Met67→Ile+Leu73→Val+Ala103→Gly+104-106 deletion+Phe108→Tyr+Val109→Leu+Leu111→Ile+Cys117→Val+Arg119→Gly+120-122 deletion+Ile130→Cys. The same mutant combinations may be made at corresponding positions of mutant FGF proteins having a similarly high percent identity (e.g., at least 90% identity) with the 154 and 155 amino acid forms of human FGF-1. One skilled in the art would be able to determine the polypeptide sequences of these mutant FGF proteins based on the disclosure provided herein.

According to some embodiments, the Ala to Cys mutation or substitution at a position corresponding to position 66 of human FGF-1 (based on the 140 amino acid numbering scheme of human FGF-1) may be combined with one or more mutation(s) or substitution(s) to replace one or more of N-terminal residues 13 through 17 and/or C-terminal residues 131 through 135 (using the 140 amino acid numbering scheme for human FGF-1) to increase the thermostability of the mutant FGF protein. The Ala to Cys mutation or substitution at position 66 (based on the 140 amino acid numbering scheme of human FGF-1) may be combined with one or more of the following mutation(s) or substitution(s) of these N-terminal and/or C-terminal residues: Lys12→Cys; Lys12→Thr; Lys12→Val; Leu46→Val; Glu87→Val; Asn95→Val; Pro134→Cys; Pro134→Thr; and/or Pro134→Val. For example, the Ala to Cys mutation or substitution at position 66 (based on the 140 amino acid numbering scheme of human FGF-1) may be combined with one or more of the mutation(s) or substitution(s) of N-terminal and/or C-terminal residue(s), which may be combined with mutations at symmetry related positions, such as the following: Lys12→Val+Ala66→Cys+Pro134→Val; Lys12→Val+Ala66→Cys+Asn95→Val; Leu46→Val+Ala66→Cys+Pro134→Val; Ala66→Cys+Glu87→Val+Pro134→Val; Leu46→Val+Ala66→Cys+Glu87→Val+Pro134→Val; or Lys12→Val+Leu46→Val+Ala66→Cys+Glu87→Val+Asn95→Val+Pro134→Val. The same mutant combinations may be applied at corresponding positions of mutant FGF proteins having a high percent identity (e.g., at least 90% identity) with the 154 and 155 amino acid forms of human FGF-1. One skilled in the art would be able to determine the polypeptide sequences of these mutant FGF proteins based on the disclosure provided herein.

According to some embodiments of the present invention, the Ala to Cys mutation or substitution at a position of the mutant FGF protein corresponding to position 66 of human FGF-1 (based on the 140 amino acid numbering scheme of human FGF-1) may be combined with two or more mutations or substitutions of different types. For example, the Ala to Cys mutation or substitution at a position of the mutant FGF protein corresponding to position 66 of human FGF-1 (based on the 140 amino acid numbering scheme of human FGF-1) may be combined with any combination of mutation or substitution of the following residue types: free cysteine residues, core packing residues, "mini-core" residues, and/or interacting N-terminal or C-terminal residues. Indeed, the Ala to Cys mutation or substitution at a position of the mutant FGF protein corresponding to position 66 of human FGF-1 (based on the 140 amino acid numbering scheme of human FGF-1) may be combined with any combination of mutation(s), modification(s), substitution(s), deletion(s), etc., known in the art or described herein.

According to another broad aspect of the present invention, a mutant fibroblast growth factor (FGF) protein is provided having a polypeptide sequence that is at least 90% identical to the polypeptide sequence of a mammalian FGF-1 subfamily protein, or a functional fragment thereof, wherein the phenylalanine (Phe) at an amino acid position of the mutant FGF protein corresponding to amino acid position 132 of wild-type human FGF-1 (based on the 140 amino acid numbering scheme of human FGF-1) is replaced with tryptophan (Trp).

According to some embodiments of the present invention, a mutant fibroblast growth factor (FGF) protein is provided having a polypeptide sequence that is at least 90% identical to the polypeptide sequence of the 140 amino acid polypeptide sequence of wild-type human FGF-1 protein (SEQ ID NO: 1) or a functional fragment thereof, wherein the phenylalanine (Phe) at an amino acid position of the mutant FGF protein corresponding to amino acid position 132 of wild-type human FGF-1 (based on the 140 amino acid numbering scheme of human FGF-1) is replaced with tryptophan (Trp). Alternatively, a mutant fibroblast growth factor (FGF) protein is provided having a polypeptide sequence that is at least 95% identical to the 140 amino acid polypeptide sequence of wild-type human FGF-1 protein (SEQ ID NO: 1) or a functional fragment thereof, wherein the phenylalanine (Phe) at an amino acid position of the mutant FGF protein corresponding to amino acid position 132 of wild-type human FGF-1 (based on the 140 amino acid numbering scheme of human FGF-1) is replaced with tryptophan (Trp). For example, according to some embodiments, a mutant FGF protein may be SEQ ID NO: 7, or a functional fragment thereof.

According to some embodiments, a mutant fibroblast growth factor (FGF) protein is provided having a polypeptide sequence that is at least 90% identical to the 155 amino acid polypeptide sequence of wild-type human FGF-1 protein (SEQ ID NO: 2) or a functional fragment thereof, wherein the phenylalanine (Phe) at an amino acid position of the mutant FGF protein corresponding to amino acid position 147 of wild-type human FGF-1 (based on the 155 amino acid numbering scheme of human FGF-1) is replaced with tryptophan (Trp). According to some embodiments, the starting methionine of the 155 amino acid form of wild-type human FGF-1 may be absent from the mutant FGF protein. According to these embodiments, a mutant fibroblast growth factor (FGF) protein is provided having a polypeptide sequence that is at least 90% identical to the 154 amino acid polypeptide sequence of wild-type human FGF-1 protein (SEQ ID NO: 3) or a functional fragment thereof, wherein the phenylalanine (Phe) at an amino acid position of the mutant FGF protein corresponding to amino acid position 146 of wild-type human FGF-1 (based on the 154 amino acid numbering scheme of human FGF-1) is replaced with tryptophan (Trp).

According to some embodiments of the present invention, the Phe to Trp mutation or substitution at a position corresponding to position 132 of human FGF-1 (based on the 140 amino acid numbering scheme of human FGF-1) of the mutant FGF protein may be combined with one or more other known mutation(s), substitution(s), modification(s), deletion(s), etc. According to some embodiments, the Phe to Trp mutation or substitution at position 132 (based on the 140 amino acid numbering scheme of human FGF-1) may be combined with one or more mutation(s) or substitution(s) to replace one or both of the free Cys residues at positions 16, 83, and 117 of wild-type human FGF-1 with a different amino acid, such as alanine (Ala), serine (Ser), threonine (Thr), valine (Val), or isoleucine (Ile), in the mutant FGF protein. According to similar embodiments, a mutant FGF protein may include the same combinations of mutations at positions corresponding to positions Cys30, Cys97, Cys131, and Phe146 (based on the 154 amino acid form of human FGF-1) or Cys31, Cys98, Cys132, and Phe147 (based on the 155 amino acid form of human FGF-1). One skilled in the art would be able to determine the polypeptide sequences for mutant FGF proteins having each of these mutant combinations based on the disclosure provided herein.

According to some embodiments, the Phe to Trp mutation or substitution at a position corresponding to position 132 of human FGF-1 (based on the 140 amino acid numbering scheme of human FGF-1) may be combined with one or more mutation(s) or substitution(s) to replace core packing residue(s) to increase the thermodynamic stability of the mutant FGF protein. For example, the Phe to Trp mutation or substitution at position 132 (based on the 140 amino acid numbering scheme of human FGF-1) may be combined with one or more of the following mutations or substitutions of core packing residue(s): Leu44→Phe; Met67→Ile; Leu73→Val; Val109→Leu; Leu111→Ile; and/or Cys117→Val. For example, the Phe to Trp mutation or substitution at position 132 (based on the 140 amino acid numbering scheme of human FGF-1) may be combined with one or more of the mutations or substitutions of core packing residues, which may be combined with other stabilizing mutations, such as the following: Leu44→Phe+Phe132→Trp; Leu73→Val+Val109→Leu+Phe132→Trp; Leu44→Phe+Leu73→Val+Val109→Leu+Phe132→Trp; Leu44→Phe+Leu73→Val+Val109→Leu+Cys117→Val+Phe132→Trp; Leu44→Phe+Leu73→Val+Val109→Leu+Leu111→Ile+Cys117→Val+Phe132→Trp; Leu44→Phe+Met67→Ile+Leu73→Val+Val109→Leu+Leu111→Ile+Cys117→Val+Phe132→Trp; or Leu44→Phe+Met67→Ile+Leu73→Val+Ala103→Gly+104-106 deletion+Val109→Leu+Leu111→Ile+Cys117→Val+Arg119→Gly+120-122 deletion+Phe132→Trp. The same mutant combinations may be made at corresponding positions of mutant FGF proteins having high percent identity with the 154 and 155 amino acid forms of human FGF-1. One skilled in the art would be able to determine the polypeptide sequences of these mutant FGF proteins based on the disclosure provided herein.

According to some embodiments, the Phe to Trp mutation or substitution at a position corresponding to position 132 of human FGF-1 (based on the 140 amino acid numbering scheme of human FGF-1) may be combined with one or more mutation(s) or substitution(s) to replace "mini-core" residue(s) to increase the thermodynamic stability of the mutant FGF protein. For example, the Phe to Trp mutation or substitution at position 132 (based on the 140 amino acid numbering scheme of human FGF-1) may be combined with one or more of the following mutation(s) or substitution(s) of "mini-core" residue(s): Ile42→Cys; Cys83→Ile; Ile130→Cys; Phe22→Tyr; Tyr64→Phe; and/or Phe108→Tyr. For example, the Phe to Trp mutation or substitution at position 132 (based on the 140 amino acid numbering scheme of human FGF-1) may be combined with one or more of the mutation(s) or substitution(s) of "mini-core" residue(s), such as the following: Phe22→Tyr+Phe108→Tyr+Phe132→Trp; Ile42→Cys+Ile130→Cys+Phe132→Trp; or Phe22→Tyr+Ile42→Cys+Phe108→Tyr+Ile130→Cys+Phe132→Trp. In addition, the Phe to Trp mutation or substitution at position 132 (based on the 140 amino acid numbering scheme of human FGF-1) may be combined with one or more of the mutation(s) or substitution(s) of "mini-core" residue(s) in further combination with core packing mutations, such as the following: Phe22→Tyr+Leu44→Phe+Met67→Ile+Leu73→Val+Ala103→Gly+104-106 deletion+Phe108→Tyr+Val109→Leu+Leu111→Ile+Cys117→Val+Arg19→Gly+120-122 deletion+Phe132→Trp; Ile42→Cys+Leu44→Phe+Met67→Ile+Leu73→Val+Ala103→Gly+104-106 deletion+Val109→Leu+Leu111→Ile+Cys117→Val+Arg119→Gly+120-122 deletion+Ile130→Cys+Phe132→Trp; or Phe22→Tyr+Ile42→Cys+Leu44→Phe+Met67→Ile+Leu73→Val+Ala103→Gly+104-106 deletion+Phe108→Tyr+Val109→Leu+Leu111→Ile+Cys117→Val+Arg119→Gly+120-122 deletion+Ile130→Cys+Phe132→Trp. The same mutant combinations may be made at corresponding positions of mutant FGF proteins having high percent identity with the 154 and 155 amino acid forms of human FGF-1. One skilled in the art would be able to determine the polypeptide sequences of these mutant FGF proteins based on the disclosure provided herein.

According to some embodiments, the Phe to Trp mutation or substitution at a position corresponding to position 132 of human FGF-1 (based on the 140 amino acid numbering scheme of human FGF-1) may be combined with one or more mutation(s) or substitution(s) to replace one or more interacting N-terminal residues 13 through 17 and/or C-terminal residues 131 through 135 (using the 140 amino acid numbering scheme for human FGF-1) to increase the thermostability of the mutant FGF protein. For example, the Phe to Trp mutation or substitution at position 132 (based on the 140 amino acid numbering scheme of human FGF-1) may be combined with one or more of the following mutation(s) or substitution(s) of these N-terminal and/or C-terminal residues: Lys12→Cys; Lys12→Thr; Lys12→Val; Leu46→Val; Glu87→Val; Asn95→Val; Pro134→Cys; Pro134→Thr; and/or Pro134→Val. For example, the Phe to Trp mutation or substitution at position 132 (based on the 140 amino acid numbering scheme of human FGF-1) may be combined with one or more of the mutation(s) or substitution(s) of N-terminal and/or C-terminal residue(s), which may be combined with mutations at symmetry related positions, such as the following: Lys12→Val+Phe132→Trp+Pro134→Val; Lys12→Val+Asn95→Val+Phe132→Trp; Leu46→Val+Phe132→Trp+Pro134→Val; Glu87→Val+Phe132→Trp+Pro134→Val; Leu46→Val+Glu87→Val+Phe132→Trp+Pro134→Val; or Lys12→Val+Leu46→Val+Glu87→Val+Asn95→Val+Phe132→Trp+Pro134→Val. The same mutant combinations may be made at corresponding positions of mutant FGF proteins having high percent identity with the 154 and 155 amino acid forms of human FGF-1. One skilled in the art would be able to determine the polypeptide sequences of these mutant FGF proteins based on the disclosure provided herein.

According to some embodiments of the present invention, the Phe to Trp mutation or substitution at a position of the mutant FGF protein corresponding position 132 of human FGF-1 (based on the 140 amino acid numbering scheme of human FGF-1) may be combined with two or more mutations or substitutions of different types. For example, the Phe to Trp mutation or substitution at a position of the mutant FGF protein corresponding to position 132 of human FGF-1 (based on the 140 amino acid numbering scheme of human FGF-1) may be combined with any combination of mutation or substitution of the following residue types: free cysteine residues, core packing residues, "mini-core" residues, and/or interacting N-terminal or C-terminal residues. Indeed, the Phe to Trp mutation or substitution at a position of the mutant FGF protein corresponding to position 132 of human FGF-1 (based on the 140 amino acid numbering scheme of human FGF-1) may be combined with any combination of mutation(s), modification(s), substitution(s), deletion(s), etc., known in the art or described herein. For example, the following mutant combinations are provided according to some embodiments (based on the 140 amino acid numbering scheme of human FGF-1): Cys83→Thr+Cys117→Val+Phe132→Trp; Leu44→Phe+Cys83→Thr+Cys117→Val+Phe132→Trp; Lys12→Val+Cys117→Val+Phe132→Trp; or Lys12→Val+Cys83→Thr+Cys117→Val+Phe132→Trp.

According to some embodiments of the present invention, a mutant fibroblast growth factor (FGF) protein is provided having a polypeptide sequence that is at least 90% identical to the 140 amino acid polypeptide sequence of wild-type human FGF-1 protein (SEQ ID NO: 1) or a functional fragment thereof, wherein the phenylalanine (Phe) at an amino acid position of the mutant FGF protein corresponding to amino acid position 132 of wild-type human FGF-1 is replaced with tryptophan (Trp), and wherein the alanine (Ala) at an amino acid position of the mutant FGF protein corresponding to amino acid position 66 of wild-type human FGF-1 is replaced with cysteine (Cys) with amino acid positions based on the 140 amino acid numbering scheme of human FGF-1. For example, a mutant FGF protein may have the polypeptide sequence of SEQ ID NO: 9, or a functional fragment thereof. According to some of these embodiments, a mutant FGF protein having mutations or substitutions corresponding to both Ala66→Cys and Phe132→Trp may also have any combination of one or more other mutation(s), modification(s), substitution(s), deletion(s), etc. known in the art or described herein, such as mutation(s) or substitution(s) of one or more free cysteine residues, core packing residues, "mini-core" residues, and/or interacting N-terminal or C-terminal residues.

Most FGFs mediate their biological responses as extracellular proteins by binding to and activating cell surface tyrosine kinase FGF receptors (FGFRs). Four Fgfr genes, Fgfr1 through Fgfr4, have been identified in humans and mice, and these may be alternatively spliced to produce a greater number of FGFR isoforms. Except for FGF-11 through FGF-14, FGF-15/19, FGF-21, and FGF-23, other FGFs activate FGFRs with high affinity and with different degrees of specificity. See, e.g., Itoh, N. et al. (2008), supra. FGF-1 is the only known wild-type mouse/human FGF protein that is believed to bind to all FGFR types, but other FGF proteins have been shown to bind to multiple FGFRs. See, e.g., Zhang, X. et al., "Receptor Specificity of the Fibroblast Growth Factor Family," J Biol Chem 281(23): 15694-15700 (2006); and Szlachcic et al. (2009), supra, the entire contents and disclosure of which are hereby incorporated by reference. Therefore, a mutant FGF protein according to embodiments of the present invention may bind with specificity and affinity to at least one FGFR present on the surface of a cell, such as a fibroblast cell, neuronal or neuroblast cell, endothelial cell, chondrocyte, osteoblast, myoblast, smooth muscle cell, or glial cell. A mutant FGF protein according to embodiments of the present invention may also trigger growth, proliferation, and/or survival of cells, such as fibroblast cells, neuronal or neuroblast cells, endothelial cells, chondrocytes, osteoblasts, myoblasts, smooth muscle cells, glial cells, etc., known to express one or more FGFRs. This may occur through binding and activation of a FGF receptor and downstream signaling within the cell.

Both FGF-1 and FGF-2 are members of the Fgf-1 or FGF A subfamily and therefore are more related to each other than any other FGF protein. Human Fgf-2 mRNA encodes a 155 amino acid protein (SEQ ID NO: 4). (See FIG. 4) Although FGF-1 is the only FGF protein that has been shown to bind all FGF receptor types, FGF-2 also binds multiple FGF receptor types and may have therapeutic benefits. Therefore, according to another broad aspect of the present invention, a mutant FGF protein is provided having a polypeptide sequence that is at least 90% identical to the 155 amino acid polypeptide sequence of wild-type human FGF-2 protein (SEQ ID NO: 4), or a functional fragment thereof, and having one or more corresponding mutations described above for FGF-1.

According to some embodiments, a mutant fibroblast growth factor (FGF) protein is provided having a polypeptide sequence that is at least 90% identical to the 155 amino acid polypeptide sequence of wild-type human FGF-2 protein (SEQ ID NO: 4), or a functional fragment thereof, wherein the alanine (Ala) at an amino acid position of the mutant FGF protein corresponding to amino acid position 84 of wild-type human FGF-2 is replaced with cysteine (Cys). Alternatively, a mutant fibroblast growth factor (FGF) protein is provided having a polypeptide sequence that is at least 95% identical to the 155 amino acid polypeptide sequence of wild-type human FGF-2 protein (SEQ ID NO: 4), or a functional fragment thereof, wherein the alanine (Ala) at an amino acid position of the mutant FGF protein corresponding to amino acid position 84 of wild-type human FGF-2 is replaced with cysteine (Cys). For example, according to some embodiments, a mutant FGF protein may be SEQ ID NO: 6 or a functional fragment thereof.

According to some embodiments, a mutant fibroblast growth factor (FGF) protein is provided having a polypeptide sequence that is at least 90% identical to the 155 amino acid polypeptide sequence of wild-type human FGF-2 protein (SEQ ID NO: 4), or a functional fragment thereof, wherein the phenylalanine (Phe) at an amino acid position of the mutant FGF protein corresponding to amino acid position 148 of wild-type human FGF-2 is replaced with tryptophan (Trp). Alternatively, a mutant fibroblast growth factor (FGF) protein is provided having a polypeptide sequence that is at least 95% identical to the 155 amino acid polypeptide sequence of wild-type human FGF-2 protein (SEQ ID NO: 4), or a functional fragment thereof, wherein the phenylalanine (Phe) at an amino acid position of the mutant FGF protein corresponding to amino acid position 148 of wild-type human FGF-2 is replaced with tryptophan (Trp). For example, according to some embodiments, a mutant FGF protein may be SEQ ID NO: 8 or a functional fragment thereof.

According to some embodiments of the present invention, a mutant FGF protein having either the alanine (Ala) to cysteine (Cys) mutation or substitution at an amino acid position of the mutant FGF protein corresponding to amino acid position 84 of the 155 amino acid wild-type human FGF-2 (SEQ ID NO: 4), or the phenylalanine (Phe) to tryptophan (Trp) mutation or substitution corresponding to amino acid position 148 of the 155 amino acid wild-type human FGF-2 (SEQ ID NO: 4) may be combined with one or more other known mutation(s), substitution(s), modification(s), deletion(s), etc. described herein or known in the art, such as mutation(s) or substitution(s) of one or more free cysteine residues, core packing residues, "mini-core" residues, and/or interacting N-terminal or C-terminal residues.

According to some embodiments, a mutant fibroblast growth factor (FGF) protein is provided having a polypeptide sequence that is at least 90% identical to the 155 amino acid polypeptide sequence of wild-type human FGF-2 protein (SEQ ID NO: 4), or a functional fragment thereof, wherein the alanine (Ala) at an amino acid position of the mutant FGF protein corresponding to amino acid position 84 of wild-type human FGF-2 is replaced with cysteine (Cys), and wherein the phenylalanine (Phe) at an amino acid position of the mutant FGF protein corresponding to amino acid position 148 of wild-type human FGF-2 is replaced with tryptophan (Trp). For example, a mutant FGF protein may have the polypeptide sequence of SEQ ID NO: 10, or a functional fragment thereof.

As stated above, both FGF-1 and FGF-2 are members of the Fgf-1 or FGF A subfamily and are therefore more related to each other than any other FGF protein. Sequence analysis shows that members of different FGF subfamilies share roughly 15% to 71% amino acid identity, while orthologous FGF proteins (i.e., members of the same subfamily from different species) have higher sequence identity. See, e.g., Ornitz et al. (2001), supra; and Itoh et al. (2008), supra. In addition to the wild-type sequences for human FGF-1 and FGF-2 proteins, the wild-type polypeptide sequences of mouse FGF-1 protein (see FIG. 3; SEQ ID NO: 11) and mouse FGF-2 protein (see FIG. 5; SEQ ID NO: 12) are also provided. Therefore, a mutant FGF protein according to embodiments of the present invention having at least 90% or 95% identity to the wild-type polypeptide sequence of one of the human FGF-1 protein forms is unlikely to include proteins other than those resembling FGF-1 since members of other FGF subfamilies generally have much lower sequence identity. Similarly, a mutant FGF protein according to embodiments of the present invention having at least 90% or 95% identity to the wild-type polypeptide sequence human FGF-2 is unlikely to include proteins other than those resembling FGF-2 since members of other FGF subfamilies generally have much lower sequence identity.

According to some embodiments of the present invention, the mutant FGF protein retains the ability to bind with specificity and affinity to a FGF receptor (FGFR) and trigger growth, proliferation, and/or survival of cultured and/or in vivo cells relative to untreated control cells (i.e., cells that are not exposed to a mutant FGF protein). Such cells may include, for example, fibroblast cells, neuronal or neuroblast cells, endothelial cells, chondrocytes, osteoblasts, myoblasts, smooth muscle cells, glial cells, etc., of human or animal origin known in the art to express one or more FGFRs or to respond to FGF proteins. See, e.g., Esch, F. et al., "Primary structure of bovine pituitary basic fibroblast growth factor (FGF) and comparison with the amino-terminal sequence of bovine brain acidic FGF," *PNAS USA* 82(19):6507-11 (1985); and Gensburger, C. et al., "Effect of basic FGF on the proliferation of rat neuroblasts in culture," *C R Acad Sci III* 303(11):465-468 (1986). Such a trigger of growth, proliferation, and/or survival of these cultured or in vivo cells may occur through binding and activation of a FGF receptor and downstream signaling within the cell(s). According to some embodiments, the mutant FGF protein of the present invention has a greater thermodynamic stability than wild-type human FGF-1 or FGF-2. The mutant FGF protein of the present invention may have a greater thermodynamic stability than wild-type human FGF-1 or FGF-2 if the mutant FGF protein has a $\Delta G_{unfolding}$ value greater than that of wild-type human FGF-1 or FGF-2, such that $\Delta\Delta G = \Delta G_{unfolding}(\text{wild type}) - \Delta G_{unfolding}(\text{mutant}) < 0$, according to an isothermal equilibrium denaturation assay, differential scanning calorimetry assay, thermally-monitored spectroscopic assay, or other method of quantitation of $\Delta G_{unfolding}$ known in the art. According to some embodiments, the mutant FGF protein of the present invention has a greater functional half-life than wild-type human FGF-1 or FGF-2 according to a cultured fibroblast proliferation assay. According to some embodiments, the mutant FGF protein of the present invention has essentially unaltered surface features relative to the wild type FGF protein and therefore has little or no immunogenic potential (i.e., the mutant FGF protein does not cause a significant immune reaction when introduced or administered to the body of an individual, subject, or patient).

According to some embodiments of the present invention, a functional fragment of a mutant FGF protein is also provided, such as a functional fragment of a polypeptide sequence having at least 90% or 95% identity to at least a portion of the wild-type polypeptide sequence of one of the human FGF-1 protein forms or to at least a portion of the wild-type polypeptide sequence of human FGF-2 protein. A functional fragment may be defined as a portion or fragment of a mutant FGF protein that retains FGF-like function. For example, a functional fragment may be a portion or fragment of a mutant FGF protein that is able to bind with specificity and affinity to at least one FGF receptor (FGFR) present on the surface of a cell. A functional fragment may also be a portion or fragment of a mutant FGF protein that is able to trigger growth, proliferation, and/or survival of cultured and/or in vivo cells relative to untreated control cells (i.e., cells that are not exposed to a mutant FGF protein). Such cells may include, for example, fibroblast cells, neuronal or neuroblast cells, endothelial cells, chondrocytes, osteoblasts, myoblasts, smooth muscle cells, glial cells, etc., of human or animal origin known in the art to express one or more FGFRs or respond to FGF proteins, which may occur through binding and activation of a FGF receptor and downstream signaling within the cell. The binding affinity and/or mitogenicity of a mutant FGF protein, or a functional fragment thereof, may be determined according to assays described herein or known in the art, such as a cultured fibroblast proliferation assay, etc.

According to some embodiments, a mutant FGF protein or a functional fragment thereof that is described herein may further include any additional non-FGF peptide sequence or tag known in the art, which may be used to facilitate its detection or purification. For example, a mutant FGF protein may contain any additional non-FGF peptide sequence known in the art that provides an epitope or fluorescence for detection, such as Myc, HA, His, FLAG, GST, GFP, etc., or provides a basis for purification by chromatography. According to some embodiments, a mutant FGF protein or a functional fragment thereof that is described herein may further include an additional non-FGF peptide sequence or tag known in the art for targeting the mutant FGF protein to a particular tissue or cell, improved solubility, sustained activity or stability, improved expression, etc.

According to another broad aspect of the present invention, a polynucleotide sequence encoding a mutant FGF protein, or a functional fragment thereof, of the present invention as described herein is also provided. Wild-type genomic and cDNA polynucleotide sequences for Fgf family members are known in the art. One skilled in the art would be able to determine the polynucleotide sequences encoding the mutant FGF proteins of the present invention by mutating specific base pairs of codon(s) of the wild-type polynucleotide sequence encoding the mutated or substituted amino acids of the mutant FGF proteins. Such a polynucleotide sequence may be present in (i.e., inserted, introduced, or subcloned into) any vector or expression system known in the art, such as a polynucleotide sequence of a plasmid, artificial chromosome, virus, retrovirus, transposable element, etc. In addition, such a vector or expression system may be introduced into a host cell, such as a bacterial cell, yeast cell, insect cell, mammalian cell, etc., by transformation, transfection, infection, transduction, direct injection, etc., to allow for expression of the mutant FGF protein, or a functional fragment thereof, by the host cell. Alternatively, a mutant FGF protein, or a functional fragment thereof, may be synthesized from such a polynucleotide sequence in vitro. Examples of vectors and expression systems as well as host cells that may be used for protein expression are known in the art. See, e.g., U.S. Utility application Ser. No. 12/163,755, filed Jun. 27, 2008, the entire contents and disclosure of which are hereby incorporated by reference.

Since a mutant FGF protein, or a functional fragment thereof, according to some embodiments of the present invention, includes only polypeptide sequences containing one or more mutations relative to a wild-type FGF sequence, such a mutant FGF protein is not the naturally occurring wild-type polypeptide sequence for the FGF protein. Similarly, a polynucleotide sequence encoding a mutant FGF protein, or a functional fragment thereof, is not the naturally occurring polynucleotide sequence encoding the wild-type FGF protein. However, according to some embodiments, a mutant FGF protein, or a functional fragment thereof, or a polynucleotide encoding a mutant FGF protein, or a functional fragment thereof, may be isolated and/or purified from a cellular or tissue environment. For example, a mutant FGF protein, or a functional fragment thereof, may be isolated and/or purified from a cellular or tissue environment from which the mutant FGF protein, or a functional fragment thereof, is expressed.

According to embodiments of the present invention, novel mutant forms of FGF family proteins are provided having an increased thermodynamic stability and/or functional half-life. However, it is envisioned that other mutant forms of FGF family proteins, or a functional fragment thereof, having instead a decreased thermodynamic stability and/or functional half-life may be used, especially when a short half-life of activity and/or rapid clearance is preferred.

According to another broad aspect of the present invention, a mutant FGF protein, or a functional fragment thereof, may be formulated as part of a composition containing other components. According to some embodiments of the present invention, a pharmaceutical composition is provided comprising a mutant FGF protein, or a functional fragment thereof, in combination with a pharmaceutically acceptable carrier. Such a pharmaceutical composition may be administered to an individual, subject, or patient to promote vascularization, healing, proliferation, growth, or protection of cells, etc. According to some embodiments, a pharmaceutical composition is provided comprising a therapeutically effective amount of a mutant FGF protein, or a functional fragment thereof, in combination with a pharmaceutically acceptable carrier. According to some embodiments, for example, a pharmaceutical composition is provided comprising a mutant FGF protein, or a functional fragment thereof, together with other angiogenic factors known in the art or provided herein, such as vascular endothelial growth factor (VEGF), other wild-type and/or mutant FGF proteins, vasodilating molecules, etc., and a pharmaceutically acceptable carrier.

Examples of pharmaceutically acceptable carriers and other suitable additives and adjuvants for pharmaceutical compositions that may be used in combination with embodiments of the compounds or compositions of the present invention for administration to an individual, subject, or patient include those known to those skilled in the pharmacological or pharmaceutical arts for use with protein-based biopharmaceuticals. As used herein, the pharmaceutically acceptable carriers may be either liquid or solid and may include solvents, buffers, dispersion media, oils, coatings, surfactants, antioxidants, preservatives (e.g., antibacterial agents, antifungal agents, etc.), isotonic agents, absorption delaying agents, proteins and low molecular weight polypeptides, hydrophilic polymers, amino acids, carbohydrates, sugar alcohols, metal ions, salts, preservatives, stabilizers, gels, binders, excipients, fillers, diluents, solubilizers, disintegration agents, lubricants, surfactants, penetrants, chelating agents, sweetening agents, flavoring agents, dyes, glidants, wetting agents, bulking agents, thickening agents, etc., and combinations thereof. Examples of pharmaceutically acceptable carriers may include, for example, substances for modifying or maintaining the pH, osmolarity, viscosity, clarity, color, sterility, stability, rate of dissolution, rate of diffusion, odor of the formulation, etc. Since compositions of the present invention comprise a mutant FGF protein, pharmaceutical compositions may be formulated to include substances that may inhibit or avoid proteolytic degradation.

According to some embodiments of present compositions, the exact formulation, route of administration, and dosage of the present compositions comprising a mutant FGF protein may be chosen according to the judgment of a skilled scientist, veterinarian, or physician in view of the characteristics and conditions of an individual, subject or patient to be treated. Proper formulation and choice of pharmaceutically acceptable carriers for a pharmaceutical composition may also be dependent upon the route and method of administration. Accordingly, there is a wide variety of suitable formulations for pharmaceutical compositions of the present invention. For a description of pharmaceutical compositions, carriers, formulations, methods and routes of administration, etc., that may be used for embodiments of compositions of the present invention, see, for example, Remington, *The Science and Practice of Pharmacy*, (University of the Sciences in Philadelphia, 21st ed., Lippincott Williams & Wilkins, 2005), the contents and disclosure of which are hereby incorporated by reference.

Except insofar as any conventional pharmaceutical carrier is incompatible with embodiments of the compositions of the present invention comprising a mutant FGF protein, their potential use in pharmaceutical compositions of the present invention is contemplated. Embodiments of the pharmaceutical compositions and formulations of the present invention may utilize different types of carriers depending on whether they are to be administered in solid, semi-solid, or liquid form and whether they need to be sterile for certain routes of administration, such as local or systemic injection or infusion.

Various delivery systems and reagents known in the art are also contemplated for use as carriers for embodiments of pharmaceutical compositions of the present invention comprising a mutant FGF protein. Where appropriate, such delivery systems or reagents may include, for example, liposomes, microparticles or nanoparticles, microcapsules, emulsions, polymers, etc., or any combination thereof. Liposomes may be coated, for example, with opsonization-inhibiting moieties or molecules (e.g., PEG) to avoid detection by the immune system and may be specifically formulated and/or associated with other molecules, antibodies, or conjugates to improve delivery, intake, and/or specificity into specific tissues or cells. See, e.g., Szoka et al., "Comparative properties and methods of preparation of lipid vesicles (liposomes)," *Ann. Rev. Biophys. Bioeng.*, 9:467 (1980); Immordino, M. L., "Stealth liposomes: review of the basic science, rationale, and clinical applications, existing and potential," *Int. J Nanomedicine* 1(3):297-315 (2006); Samad, A., "Liposomal Drug Delivery Systems: An Update Review," *Current Drug Delivery* 4(4): 297-305 (2007), the contents and disclosures of which are hereby incorporated by reference in their entirety.

Embodiments of compositions of the present invention may be formulated so as to provide rapid, sustained, or delayed release of a mutant FGF protein by embedding or soaking the mutant FGF protein in a matrix or network of polymeric material according to methods known in the art. Embodiments of these compositions may be formulated to restrict diffusion of a mutant FGF protein away from a location where the composition is intentionally administered or applied, such as by diffusion or by erosion or degradation of the network or matrix. For local administration of embodiments of compositions of the present invention, an advantage of providing sustained or restricted release is that a localized efficacious concentration of a mutant FGF protein may be achieved at a site of administration with relatively less mutant FGF protein and fewer applications or injections required. Such a restricted or sustained release composition may provide targeted delivery of a mutant FGF protein while minimizing undesired side effects that may result if the mutant FGF protein diffused away from the site of administration.

Embodiments of compositions of the present invention providing sustained or restricted release or diffusion of a mutant FGF protein may include a variety of biocompatible materials or polymers, such as poly(2-hydroxyethyl methacrylate), ethylene vinyl acetate or poly-D-(−)-3-hydroxybutyric acid, polylactides, polyglycolides, polylactide co-glycolide, polyanhydrides, poly(ortho)esters, polypeptides, hyaluronic acid, hydrogels, collagen, fibrin, alginate, chondroitin sulfate, carboxylic acids, fatty acids, phospholipids, polysaccharides, polynucleotides, polyvinyl propylene, polyvinylpyrrolidone, sulfated proteoglycans, dextrins, poloxamers, silicone, methylcellulose, and the like. Such compositions may comprise a semi-permeable polymer matrix or network, such as a gel, paste, putty, etc. According to some embodiments, compositions may be molded or formed into a desired shape, such as for placement or to fill a space at desired site of administration in the body of an individual, subject, or patient to promote vascularization, cellular proliferation, and/or healing, or to promote specific routes or tracks of novel vasculature.

According to some embodiments of the present invention, a pharmaceutical composition of the present invention comprising a mutant FGF protein may include a matrix or network containing one or more of the following: collagen, fibrin, fibrinogen, fibronectin, and/or alginate. For example, a pharmaceutical composition of the present invention comprising a mutant FGF protein may be formulated as a fibrin plug or fibrin glue. According to other embodiments, compositions of the present invention comprising a mutant FGF protein may be embedded or soaked into a medical or surgical device, such as a fabric, bandage, suture, sponge, etc. or other polymers, which may safely degrade over time.

The mode or route of administration for embodiments of compositions of the present invention comprising a mutant FGF protein may be selected to maximize delivery to a desired target site in the body of an individual, subject, or patient. Pharmaceutical compositions may be administered in a number of ways, including any suitable enteral, parenteral, topical, or local mode or route, depending on whether local or systemic treatment is preferred and/or the specific area to be treated. Suitable enteral routes for administration may include oral, rectal, intestinal, and gastric. Suitable parenteral routes may include intravascular routes, such as intravenous (bolus and infusion), intraarterial, and intracardiac; mucosal routes, such as transmucosal (e.g., insufflation), sublingual, buccal, intranasal, pulmonary (e.g., inhalation), and vaginal; intracranial (e.g., intracerebral); intraocular; intrathecal; intraperitoneal; subcutaneous; intramuscular; intradermal; subcutaneous; intramedullary; intraarticular; or intraosseus.

Embodiments of pharmaceutical compositions of the present invention may be administered in a variety of unit dosage forms depending on the method of administration. For example, unit dosage forms suitable for oral administration include solid dosage forms, such as powders, granules, tablets, pills, capsules, suppositories, depots, and dragees, and liquid dosage forms, such as elixirs, syrups, suspensions, sprays, gels, lotions, creams, slurries, foams, jellies, ointments, salves, solutions, suspensions, tinctures, and/or emulsions.

Embodiments of pharmaceutical compositions of the present invention may be administered either locally or systemically. However, polypeptides are generally less suitable for oral administration due to their susceptibility to digestion by gastric acids or intestinal enzymes. Although formulations may be designed to circumvent these problems, bioavailability is impaired due to poor gastrointestinal absorption. Therefore, preferred routes of administration generally include parenteral administration or local injection or topical application at or near a site of a disorder or disease, such as a site of ischemic or hypoxic stress or a site of an injury or wound.

Suitable routes for parenteral administration are described above. Embodiment of pharmaceutical compositions comprising a mutant FGF protein for parenteral administration may be formulated as solutions, emulsions, suspensions, or other liquids, such as saline, dextrose solution, glycerol, and the like, which may be sterile and/or isotonic. However, a suitable carrier for parenteral administration may include aqueous or non-aqueous (e.g., oily) solvents. Suitable formulations for parenteral administration may be in unit-dose or multi-dose sealed containers, such as ampoules, vials, bags, etc. A mutant FGF protein of the present invention may be administered by continuous infusion (e.g., minipumps, osmotic pumps, etc.), single bolus, or slow-release depot formulations, etc. Solutions and suspensions for parenteral administration may be freshly prepared or resuspended from a dry preparation of a mutant FGF protein, such as a lyophilized or spray dried preparation, prior to its use.

In addition to parenteral modes of administration, embodiments of pharmaceutical compositions comprising a mutant FGF protein may be administered by local injection, placement, catheter delivery, or implantation at a desired site of action in the body of an individual, subject, or patient, such as a tissue or cellular environment at or near a site of a disorder or disease, such as at or near a site of ischemic or hypoxic stress or a site of an injury or wound. Alternatively, a pharmaceutical composition comprising a mutant FGF protein may be administered by local injection, placement, or implantation at or near a site causing an ischemic or hypoxic stress or condition at a different site, such as a site of vessel occlusion. Such a local injection, placement, or implantation of pharmaceutical compositions of the present invention may include any suitable peri- and intra-tissue injections, such as intradermal, intramuscular, intracardiac, subcutaneous, intrathecal, etc. as the case may be. Pharmaceutical compositions of the present invention may also be administered by local injection, placement, or implantation at two or more sites at or near a desired site of action.

For local injection, placement, or implantation, embodiments of pharmaceutical compositions of the present invention may be formulated with a variety of aqueous or non-aqueous solutions, suspensions, emulsions, etc. as described above, such as physiologically compatible buffers including Hank's solution, Ringer's solution, physiological saline buffer, etc. Embodiments of pharmaceutical compositions for local injection, placement, or implantation may also comprise biocompatible materials or polymers providing sustained release or restricted diffusion as described above. As with pharmaceutical compositions for parenteral administration, solutions and suspensions for local or topical administration may be freshly prepared or resuspended from a dry preparation of a mutant FGF protein, such as a lyophilized or spray dried preparation, prior to its use.

Embodiments of pharmaceutical compositions of the present invention may also be administered topically, such as at a site of a tissue injury or a wound. Embodiments of pharmaceutical compositions for topical administration may be formulated as a liquid or semi-solid material, such as a gel, paste, putty, ointment, cream, emulsion, patch, etc. as well as other biocompatible materials or polymers. However, embodiments of pharmaceutical compositions for topical administration may also be formulated as a dry or solid preparation, such as a powders, granules, etc., that may be applied directly to a desired site of action. According to some embodiments, pharmaceutical compositions for topical administration may be molded into a desired size and shape, such as for placement within or to fill a space at a desired site of administration in the body of an individual, subject, or patient, such as at a site of a tissue injury or wound to promote healing. Pharmaceutical compositions of the present invention may also be topically administered at two or more sites at or near a tissue injury or a wound.

Such embodiments of pharmaceutical compositions of the present invention comprising a mutant FGF protein for topical or local administration may comprise a semi-permeable polymer matrix or network, which may provide sustained release or restricted diffusion to localize the mutant FGF protein to the site of administration. According to some embodiments of the present invention, a pharmaceutical composition of the present invention comprising a mutant FGF protein for topical or local administration may include a matrix or network of fibrin and/or fibrinogen, such as a fibrin plug or fibrin glue.

Determination of a therapeutically effective amount of a mutant FGF protein, or a functional fragment thereof, may be carried out in a manner known to those skilled in the art depending on the conditions or exigencies of a given therapeutic situation. For example, a therapeutically effective amount may be determined by titration to optimize safety and effectiveness. Lower than expected dosages may be administered first to an individual, subject, or patient, and dosages may then be titrated upward until a therapeutically effective and safe concentration amount (or a potentially unsafe concentration or amount) is reached.

Appropriate dosage amounts for a mutant FGF protein may be determined or predicted from empirical evidence. Specific dosages may vary according to numerous factors and may be initially determined on the basis of in vitro, cell culture, and/or animal in vivo studies. Dosages or concentrations tested in vitro for mutant FGF proteins according to some embodiments of the present invention may provide useful guidance in determining therapeutically effective and appropriate amounts for in vivo administration. For example, a therapeutically effective dose of a mutant FGF protein may be estimated initially from a cell culture assay, for example, by measuring proliferation, growth, and/or survival of cultured cells or by the formation of vessels in culture in response to the mutant FGF protein depending on the intended therapeutic application. Such values may be used, for example, to translate into appropriate amounts for use in animal testing or for clinical trials in humans. Determining an appropriate dosage for composition according to embodiments of the present invention may be discerned from any or all information or data available from any assay or experiment performed.

Animal testing of predicted dosages may provide additional indication of proper dosages for other types of animals, including humans. For example, a dosage for a mutant FGF protein may be an amount that produces a localized or circulating concentration which roughly approximates concentrations shown to be effective according to cell culture and/or in vitro assays. Such an amount may be used initially to determine effectiveness and/or safety at such concentrations or to determine or extrapolate useful dosages for other animals, such as humans. Toxicity and therapeutic efficacy of a mutant FGF protein may be determined or predicted from any standard pharmaceutical procedures based on data from cell cultures or experimental animals. For example, an $LD_{50}$ value (i.e., dose lethal in 50% of the population) and an $ED_{50}$ value (the dose therapeutically effective in 50% of subjects according to clinical or pathological criteria) may be determined for a given animal test subject, and the ratio of $LD_{50}/ED_{50}$ may be expressed as a therapeutic index for a parenterally administered mutant FGF protein. Compounds that exhibit a high therapeutic index may indicate that higher concentrations of the mutant FGF protein are safe and non-toxic and/or that lower doses may be efficacious in an individual, subject, or patient. However, a lower therapeutic index might indicate that only lower (and perhaps ineffective) concentrations of the mutant FGF protein may be acceptable in terms of safety. Levels of mutant FGF protein in a tissue or plasma sample from an individual, subject, or patient may be measured or monitored by any known technique.

In most cases, an appropriate dosage amount may be a balance of factors including efficacy and safety. Factors considered in determining a dosage that is therapeutically effective and safe for an individual, subject, or patient in clinical settings will depend on many factors including the mode/route of administration, timing of administration, rate of excretion, target site, disease or physiological state, medical history, age, sex, physical characteristics, other medications, etc. This list of factors is illustrative and not exhaustive, and may include any or all factors which might be considered by a skilled scientist, veterinarian, or physician (as the case may be) in determining an appropriate treatment. A specific dosage amount of a mutant FGF protein administered to an individual, subject, or patient may be in a range equivalent to dosages used for other currently-used therapeutic proteins, adjusted for the altered activity, thermostability, or functional half-life of the particular mutant FGF protein.

For the purposes of the present invention, a therapeutically effective amount of a mutant FGF protein may refer to an amount effective to achieve a desired result, purpose, or therapeutic benefit, such as an amount effective to prevent, alleviate, ameliorate, treat, etc. the underlying causes and/or symptoms of a condition or disease, such as an ischemic or hypoxic condition or disease or a wound or tissue damage. According to some embodiments, a therapeutically effective amount of a mutant FGF protein may be an amount effective to increase blood flow, angiogenesis, and/or vascularization within or to a particular tissue or region of the body of an individual, subject, or patient, such as a tissue or region of the body experiencing ischemia and/or hypoxic conditions. Increased blood flow, angiogenesis, and/or vascularization within or to such a tissue or region of the body may be determined by a skilled scientist, veterinarian, or physician using any known reagents and pathological or clinical techniques, such as imaging techniques using a contrast dye to detect vasculature, reduction of clinical symptoms associated with an underlying ischemic or hypoxic condition or disease, etc. Where a mutant FGF protein is administered to cardiac tissue, a therapeutically effective amount may be an amount effective to reduce clinical symptoms of coronary artery disease, such as reduction in angina, breathlessness, leg swelling, heart or respiratory rates, edema, fatigue, weakness, etc., or to reduce the risk of a myocardial infarction. According to other embodiments, a therapeutically effective amount of a mutant FGF protein may be an amount effective to improve the quality and/or rate of healing or repair of a damaged tissue or wound according to known standards and knowledge generally available to a skilled scientist, veterinarian, or physician as the case may be.

Therapeutically effective amounts or dosages of a mutant FGF protein may include any dosage amounts, or approximations thereof, of a FGF protein previously used or contemplated for use in treatments or clinical trials, or extrapolated from dosage amounts used in experimental animals. For example, a therapeutically effective amount may be a dosage of about 0.01 mg per kg body weight. See, e.g., Schumacher, B. et al., "Induction of neoangiogenesis in ischemic myocardium by human growth factors: first clinical results of a new treatment of coronary heart disease," Circulation 97:645-650 (1998), the entire contents and disclosure of which is hereby incorporated by reference.

Embodiments of the compounds or compositions of the present invention may be administered either as a single dose or as part of a dosage regimen. A dosage regimen may be adjusted to provide an optimum therapeutic response. For example, several or multiple doses may be administered at a predetermined time interval and doses may be proportionally reduced as indicated by the exigencies of a therapeutic situation. By administering an embodiment of a composition of the present invention as part of a dosage regimen, circulating or local concentrations may be allowed to reach a desired equilibrium concentration for a compound through a series of doses. Depending on the severity and responsiveness of the condition to be treated, dosing can also be a single administration of a slow release composition, with course of treatment lasting from several days to several weeks or months or until the disease or condition is cured or an effective reduction in the underlying causes and/or symptoms of the disease state is achieved.

According to another broad aspect of the present invention, methods are provided for treating, inhibiting, preventing, managing, ameliorating, etc., an ischemic or hypoxic condition or disease (i.e., diseases or conditions caused by insufficient blood flow to one or more tissues), such as coronary artery disease, peripheral vascular occlusion or disease, peripheral arterial disease (e.g., critical limb ischemia or CLI), avascular necrosis, such as osteonecrosis, aseptic necrosis, or ischemic bone necrosis, and the like, by administering a mutant FGF protein to an individual, subject, or patient. According to some embodiments, a composition comprising a mutant FGF protein may be administered by local injection, injection or delivery via catheterization, placement, or implantation at a desired site of action in the body of an individual, subject, or patient, such as by application at, into, onto, or near a site of a disorder or disease (e.g., at, into, onto, or near a tissue or cellular environment experiencing ischemic or hypoxic stress).

Alternatively, a pharmaceutical composition comprising a mutant FGF protein may be administered by local injection, placement, or implantation at, into, onto, or near a site causing an ischemic or hypoxic stress or condition at a different site, such as at or near a site of vessel occlusion, which may be caused by atherosclerosis or plaque formation. For example, a composition comprising a mutant FGF protein may be administered at or near one or more sides of a site of vessel occlusion to encourage new vessels to augment blood flow or to bypass the site of blockage.

Such a local injection, injection or delivery via catheterization, placement, or implantation of pharmaceutical compositions of the present invention may include any form of suitable peri- and intra-tissue modes of injection, placement, or implantation, such as intradermal, intramuscular, intracardiac, subcutaneous, intrathecal, etc. as the case may be. In the case of coronary artery disease, for example, a composition comprising a mutant FGF protein may be administered by local injection or placement at, into, onto, or near cardiac tissue or cardiac muscle.

According to another broad aspect of the present invention, methods are provided for improving the quality and/or rate of tissue repair and/or wound healing by administering a mutant FGF protein to an individual, subject, or patient. According to some embodiments, a composition comprising a mutant FGF protein may be administered by injection, placement, or implantation at, into, onto, or near a site of a wound or tissue damage. According to some embodiments, such a wound or tissue damage may be caused by traumatic injury. According to other embodiments, such a wound or tissue damage may be immunologically mediated. By administering a mutant FGF protein to a site of a wound or tissue damage, wound healing or tissue repair may be promoted or improved by increased growth, proliferation, and/or survival of cells and/or angiogenesis to provide blood flow to the repaired or healed tissue. For example, a composition comprising a mutant FGF protein may be administered according to some embodiments to cardiac or brain tissue following myocardial infarction or stroke, respectively, to promote repair, neovascularization, and/or healing of the damaged tissues. According to some embodiments, a composition comprising a mutant FGF protein may be administered by injection, catheterization, placement, or implantation at, into, onto, or near a site of an incision or tissue damage or removal resulting, at least in part, from a surgical operation to promote healing and repair of the tissue.

According to some embodiments, a composition comprising a mutant FGF protein may be administered according to some embodiments to an individual, subject, or patient having a neural injury due to trauma or disease. Such a neural injury may be due to an immunologic condition, disorder, or disease, such as transverse myelitis (TM) including acute transverse myelitis (ATM) or idiopathic transverse myelitis (ITM), brachial plexus injury including obstetric brachial plexus injury (OBPP), or other spinal cord or peripheral nerve injuries or diseases. By administering a composition comprising a mutant FGF protein by injection, placement, or implantation at, into, onto, or near a site of neuronal tissue damage in the body of an individual, subject, or patient, the proliferation, growth, regeneration, and/or survival of neuronal cells may be achieved to promote repair or healing of neuronal tissue, which may lead to a reduction or alleviation of the causes or symptoms of neuronal disease or tissue damage.

Following administration of an embodiment of a composition comprising a mutant FGF protein, progress against a condition or disease may be monitored by a skilled scientist, veterinarian, or physician using any known or available reagent, assay, pathological or medical technique, equipment, etc. For example, progress against an ischemic or hypoxic condition or disease may be monitored by determining the amount of blood flow, vascularization, and tissue oxygenation following treatment. Imaging devices and techniques permit the visualization of vessels and blood flow especially with a contrast dye, and other devices and techniques, such as oximeters, etc., may be used to measure tissue oxygenation.

According to another broad aspect of the present invention, cells may be grown ex vivo (e.g., in culture following removal from a donor individual and prior to transfer to a recipient) for use in transplantation, tissue engineering, or engraftment into an individual, subject, or individual receiving the cells as treatment. Growing or culturing cells ex vivo may allow for their expansion and/or manipulation prior to use. According to these embodiments, a mutant FGF protein may be introduced to these cells grown ex vivo or in culture to improve the growth, expansion, proliferation, and/or survival. According to some embodiments, the donor may be the same individual, subject, or patient as the recipient.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1: Structural Basis of Conserved Cysteine in FGF Protein Family

The cysteine residue at position 83 of human FGF-1 is conserved among the 22 mouse/human FGF proteins. In this example, the structural role of Cys 83 in FGF-1 as well as the effect of mutation of Cys 83 on protein stability is examined. In addition, the effects of mutating the alanine at position 66 of human FGF-1 to cysteine are determined.

Materials and Methods

Mutagenesis and Expression:

Experiments in this example utilize a synthetic gene for the 140 amino acid form of human FGF-1 containing an additional amino-terminal His tag as previously described. See, e.g., Brych et al. (2001), supra; Linemeyer, D. L. et al., "Disulfide bonds are neither required, present, nor compatible with full activity of human recombinant acidic fibroblast growth factor," *Growth Factors* 3:287-298 (1990); Blaber, M. et al., "X-ray crystal structure of human acidic fibroblast growth factor," *Biochemistry* 35:2086-2094 (1996); Gimenez-Gallego, G. et al., "The complete amino acid sequence of human brain-derived acidic fibroblast growth factor," *Biochemical and Biophysical Research Communications* 128:611-617 (1986); and Cuevas, P. et al. (1991), supra, the entire contents and disclosure of which are hereby incorporated by reference. The QuikChange™ site directed mutagenesis protocol (Stratagene, La Jolla, Calif.) is used to introduce point mutations, which may be confirmed by nucleic acid sequence analysis (Biomolecular Analysis Synthesis and Sequencing Laboratory, Florida State University). Expression and purification protocols may follow previously published procedures. Purified protein is exchanged into 50 mM sodium phosphate, 0.1 M NaCl, 10 mM ammonium sulfate, 2 mM dithiothreitol (DTT), pH 7.5 ("crystallization buffer"). Due to the potential for disulfide bond formation, the purified Ala66→Cys mutant protein is exchanged against crystallization buffer both with and without the inclusion of DTT. The yield for most of the mutant proteins is 20-40 mg/L. However, Cys83→Ile could not be isolated due to significant precipitation during purification (suggesting substantial destabilization). Therefore, Cys83→Ile is constructed in a Lys12→Val+Cys117→Val stabilizing background. See, e.g., Dubey, V. K. et al. (2007), supra. Lys12→Val+Cys117→Val is chosen for this example since these mutation sites are distal to position Cys83 while providing −8.1 kJ/mol of additional thermostability.

Isothermal Equilibrium Denaturation:

This method makes use of the fluorescence signal of the single endogenous Trp residue at position 107. This residue is ~90% buried in the native structure and is therefore useful as a spectroscopic probe of protein denaturation. Complete details of the instrumentation, data collection and analysis procedure have been previously reported. See, e.g., Blaber, S. I. et al., "Reversible thermal denaturation of human FGF-1 induced by low concentrations of guanidine hydrochloride," *Biophysical Journal* 77:470-477 (1999), the entire contents and disclosure of which are hereby incorporated by reference. Briefly, the fluorescence signal of FGF-1 is atypical in that Trp107 exhibits greater quenching in the native state rather than the denatured state. Excitation at 295 nm provides selective excitation of Trp107 in comparison with the six Tyr residues that are present in the structure. About 5 µM of protein samples in various concentrations of GuHCl are allowed to equilibrate overnight at room temperature (298 K). Triplicate scans are collected and averaged and buffer traces are collected and subsequently subtracted from protein scans. Scans are integrated to quantify the total fluorescence as a function of denaturant concentration. In this example, the data is analyzed using a general purpose non-linear least-squares fitting program (DataFit, Oakdale Engineering, Oakdale Pa.) implementing a six parameter, two-state model as described by the following equation (1):

$$F = \frac{F_{0N} + S_N[D] + (F_{0D} + (S_D[D]))e^{-(\Delta G_0 + m[D])/RT}}{1 + e^{-(\Delta G_0 + m[D])/RT}} \quad (1)$$

where [D] is the denaturant concentration, $F_{0N}$ and $F_{0D}$ are the 0 M denaturant intercepts for the native and denatured state baselines, respectively, and $S_N$ and $S_D$ are the slopes of the native and denatured state baselines, respectively. See, e.g., Eftink, M. R. "The use of fluorescence methods to monitor unfolding transitions in proteins," *Biophysical Journal* 66:482-501 (1994), the entire contents and disclosure of which are hereby incorporated by reference. $\Delta G_0$ and m describe the linear function of the unfolding free energy versus denaturant concentration, where $\Delta G_0$ refers to $\Delta G_{unfolding}$ value extrapolated to 0M denaturant concentration (i.e. the y-intercept of the linear function) and m is the slope. In this example, the effect of a given mutation upon the stability of the protein ($\Delta\Delta G$) is calculated by taking the difference between the $C_m$ values for wild-type and mutant proteins and multiplying by the average of the m values as described by the following equation (2):

$$\Delta\Delta G = (C_{m\ WT} - C_{m\ mutant})(m_{WT} + m_{mutant})/2 \qquad (2)$$

where a negative value indicates the mutation is stabilizing in relationship to the wild type protein. See, e.g., Pace, C. N. et al., "Measuring the conformational stability of a protein," *Protein Structure: a Practical Approach*, Creighton, T. E., ed., p. 299-321, (Oxford University Press; Oxford, UK 1997), the relevant contents and disclosure of which are hereby incorporated by reference.

Crystallization, Data Collection, Molecular Replacement, and Refinement:

Purified mutant protein in crystallization buffer is concentrated to 9-13 mg/ml, and crystals are grown using the hanging-drop vapor diffusion method. Crystals suitable for diffraction are grown in one week at room temperature with 1 ml of reservoir solution containing 2.0-3.5 M sodium formate and 0.1-1.0 M ammonium sulfate in the crystallization buffer. The Ala66→Cys mutant crystal setups are performed in crystallization buffer in the presence and absence of DTT. Diffraction data for each of the mutant proteins, except Cys83→Ile+Lys12→Val+Cys117→Val, is collected using a Rigaku RU-H2R rotating anode X-ray source (Rigaku MSC, The Woodlands, Tex.) equipped with Osmic Blue confocal mirrors (MarUSA, Evanston, Ill.) and a Rigaku R-axis IIc image plate detector. In this example, diffraction of Cys83→Ile+Lys12→Val+Cys117→Val mutation is performed at the Southeast Regional Collaborative Access Team (SER-CAT) 22-BM beam line ($\lambda$=1.00 Å) at the Advanced Photon Source at Argonne National Laboratory using a MarCCD225 detector (MarUSA, Evanston, Ill.). Crystals are mounted using Hampton Research (Aliso Viejo, Calif.) nylon mounted cryo-turns and frozen in a stream of nitrogen gas at 100 K. Diffraction data is indexed, integrated and scaled using the DENZO software package. See, e.g., Otwinowski, Z., *Proceedings of the CCP4 Study Weekend: "Data Collection and Processing,"* (1993); and Otwinowski, Z. et al., "Processing of x-ray diffraction data collected in oscillation mode," *Methods in Enzymology* 276: 307-326 (1997), the entire contents and disclosure of which are hereby incorporated by reference. His-tagged wild-type FGF-1 (PDB code: 1JQZ) is used as the search model in molecular replacement for structures using the Crystallography and NMR System (CNS) software. See, e.g., Brunger, A. T. et al., "Crystallography and NMR system (CNS): A new software system for macromolecular structure determination," *Acta Crystallographica* D54:905-921 (1998), the entire contents and disclosure of which are hereby incorporated by reference. Model building and visualization utilizes the O molecular graphics program. See, e.g., Johnson, D. E. et al., "The human fibroblast growth factor receptor genes: a common structural arrangement underlies the mechanisms for generating receptor forms that differ in their third immunoglobulin domain," *Molecular and Cellular Biology* 11:4627-4634 (1991), the entire contents and disclosure of which are hereby incorporated by reference. Structure refinement utilizes CNS software, with 5% of the data in the reflection files set aside for $R_{free}$ calculations. Quantification of solvent-excluded cavities with the refined mutant structures is performed using the MSP software package. See, e.g., Connolly, M. L., "The molecular surface package," *Journal of Molecular Graphics* 11:139-141 (1993), the entire contents and disclosure of which are hereby incorporated by reference.

Results

Mutant Protein Purification:

The mutant proteins in this example except the Cys83→Ile and Ala66→Cys mutations are purified with equivalent yield (~20 mg/L) and purity (i.e., homogeneity by Coomassie Blue stained SDS PAGE) as the wild-type recombinant protein. The Cys83→Ile mutation exhibits very low solubility resulting in substantial precipitation during purification. However, when constructed in the Lys12→Val+Cys117→Val mutant background, the Cys83→Ile+Lys12→Val+Cys117→Val mutant is purified with a yield of ~15 mg/L of soluble protein. The Ala66→Cys mutation, exchanged into a final buffer with no DTT, yields a doublet band (of varying intensity depending on preparation) using SDS PAGE under non-reducing conditions. This doublet is resolved as a single band (with migration rate equivalent to the slower-migrating band of the non-reduced doublet) upon reduction. Thus, as initially purified under non-reducing buffer conditions, the Ala66→Cys mutant contains a partially-formed intra-molecular disulfide bond. Homogenous preparations of a reduced form of the Ala66→Cys mutation could readily be achieved by the inclusion of 10 mM DTT in buffer components utilized throughout the purification.

Isothermal Equilibrium Denaturation:

For this example, the derived thermodynamic parameters for the mutant proteins in comparison to wild-type FGF-1 (or Lys12→Val/Cys117→Val reference mutant) are summarized in the table in FIG. 6. Point mutations at position 83 destabilize the protein and vary from about 5.2 to about 12.6 kJ/mol. $\Delta\Delta G$ for the Cys83→Ser mutation is about 6.8 kJ/mol in good agreement with our previous report. See Culajay (2000), supra. The proteins exhibit excellent agreement with a two-state denaturation model, with the exception of the Ala66→Cys mutation. Under reducing conditions, the isothermal equilibrium denaturation of Ala66→Cys is described by a two-state process having a denaturation midpoint of about 1.01 M GuHCl. (See table in FIG. 6). However, under conditions where DTT is omitted from the purification buffer, the unfolding transition has two discernable components with substantially different midpoints of denaturation. The relative fraction of each component is variable, and depends upon the particular preparation. Fully reduced Ala66→Cys mutant protein is therefore prepared and exchanged into non-reducing buffer (i.e., crystallization buffer with no DTT), and the isothermal equilibrium unfolding behavior is characterized as a function of incubation time (see FIG. 8). These results show that under air oxidation the initially fully-reduced Ala66→Cys mutant protein slowly converts to a more stable form having a denaturation midpoint of about 1.87 M GuHCl (see table in FIG. 6). The rate of loss of the reduced form proceeds with apparent first-order exponential kinetics with a half-life of about 60 hours (see FIG. 9) and is inversely proportional to the formation of the oxidized form. The emergence of the higher-stability oxidized form also corresponds to a faster-migrating band under non-reducing SDS PAGE, consistent with formation of a specific intra-molecular disulfide bond (see FIG. 9). Analysis of the isothermal equilibrium data associated with the more stable oxidized form shows that it is 10.4 kJ/mol more stable than the wild-type protein and 13.6 kJ/mol more stable than the reduced form (see FIGS. 6 and 10).

X-Ray Structure Determination:

Diffraction-quality crystals were obtained for the Cys83→Ser, Cys83→Thr, Cys83→Ala, Cys83→Val, Cys83→Ile+Lys12→Val+Cys117→Val, reduced and oxidized forms of Ala66→Cys mutant proteins. X-ray diffraction data sets with resolution ranges between 1.90 and 2.55 Å are collected with excellent completion in each case. Structures are refined to acceptable crystallographic residual and stereochemistry. (See table in FIGS. 7-1 and 7-2) The mutants, except Cys83→Ile+Lys12→Val+Cys117→Nal and reduced Ala66→Cys, are crystallized in orthorhombic space group ($C222_1$) with two molecules in the asymmetric unit (isomorphous with the wild-type FGF-1 crystal form). The Cys83→Ile+Lys12→Val+Cys117→Val and reduced Ala66→Cys mutant proteins both crystallized in a related $P2_1$ monoclinic space group. Analysis of this $P2_1$ cell indicated a Matthews' coefficient of 2.8 Å$^3$/Da with four molecules in the asymmetric unit. These four molecules are successfully positioned using molecular replacement with wild-type FGF-1 (PDB ID: 1JQZ) as the search model, in both cases. The $2F_o$–$F_c$ difference electron density is unambiguous at the mutation site(s), and the mutant structures could be accurately modeled in each case.

Summaries of individual X-ray structures is provided in the following paragraphs:

Cys83→Ala:

The wild-type Cys83 Sγ participates as an H-bond acceptor with the main chain amide of residue Asn80 and with an H-bond distance of 3.5 Å. The Ala mutation deletes the side chain Sγ group and the associated H-bond with the Asn80 main chain amide (see FIG. 11A). The structure of the Ala mutation shows no obvious H-bond partner for the Asn80 main chain amide, and it therefore appears as an unsatisfied H-bond group. There is minimal structural collapse in response to the deletion of the side chain Sγ group, and a cavity calculation indicates the presence of a novel 7 Å$^3$ cavity (detected using 1.0 Å radius probe) adjacent to the CO at the former location of the Sγ.

Cys83→Ser:

The Ser mutation substitutes an Oγ hydroxyl for the wild-type Cys Sγ. The mutant Ser side chain adopts the same rotamer (gauche+) as the wild-type Cys, and is thus oriented appropriately to participate as an H-bond acceptor to the Asn80 main chain amide. Due to the smaller diameter of the oxygen atom, the structure must collapse somewhat to bring the Asn80 main chain amide within effective H-bond distance of the mutant Ser83 Oγ. However, the mutant structure shows minimal evidence of any such structural adjustment, and the resulting Ser83 Oγ and Asn80 N atomic distance is 3.7±0.4 Å (average of two independent molecules in the asymmetric unit) indicating that no significant H-bond interaction occurs between these groups. The most pronounced structural change in the Ser mutant is a 20° rotation of the Asn80 $\chi_2$ angle, resulting in a novel H-bond interaction (2.7 Å) between the introduced Ser83 Oγ and Asn80 Oδ1 (see FIG. 11B). In this H-bond interaction, the Ser83 Oγ is the donor to the Asn80 Oδ1 acceptor. Thus, the mutant Ser side chain is participating in a different type of H-bond interaction in comparison to the wild-type Cys. In adjusting to position its acceptor group towards the introduced Ser, the Asn80 Oδ1 breaks its H-bond with the main chain amide at position Glu82. Consequently, this main chain amide is an unsatisfied H-bond group.

Figure 11A:
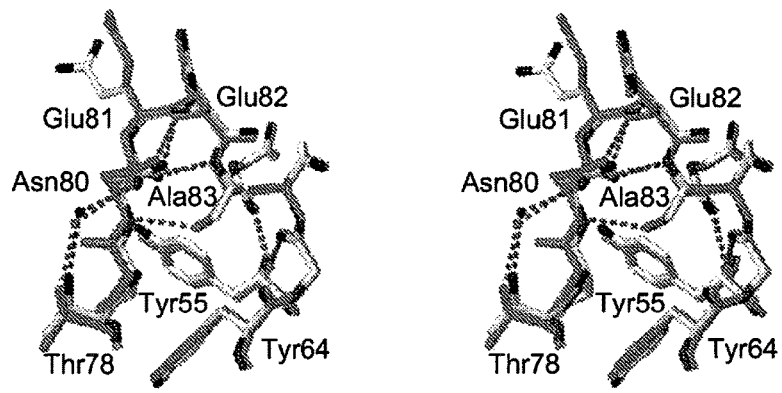
Figure 11B:
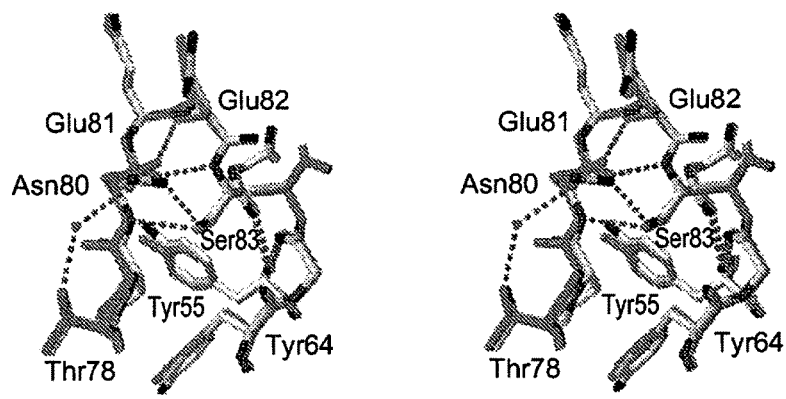
Figure 11C:
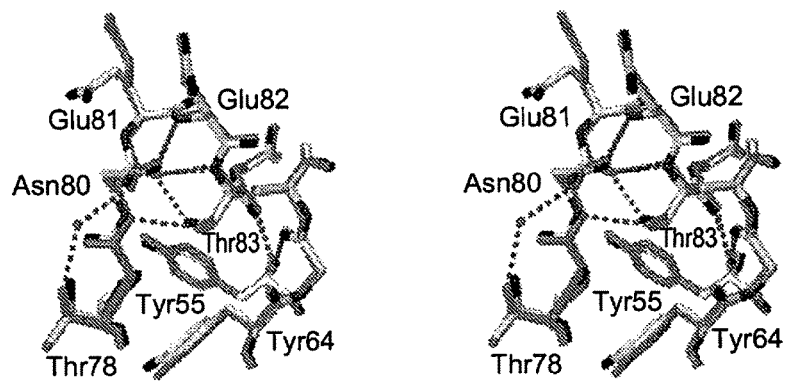

Cys83→Thr:

The Cy2 atom of the mutant Thr83 side chain juxtaposes the wild-type Cys Sγ atom (FIG. 11C). In this orientation, the H-bond interaction with the main chain amide of position Asn80 is lost, and this amide appears as an unsatisfied H-bond donor. The rotamer orientation of the mutant Thr positions the side chain Oγ1 atom adjacent to the aromatic ring of Tyr55, which moves slightly to avoid close van der Waals contact. In this orientation the introduced Thr Oγ1 participates as an H-bond donor to the main chain carbonyl group of Asn80.

Figure 11D:
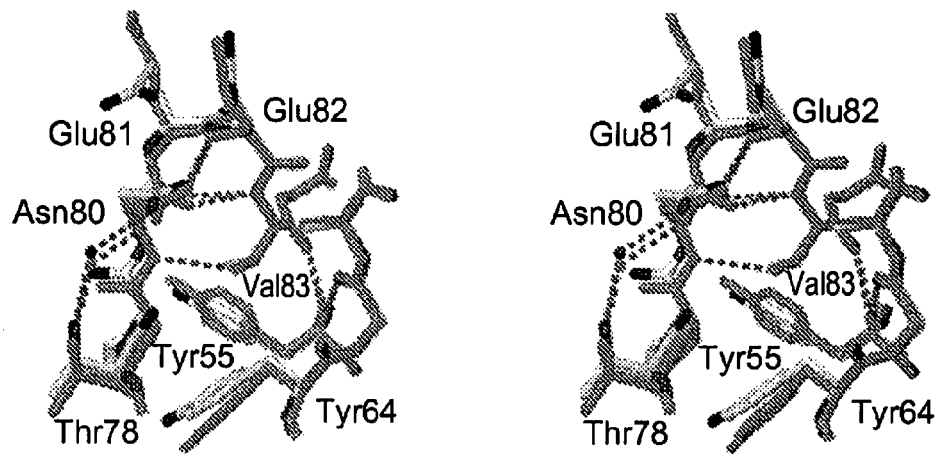
Figure 11E:
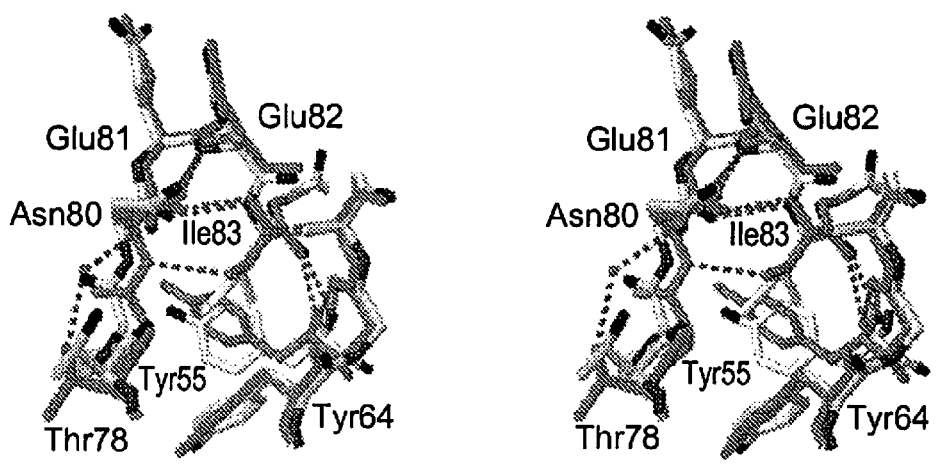

Cys83→Val:

The mutant Val side chain rotamer is essentially isosteric to that of the Thr83 mutant (FIG. 11D). As with the Thr83 mutant, the Asn80 main chain amide H-bond is lost. Furthermore, the novel H-bond observed with the mutant Thr83 Oγ1 and Asn80 main chain carbonyl is not present. Additionally, the movement of the aromatic ring of Tyr55 appears more pronounced than with the Thr mutant.

Cys83→Ile:

The mutant Ile side chain Cβ methyl groups are not accommodated isosteric to the related Val83 mutant. Rather, the Ile Cy2 is oriented towards the aromatic ring of Tyr55 which rotates ~90° to avoid close van der Waals contact (see FIG. 11E). With this rotamer, the mutant Ile Cγ1 juxtaposes with the wild-type Cys83 Sγ, and this positions the Ile Cδ1 atom between the Tyr64 aromatic ring and the Cα of residue position Pro79. The Cα of Pro79 shifts ~1.0 Å to accommodate the introduced Ile Cδ1.

Ala66→Cys (Reduced):

The reduced form of the Ala66→Cys mutant yielded diffraction quality crystals. The $P2_1$ crystal form obtained has four molecules in the asymmetric unit. In two of these, Cys83 adopts the wild-type gauche+($\chi1=-60°$) rotamer and is oriented towards position 66. However, Cys66 adopts a trans rotamer ($\chi1=180°$) and orients away from position 83. In the other two molecules, Cys66 adopts a gauche+($\chi1=-60°$) rotamer and is oriented towards position 83. However, position 83 adopts a gauche– ($\chi1=+60°$) rotamer and is oriented away from position 66. Both of these alternative orientations is associated with noticeable distortion of the local structure, but principally involving the gauche–rotamer of Cys83 and trans rotamer of Cys66 (see FIG. 12). With the gauche– rotamer of Cys83 the Sγ is oriented towards the main chain region of residues 80 and 81, which shift their position ~1.2 Å to avoid close van der Waals contact. With the trans rotamer of Cys66 the Sγ is oriented towards the Tyr74 side chain Oη which shifts its position ~1.4 Å to avoid close van der Waals contact. There is substantially reduced structural distortion associated with the alternative gauche+ rotamer for position Cys66 and gauche+rotamer for position Cys83. Thus, the structural data show that for both Cys83 and Cys66 the rotamer orientations that are accommodated with the least structural distortion are compatible with disulfide bond formation (i.e., gauche+ in both cases).

Ala66→Cys (Oxidized):

In contrast to the reduced form, the oxidized form of the Ala66→Cys mutant crystallized in the wild-type $C222_1$ space group with two molecules in the asymmetric unit. Both molecules in the asymmetric unit exhibit essentially identical structural features in the region of the Cys66 mutation and show that the introduced Cys66 forms a disulfide bond with the wild-type Cys83 residue (FIG. 12, bottom panel). Each Cys residue adopts a gauche+rotamer in forming a disulfide bond, and the local structural features are remarkably free of any apparent perturbation. The main chain atoms of all residues within 5.0 Å of positions 66 and 83 overlay with a root-mean-square deviation of 0.23 Å, essentially within the error of the X-ray data set. There is an ~0.6 Å shift of the Cβ of Cys83 towards Cys66 in forming the disulfide, and the aromatic ring of adjacent Tyr55 correspondingly rotates ~0.4 Å towards Cys83.

Example 1 Discussion

Cysteine is the second-least abundant amino acid in proteins (after tryptophan), yet is among the most highly conserved in functionally important sites involving catalysis, regulation, cofactor binding, and stability. See, e.g., Fomenko, D. E. et al. (2008), supra. The unique properties of cysteine have their basis in the side chain Sγ sulfur atom participating in a variety of different functional roles, including disulfide bond formation, metal-binding, electron donation, hydrolysis, and redox-catalysis. However, some cysteine residues do not participate in these functional roles and exist instead as structural free-cysteines within the protein. These free cysteines are approximately evenly distributed between interior and solvent exposed positions. See, e.g., Petersen, M. T. N., (1999), supra. Free-cysteine residues within the interior of a protein can effectively limit the protein's functional half-life. These cysteines are potentially reactive thiols that are subject to chemical modification should they become exposed, as transiently occurs in the dynamic equilibrium process of maintaining protein structure. With regard to human FGF-1, structural data show that a buried free cysteine at position 83 participates as a rare H-bond acceptor, which suggests that the cysteine may be partially deprotonated and therefore a reactive thiol. Chemical reactivity (e.g., disulfide formation) of buried free cysteines may present major structural difficulties for accommodation within the native protein interior, which may result in an irreversible unfolding pathway. As reported, mutation to eliminate these buried free cysteine residues may produce a notable increase in functional half-life.

The absolutely conserved Cys83 in the FGF family of proteins includes those members for whom this residue participates as a half-cystine (involving the adjacent Cys66) as well as those members for whom Cys83 is a buried free cysteine (and adjacent position 66 is a non-cysteine residue). Thus, while Cys83 is conserved among the FGF family of proteins, Cys83 may have two distinctly different underlying roles: (1) a half-cystine which serves to stabilize protein structure; or (2) a reactive buried free cysteine that may contribute to irreversible unfolding and thereby regulate protein half-life. To better understand the role of the conserved Cys83 in FGF-1 (a member of the Fgf1 subfamily where this position is a buried free cysteine), the effects of Ala, Ser, Thr, Val and Ile point mutations at position 83 upon stability and structure are determined. Modeling studies indicate that unlike other amino acids, this set of amino acids can substitute the wild-type cysteine residue without introducing unacceptably short van der Waals contacts that would require gross structural adjustments (Gly is also possible, but can introduce a main chain entropic penalty). The thermodynamic data (see FIG. 6) show that none of the amino acids in this set can substitute for Cys83 without incurring a significant (i.e., about 5.2 to about 12.6 kJ/mol) stability penalty (i.e., cysteine is the only residue shown to be accommodated at position 83 without causing significant destabilization). Thus, there is a thermodynamic preference for a free cysteine at position 83 in FGF-1.

The X-ray data indicate that the structural environment surrounding Cys83 is essentially rigid and unable to adapt to even small changes that might otherwise accommodate alternative amino acids. Ser is isosteric with Cys and is typically considered a conservative substitution. However, the Ser oxygen atom has approximately 0.3 Å shorter van der Waals radius than sulfur. The hydrogen-bond between Cys83 and the Asn80 main chain amide is 3.5 Å, and modeling an isosteric serine into wild-type FGF-1 at position 83 results in a distance of 3.7 Å between the serine Oγ and Asn80 amide. Thus, the structure must collapse 0.3-0.4 Å to maintain this H-bond interaction with a serine mutation. The X-ray structure shows little in the way of compensating structural collapse with the Cys83→Ala mutation to fill the void left by the effective removal of the side chain Sγ, and therefore indicates that the surrounding structure of position 83 is relatively rigid. The structure of the Cys83→Ser mutation indicates a similarly limited ability to collapse. The average inter-atomic distance between the introduced Ser83 Oγ and the Asn80 main chain amide for the two independent molecules in the asymmetric unit is 3.7±0.4 Å, in good agreement with the modeling of a serine mutation in the wild-type structure, and shows that the Asn80 main chain amide cannot effectively provide an H-bond donor to the Ser at position 83. The hydrogen-bonding partner that is observed in the Cys83→Ser mutant is the Oδ1 acceptor (2.7 Å distance) contributed by the reoriented Asn80 side chain. The Val, Thr, and Ile mutations each exhibit some degree of close van der Waals contacts with the neighboring groups, necessitating structural adjustments that are associated with a negative impact upon stability. The X-ray data therefore indicate that the local packing environment of position 83 is both relatively rigid, and optimized to accommodate a free cysteine at this position.

In addition to the structural interactions directly involving position 83, analysis of the hydrogen-bonding details of adjacent positions shows that these also contribute to the observed preference for cysteine at position 83. Among the amino acids tested at this position, only with cysteine does the protein avoid unsatisfied H-bond interactions involving main chain amides in the local turn structure (i.e., residues 80 through 83). The Asn80 main chain amide is unsatisfied in the Cys83→Ala, Thr, Val and Ile mutants, and the Glu82 main chain amide is unsatisfied in the Cys83→Ala mutant. On the other hand, both these main chain amides are satisfied in their hydrogen-bonding requirement when cysteine is present at position 83 (see FIG. 11). Providing hydrogen-bonding partners for main chain amides in type 1 turns is known to be important in stabilizing the turn structure. See, e.g., Lee J. et al. (2008), supra; de Alba, E. Et al., "Turn residue sequence determines beta-hairpin conformation in designed peptides," *Journal of the American Chemical Society* 119:175-183 (1997); Santiveri, C. M. et al., "Beta-hairpin folding and stability: molecular dynamics simulations of designed peptides in aqueous solution," *Journal of Peptide Science* 10:546-565 (2004); and Wan, W.-Y. et al., "A natural grouping of motifs with an aspartate or asparagine residue forming two hydrogen bonds to residues ahead in sequence: their occurrence at α-helical N termini and in other situations," *Journal of Molecular Biology* 286:1633-1649 (1999), the entire contents and disclosures of which are hereby incorporated by reference. Thus, the destabilization associated with mutation of Cys83 involves the contribution of both local and more extensive hydrogen-bonding interactions.

The structural changes in response to the Cys83→Ser mutation provide additional insight into the unique properties of the cysteine residue at this position. When a Ser is introduced, the protein responds to provide an H-bond acceptor to the hydroxyl (i.e., the Oδ1 of Asn80). However, the sole H-bond partner for the wild-type cysteine is an H-bond donor (i.e., the nitrogen N of Asn80), even though the Asn80 side chain could rotate to provide an acceptor (as observed for the Ser83 mutant). Cys83 interacting as an H-bond acceptor, and not as a donor, suggests that this cysteine may be substantially deprotonated in the native structure. This is significant, not only because acting as an acceptor is the rarest type of H-bond interaction observed for cysteines, but also because it indicates that, in being deprotonated, Cys83 is a reactive thiol. See, e.g., Zhou, P. et al., "Geometric characteristics of hydrogen bonds involving sulfur atoms in proteins," *Proteins* (published online 2008), the entire contents and disclosure of which are hereby incorporated by reference. The $pK_a$ of an unperturbed cysteine is 8.4, and the X-ray data was collected at pH 7.5. Thus, it is not unreasonable that the $pK_a$ may be perturbed by the local electrostatic environment (possibly due to H-bond interaction with the Asn80 main chain amide or interaction with the positive edge of the aromatic ring of adjacent Tyr55) and that significant deprotonation of Cys83 occurs at pH 7.5. See, e.g., Britto, P. J. et al., "The local electrostatic environment determines cysteine reactivity in tubulin," *Journal of Biological Chemistry* 277:29018-29027 (2002), the entire contents and disclosure of which are hereby incorporated by reference. Thus, if position Cys83 becomes solvent accessible (as during transient fluctuations in the folding equilibrium), exposure of a reactive thiol would occur, and chemical modification of buried cysteines may contribute to an irreversible unfolding pathway. Therefore, position 83 in FGF-1 is optimized to accept a free cysteine, and this buried free cysteine may negatively regulate functional half-life.

The Ala66→Cys mutant tests the ability of the FGF-1 structure to accommodate a disulfide bond with the conserved Cys83. Cys66 is present at a corresponding position in six members of the FGF family within two of the seven proposed archetype subfamilies (i.e., the Fgf8 subfamily, which includes FGF-8, 17 and 18, and the hFgf subfamily, which includes FGF-19, 21 and 23). See, e.g., Itoh, N., "The FGF families in humans, mice, Zebrafish: their evolutional processes and roles in development, metabolism, and disease," *Biological and Pharmaceutical Bulletin* 30:1819-1825, (2007), the entire contents and disclosure of which are hereby incorporated by reference.

Subsequent X-ray structure determinations proved that the Cys at a position corresponding to position 83 of FGF-1 is a free thiol in FGF-1, -2, -4, -7, -9, -10, and -12. See, e.g., Blaber, M. et al., (1996), supra; Zhang, J. et al., "Three-dimensional structure of human basic fibroblast growth factor, a structural homolog of interleukin 1B," *Proceedings of the National Academy of Science USA* 88:3446-3450 (1991); Bellosta, P. et al., "Identification of receptor and heparin binding sites in fibroblast growth factor 4 by structure-based mutagenesis," *Molecular and Cellular Biology* 21:5946-5957 (2001); Ye, S. et al., "Structural basis for interaction of FGF-1, FGF-2, and FGF-7 with different heparan sulfate motifs," *Biochemistry* 40:14429-14439 (2001); Plotnikov, A. N. et al., "Crystal structure of fibroblast growth factor 9 reveals regions implicated in dimerization and autoinhibition," *Journal of Biological Chemistry* 276:4322-4329 (2001); Yeh, B. K. et al., "Structural basis by which alternative splicing confers specificity in fibroblast growth factor receptors," *Proc Natl Acad Sci USA* 100:2266-2271 (2003); and Olsen, S. K. et al., "Fibroblast growth factor (FGF) homologous factors share structural but not functional homology with FGFs," *J Biol Chem* 278:34226-36 (2003), the entire contents and disclosures of which are hereby incorporated by reference. However, FGF-8, -17, -18, -19, -21 and -23 each contain a cysteine residue at position 66 (in the numbering scheme of FGF-1) that lies adjacent to position 83. The crystal structures of FGF-8, 19, and 23 have been solved, and each shows a disulfide bond forms between Cys83 and the adjacent Cys66. See, e.g., Olsen, S. K. et al., "Structural basis by which alternative splicing modulates the organizer activity of FGF8 in the brain," *Genes Dev.* 20:185-198 (2006); Harmer, N. J. Et al., "The crystal structure of fibroblast growth factor (FGF) 19 reveals novel features of the FGF family and offers a structural basis for its unusual receptor affinity," *Biochemistry* 43:629-640 (2004); and Goetz, R. et al., "Molecular insights into the klotho-dependent, endocrine mode of action of fibroblast growth factor 19 subfamily members," *Mol Cell Biol* 27:3417-3428 (2007), the entire contents and disclosures of which are hereby incorporated by reference.

The introduction of a cysteine mutation at adjacent position 66 results in a form of FGF-1 that is less stable than wild-type under reducing conditions, but substantially more stable than wild-type when exposed to oxidizing conditions with concomitant formation of an intra-molecular disulfide bond. Under reducing conditions, the Ala66→Cys mutant in FGF-1 is 5.1 kJ/mol less stable than the wild-type protein (see FIG. 6), and the X-ray data shows some distortion of the local structure with both of the alternative conformations being observed for the pair of cysteines at positions 66 and 83 (see FIG. 12). The purified Ala66→Cys protein responds to increased incubation under oxidative conditions by forming a faster-migrating band on SDS-PAGE, and an increase in stability of 13.6 kJ/mol compared to the reduced mutant form (and 10.4 kJ/mol relative to the wild-type protein). Thus, the SDS-PAGE results indicate the formation of a specific intra-molecular disulfide (with no evidence for formation of any inter-molecular disulfide bond). In the wild-type FGF-1 (and reduced Ala66→Cys mutant) crystal structure, the Cβ-Cβ distance between position 66 and Cys83 is 4.3 Å, whereas the only other available thiols in FGF-1 are Cys16 and Cys117, whose Cβ-Cβ distance to position 66 are 18.0 Å and 12.0 Å, respectively. Thus, formation of a cystine between positions 66 and 83 in response to oxidation of the Ala66→Cys FGF-1 mutant is consistent with the thermodynamic and structural data provided herein.

In the crystal structure of the reduced form of the Ala66→Cys mutant, two rotamer orientations for each cysteine at positions 66 and 83 are identified, where the gauche+ rotamer in each case is necessary for disulfide bond formation. gauche+ is the natural rotamer for the wild-type Cys83. The potential S-S distance when both cysteine rotamers are gauche+ is 2.20 Å, optimal for forming a disulfide bond. However, the Cβ-Sγ-Sγ-Cβ torsion angle is ~0°, whereas a value of ~90° is canonical. See, e.g., Bhattacharyya, R. et al., "Disulfide bonds, their stereospecific environment and conservation in protein structures," *Protein Eng Des Sel* 17:795-808 (2004), the entire contents and disclosure of which are hereby incorporated by reference. Thus, adjustments in χ1 or the Cα-Cβ bond vector (via adjustment in main chain φ, ψ angles) for either, or both, residue positions appears necessary to promote disulfide bond formation. The isothermal equilibrium stability data provided herein indicate that the strain introduced by achieving such an adjustment is more than offset by the entropically-based gain in stability provided by formation of the disulfide bond.

The X-ray structure of the oxidized form of Ala66→Cys mutant shows formation of a disulfide bond between residues Cys66 and Cys83 (both molecules in the asymmetric unit are essentially identical in this regard). The resulting Cβ-Sγ-Sγ-Cβ torsion angle is observed to be a canonical 90°, accomplished principally through a Cα-Cβ vector adjustment involving position 83; other than this, the structural perturbation in response to the introduction of the disulfide bond is negligible. Thus, the wild-type structure readily accommodates the Ala66→Cys mutant in a rotamer that favors disulfide bond formation with adjacent Cys83, and Cys83 in the wild-type structure appears appropriately positioned (and also potentially deprotonated) to form a disulfide bond with an introduced Cys66. Formation of a disulfide between Cys 83 and Cys66 stabilizes the native structure by ~10 kJ/mol (FIG. 6). The oxidized form of Ala66→Cys exhibits a more than 10 fold increase in mitogenic activity and functional half-life in the absence of heparin (FIG. 17, FIG. 22, FIG. 24), which unambiguously confirms that a newly formed disulfide bond in the Ala66→Cys mutant provides favorable impact on functional stability of the protein.

A disulfide bond between cysteines at positions corresponding to positions 66 and 83 of human FGF-1 is present in two of the seven archetype subfamilies. As shown herein, wild-type FGF-1 is less stable than the Cys66 mutant with the disulfide bond. However, low thermal stability of FGF-1 and FGF-2 may be essential to their non-traditional secretion mechanism. See, e.g., Florkiewicz, R. Z. et al., "Quantitative export of FGF-2 occurs through an alternative, energy-dependent, non-ER/Golgi pathway," *J Cell Physiol* 162:388-99 (1995); Jackson, A. et al., "Heat shock induces the release of fibroblast growth factor 1 from NIH 3T3 cells," *Proc Natl Acad Sci USA* 89:10691-5 (1992); and Mach, H. et al., "Interaction of partially structured states of acidic fibroblast growth factor with phospholipid membranes," *Biochemistry* 34:9913-9920 (1995), the entire contents and disclosures of which are hereby incorporated by reference. As a potent mitogen, limiting functional half-life may be important, and modulation of reactive thiols in FGF-1 may influence the protein half-life by two-orders of magnitude. By contrast, the hFgf family, which does contain a cystine at positions corresponding to positions 66 and 83, is unique in that these molecules function in an endocrine fashion distal to the cells that secrete them when enhanced stability (as well as increased functional half-life) may be more important. Thus, while Cys83 is absolutely conserved in the Fgf family, the underlying basis for the selective pressure may differ between the family members and involves differential issues of stability or regulation of functional half-life. The results with FGF-1 suggest that other members of the Fgf family with a cysteine at position 83 may similarly be stabilized by a cysteine mutation at position 66.

Example 2: Interaction Between Thermostability and Buried Free Cysteines in Regulating the Functional Half-Life of FGF-1

In this example, the relationship between protein stability and buried free cysteines in influencing the functional half-life of FGF-1 is examined. Mutations that eliminate free cysteine residues are combined with protein stabilizing mutations to determine whether these mutations may have a combined, cooperative, and/or synergistic effect on protein stability.

Materials & Methods

Mutagenesis, Expression, and Purification of Recombinant Proteins:

Experiments in this example utilize a synthetic gene for the 140 amino acid form of human FGF-1 containing an additional amino-terminal six His tag (SEQ ID NO: 14) as previously described. See, e.g., Ortega, S. et al. (1991), supra; Gimenez-Gallego, G. et al. (1986), supra; Linemeyer, D. L. et al. (1990), supra; and Blaber, M. et al. (1996), supra. The QuikChange™ site directed mutagenesis protocol (Stratagene) is used to introduce mutations, and were confirmed by nucleic acid sequence analysis (Biomolecular Analysis Synthesis and Sequencing Laboratory, Florida State University). Expression and purification may follow previously published procedures. See, e.g., Brych, S. R. et al. (2001), supra. Purified protein was exchanged into 50 mM NaPi, 0.1 M NaCl, 10 mM $(NH_4)_2SO_4$, 2 mM DTT, pH 7.5 ("crystallization buffer") for crystallization studies or 20 mM N-(2-acetamido)iminodiacetic acid (ADA), 0.1 M NaCl, 2 mM DTT, pH 6.6 ("ADA buffer") for biophysical studies. The yield of most of the mutant proteins was 20-40 mg/L. In this example, an extinction coefficient of $E_{280\,nm}$ (0.1%, 1 cm)=1.26 is used to determine protein concentration for wild-type and mutant proteins with the exception of those mutations involving Trp substitutions. See, e.g., Zazo, M. et al., "High-level synthesis in *Escherichia coli* of a shortened and full-length human acidic fibroblast growth factor and purification in a form stable in aqueous solutions," *Gene* 113:231-238 (1992); and Tsai, P. K. et al., "Formulation design of acidic fibroblast growth factor," *Pharmaceutical Research* 10:649-659 (1993), the entire contents and disclosures of which are hereby incorporated by reference. Due to the addition of a novel Trp fluorophore in these proteins, their extinction coefficients are determined by densitometry analysis of Coomassie Brilliant Blue stained SDS PAGE of serial dilutions of purified mutant proteins normalized to concentration standards of wild-type FGF-1 (data not shown). The resulting $E_{280\,nm}$ (0.1%, 1 cm) values used in this example are: Leu44→Trp=1.41; Phe85→Trp=1.55; Phe132→Trp=1.58; Leu44→Phe+Phe132→Trp=1.58; Cys83→Thr+Cys117→Val+Leu44→Phe+Phe132→Trp=1.58.

Crystallization, X-ray data collection, and refinement: Purified protein in crystallization buffer is concentrated to 9-13 mg/ml, and crystals are grown using the hanging-drop vapor diffusion method. Crystals suitable for diffraction grow in one week at room temperature with 1.0 ml of reservoir solution containing 2.0-3.5 M sodium formate and 0.1-1.0 M ammonium sulfate in crystallization buffer. Crystals are mounted using Hampton Research nylon mounted cryo-turns and frozen in a stream of gaseous nitrogen at 100K. In this example, diffraction data are collected using a Rigaku RU-H2R rotating anode X-ray source (Rigaku MSC) equipped with Osmic Blue confocal mirrors (MarUSA) and a Rigaku R-axis IIc image plate detector. Diffraction data are indexed, integrated and scaled using the DENZO software package. See, e.g., Otwinowski, Z. et al. (1993), supra; and Otwinowski, Z. et al. (1997), supra. His-tagged wild type FGF-1 (PDB code: 1JQZ) is used as the search model in molecular replacement for mutant structures with the Crystallography and NMR System software (CNS). See, e.g., Brunger, A. T. (1998), supra. Model building and visualization utilizes the 0 molecular graphics program. See, e.g., Johnson, D. E. et al. (1991), supra. Structure refinement utilizes the CNS software, with 5% of the data in the reflection files set aside for Rfree calculations. Coordinates and structure factors are deposited in the PDB (coordinate file accession numbers are listed in the table in FIGS. 13-1 and 13-2). Cavities within the structures are quantified using the Molecular Surfaces Package (MSP) software and a 1.2 Å radius probe. See, e.g., Connolly, M. L. (1993), supra. The choice of 1.2 Å for the probe radius is slightly larger than the radius of a methyl group (1.1 Å) and identifies cavities that are of significance for possible aliphatic or aromatic point mutations.

Isothermal Equilibrium Denaturation:

Isothermal equilibrium denaturation by guanidine HCl (GuHCl) is performed using either fluorescence or circular dichroism as the spectroscopic probe as previously described. See, e.g., Kim, J. et al. (2003), supra. FGF-1 contains a single buried tryptophan residue at position 107 which exhibits atypically greater fluorescence quenching in the native state versus the denatured state, and this differential fluorescence is used to quantify the unfolding process. Fluorescence data are collected on a Varian Eclipse fluorescence spectrophotometer which is equipped with a Peltier controlled-temperature regulator at 298 K and using a 1.0 cm path length cuvette. 5.0 μM protein samples are equilibrated in ADA buffer at 298 K in 0.1 M increments of GuHCl. Triplicate scans are collected and averaged, and buffer traces are collected, averaged, and subtracted from the protein scans. Scans are integrated to quantify the total fluorescence as a function of denaturant concentration.

The Leu44→Trp, Phe85→Trp, Phe132→Trp, Leu44→Phe+Phe132→Trp, and Cys83→Thr+Cys117→Val+Leu44→Phe+Phe132→Trp mutations introduce an additional tryptophan residue in the protein. In each case, this additional tryptophan exhibits greater fluorescence quenching in the denatured state, and when combined with the endogenous Trp107 atypical fluorescence signal results in an overall fluorescence quenching profile that offers little discrimination between native and denatured states. FGF-1 unfolding monitored by circular dichroism (CD) spectroscopy exhibits excellent agreement with results obtained by fluorescence spectroscopy and is a useful alternative spectroscopic probe in cases where fluorescence cannot be utilized. Therefore, the isothermal equilibrium denaturation profile for the above mutants is characterized using CD spectroscopy. 25 μM protein samples are equilibrated in ADA buffer at 298K in 0.1 M increments of GuHCl. In this example, CD data are collected on a Jasco810 CD spectrophotometer (Jasco Inc) which is equipped with a Peltier controlled-temperature regulator at 298 K and using a 1 mm path length cuvette. For each sample, triplicate scans are collected and averaged, and buffer traces are collected, averaged, and subtracted from the sample traces. The unfolding process is monitored by quantifying the change in CD signal at 227 nm with increasing GuHCl. See, e.g., Blaber, S. I. et al. (1999), supra. In this example, both fluorescence and CD data are analyzed using the general purpose non-linear least-squares fitting program DataFit (Oakdale Engineering) implementing a six parameter, two-state model according to the following equation (3):

$$F = \frac{F_{0N} + S_N[D] + (F_{0D} + (S_D[D]))e^{-(\Delta G_0 + m[D])/RT}}{1 + e^{-(\Delta G_0 + m[D])/RT}} \quad (3)$$

where [D] is the denaturant concentration, $F_{0N}$ and $F_{0D}$ are the 0M denaturant intercepts for the native and denatured state baselines, respectively, and $S_N$ and $S_D$ are the slopes of the native and denatured state baselines, respectively. See, e.g., Eftink, M. R. (1994), supra. $\Delta G_0$ and m describe the linear function of the unfolding free energy versus denaturant concentration. In this example, the effect of a given mutation upon the stability of the protein (ΔΔG) is calculated by taking the difference between the $C_m$ values for wild-type and mutant proteins and multiplying by the average of the m values, as described by Pace and Scholtz, according to the following equation (4):

$$\Delta \Delta G = (C_{m\ WT} - C_{m\ mutant})(m_{WT} + m_{mutant})/2 \quad (4)$$

where a negative value indicates the mutation is stabilizing in relationship to the wild type protein. See, e.g., Pace, C. N. (1997), supra.

Differential Scanning Calorimetry:

In this example, DSC data are collected on a VP-DSC microcalorimeter (MicroCal LLC) as previously described. See, e.g., Blaber, S. I. (1999), supra. Briefly, 40 μM protein samples are equilibrated at 298 K in ADA buffer without DTT and in the presence of 0.7 M GuHCl. The samples are filtered and degassed for 10 min prior to loading. A scan rate of 15K/h is used and the sample was maintained at 30 psi during the calorimetric run. Protein samples are loaded, and data are collected without interruption of repeated thermal cycles. At least three independent protein scans are collected and averaged, the average of the buffer scans is subtracted, and the resulting scan is normalized to the molar protein concentration. The resulting molar heat capacity profiles are analyzed using the DSCfit software package. See, e.g., Grek, S. B. et al., "An efficient, flexible-model program for the analysis of differential scanning calorimetry protein denaturation data," *Protein and Peptide Letters* 8:429-436 (2001), the entire contents and disclosure of which are hereby incorporated by reference.

Mitogenic Activity and Functional Half-Life in Unconditioned Medium:

Purified protein is equilibrated in 0.14 M NaCl, 5.1 mM KCl, 0.7 mM $Na_2HPO_4$, 24.8 mM Tris base, pH 7.4 ("TBS buffer"), and the mitogenic activity is evaluated by a cultured fibroblast proliferation assay as previously described. See, e.g., Dubey, V. K. et al. (2007), supra. Briefly, NIH 3T3 fibroblasts are plated in Dulbecco's modified Eagle's medium (DMEM) (Gibco) supplemented with 0.5% (v/v) newborn calf serum (NCS) (Sigma) for 48 h at 37° C. with 5% (v/v) $CO_2$. The quiescent serum-starved cells are stimulated with fresh medium supplemented with FGF-1 protein (0-10 μg/ml) and incubated for an additional 48 hours. After this incubation period, the cells are counted using a hemacytometer (Hausser Scientific partnership). Experiments are performed in quadruplicate, and cell densities are averaged. The protein concentration yielding one-half maximal cell density ($EC_{50}$ value) is used for quantitative comparison of mitogenicity. To evaluate the effect of exogenous heparin on mitogenic potency, 10 U/ml of heparin sodium salt (Sigma) is optionally added to the protein prior to cell stimulation.

For functional half-life studies, the wild-type and mutant FGF-1 proteins are pre-incubated in unconditioned DMEM at 37° C. for various time periods (spanning 0-72 hr depending on the mutant) before being used to stimulate the 3T3 fibroblast mitogenic response as described above. Although the mitogenic assay spans 48 hours, the stimulation of FGF receptor in the initial minutes after FGF-1 addition may principally dictate the magnitude of the mitogenic response. Thus, even comparatively short pre-incubation periods (i.e., less than 1 hour) may be quantified for loss of functional activity. See, e.g., Ortega, S. et al. (1991), supra.

Resistance to Thiol Reactivity, Aggregation and Trypsin Proteolysis in TBS:

Wild-type and mutant proteins at a concentration of 0.25 mg/ml are incubated at 37° C. in TBS buffer and evaluated for disulfide bond formation and aggregation. Samples taken at time points of 0, 24, and 48 hours are centrifuged at 10,000×g for 5 min, and the soluble fraction mixed with SDS sample buffer (both with and without 5% BME) resolved on 16.5% Tricine SDS-PAGE and visualized with Coomassie Brilliant Blue staining. The stained gels are scanned, and the amount of soluble monomeric protein and disulfide-linked multimers is quantified using UN-SCAN-IT densitometry software (Silk Scientific).

Wild-type and mutant proteins are incubated with trypsin (Promega) (200:1 molar ratio, respectively) in TBS buffer at 37° C. to evaluate resistance to proteolysis. Time points are taken at 0, 5, 15 and 30 min and resolved on 16.5% Tricine SDS-PAGE visualized with Coomassie Brilliant Blue staining. The stained gels are scanned, and the amount of intact protein is quantified using UN-SCAN-IT densitometry software (Silk Scientific).

Results

Mutant Protein Purification:

Mutant proteins are expressed and purified to apparent homogeneity and with a yield similar to that of wild-type protein (20-40 mg/L).

X-Ray Structure Determination:

Diffraction-quality crystals are obtained for the Leu44→Trp, Phe85→Trp, Phe132→Trp, Val31→Ile, Cys117→Ile point mutations, the Leu44→Phe+Phe132→Trp double mutant, and the Leu44→Phe+Cys83→Thr+Cys117Val+Phe132→Trp quadruple mutant. In this example, each of these mutant proteins crystallizes in the wild-type orthorhombic C2221 space group with two molecules in the asymmetric unit, and yielded 1.95-2.0 Å resolution data sets in each case. The crystal structures are refined to acceptable crystallographic residuals and stereochemistry (see table in FIGS. 13-1 and 13-2). A brief description of each refined structure follows. However, in presenting the results a description of the packing defects (i.e., cavities) within the core of the wild-type protein is necessary. The wild-type FGF-1 protein (1JQZ, molecule A) contains eight cavities detectable using a 1.2 Å radius probe. These cavities are identified by number ("cav1" through "cav8") and details of their volume and location are provided in FIG. 18.

Figure 19A:
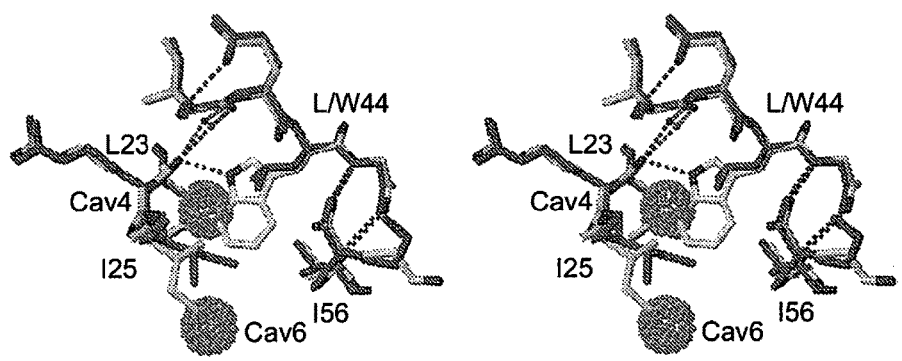

Summaries of individual X-ray structures is provided in the following paragraphs:

Leu44→Trp:

The mutant Trp side chain at position 44 is adopted with a $\chi1=-56°$ (similar to the wild-type Leu44 $\chi1=-44°$) and $\chi2=90°$ (which differs from the wild-type Leu44 $\chi2=165°$) (FIG. 19A). Cav4 lies adjacent to the side chain of position 44, and the CZ2 atom of the mutant indole ring occupies this region and effectively fills this cavity. The mutant Trp, however, introduces a close contact with the adjacent Ile side chain at position 25, which responds by rotating from a gauche+ to trans rotamer. In this orientation, the Ile25 Cδ1 atom occupies the adjacent cav6. This reorientation of the Ile25 side chain to accommodate the mutant Trp also involves a 1.0 Å shift of the Ile25 main chain Cα away from position 44, leading to an apparent increase in the Ile25N-His41O inter-chain H-bond distance from 3.1 Å to 3.3 Å. The nitrogen in the indole ring of the mutant Trp H-bonds with the main chain carbonyl of residue Leu23 and is achieved with minimal structural perturbation.

Figure 19B:
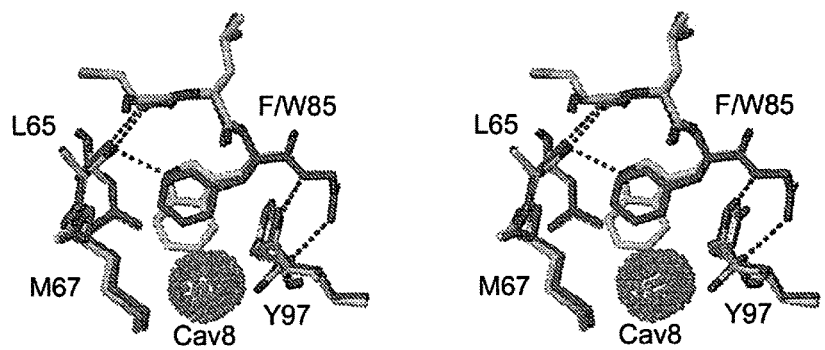

Phe85→Trp:

The mutant Trp side chain at position 85 is adopted with a $\chi1=-61°$ (essentially identical to the wild-type Phe85 $\chi1=-65°$) and $\chi2=95°$ (identical to the wild type Phe) (FIG. 19B). Cav8 lies adjacent to the side chain of position 85 and the CZ3 atom of the mutant indole ring occupies this region and substantially fills this cavity. Accommodation of the mutant Trp is associated with minimal perturbation of the surrounding structure. The nitrogen in the indole ring of the mutant Trp H-bonds with the main chain carbonyl of residue Leu65 and is achieved with minimal structural perturbation.

Figure 19C:
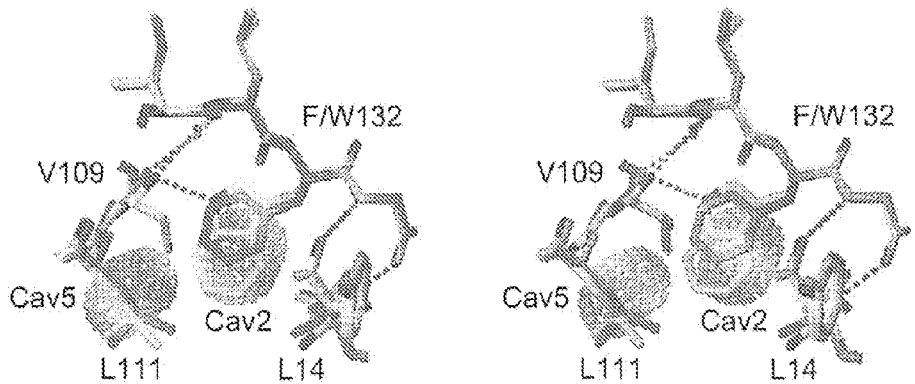

Phe132→Trp:

The mutant Trp side chain at position 132 is adopted with a $\chi1=-59°$ (similar to the wild-type Phe132 $\chi1=-68°$) and $\chi2=85°$ (essentially identical to the wild-type Phe132 $\chi2=89°$) (FIG. 19C). Two cavities are located adjacent to position 132: cav2 lies beneath the aromatic ring of Phe132 (and is the large central cavity characteristic of the β-trefoil architecture), and cav5 is adjacent to the introduced Trp CZ2 atom. See, e.g., Murzin, A. G. et al. (1992), supra. The mutant Trp side chain partially fills both of these cavities. Accommodation of the mutant indole ring is associated with minimal perturbation of the surrounding structure. There is a slight rotation of the $\chi2$ angle of adjacent Leu111 as well as a slight repositioning of the main chain carbonyl of adjacent residue Leu14, and both of these structural adjustments are in a direction away from the mutant indole ring. The nitrogen of the indole ring in the mutant Trp hydrogen bonds with the main chain carbonyl of residue Val109 and is achieved with minimal structural perturbation.

Figure 19D:
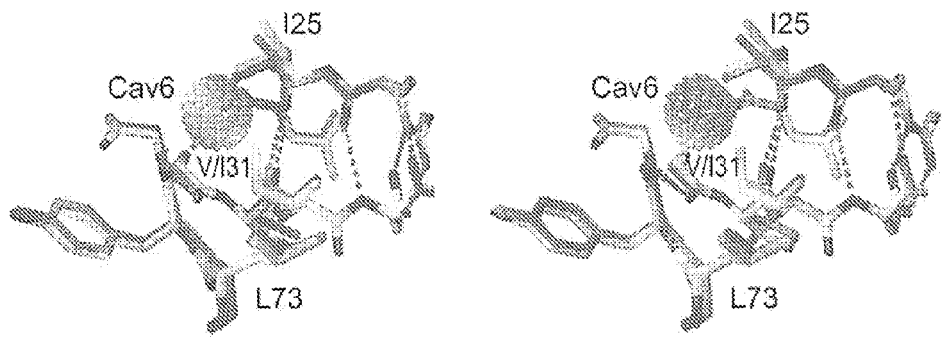

Val31→Ile:

The mutant Ile side chain at position 31 adopts a $\chi1=-55°$ (essentially overlaying the wild-type Val side chain at this position) and $\chi2=-60°$ (FIG. 19D). Cav6 lies adjacent to the introduced Ile Cδ1 atom, but is only partially filled. However, in response to the introduction of the mutant Ile Cδ1 at position 31, adjacent residue Ile25 shifts in a direction away from position 31, such that the Cβ-Cβ distance between these neighboring groups increases from 5.6 Å to 6.1 Å. Thus, while the mutant Ile side chain partially fills an adjacent cavity, its accommodation is associated with positional adjustment of neighboring side chains.

Figure 19E:
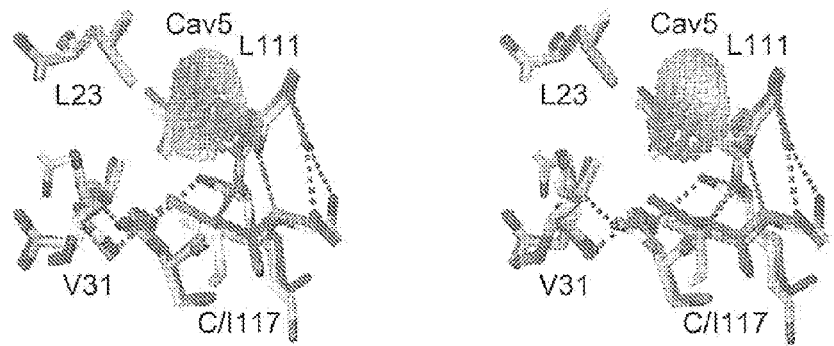

Cys117→Ile:

The mutant Ile side chain at position 117 adopts a $\chi1=49°$ (essentially overlaying the mutant Ile Cγ2 atom onto the wild-type Sγ atom) and a $\chi2=-175°$ (FIG. 19E). Cav5 is adjacent to position 117. However, the $\chi2$ rotamer adopted by the mutant Ile side chain positions its Cγ1 and Cδ1 atoms away from this cavity. The Ile mutation therefore has no effect upon the size of adjacent cav5. Furthermore, this orientation for the mutant Ile side chain positions the Cγ1 and Cδ1 atoms outside of the core region, and these atoms become solvent accessible.

Leu44→Phe+Phe132→Trp: The structural effects of the Leu44→Phe point mutant have been reported. See, Brych et al. (2001), supra. Briefly, the introduction of the Phe aromatic ring essentially fills cav4, and the adjacent Ile25 side chain retains its rotamer orientation but shifts position away from Phe44 and fills cav6. Positions 44 and 132 are not adjacent packing neighbors and residues Leu14 and Leu23 are sandwiched between them. The structural effects of the Phe132→Trp point mutant is described above, and the Leu44→Phe+Phe132→Trp double mutant can be described as comprising the additive effects of the constituent point mutations. In this regard, this combined double mutant effectively fills cav4, cav6 and partially fills cav5 (FIG. 20A).

Leu44→Phe+Cys83→Thr+Cys117→Val+Phe132→Trp:

The structural effects of the Cys117→Val point mutant have been reported. See, e.g., Brych et al. (2003), supra. The Leu44→Phe/Phe132→Trp double mutant is described above. None of these four positions within the core region of the protein are adjacent packing neighbors, and the effects of the combined mutations may be described as comprising the additive effects of the constituent point mutations. The Cys83→Thr and Cys117→Val mutations do not affect any of the 8 identified cavities in the structure, and the cavity-filling properties of this quadruple mutant are essentially identical to that which is observed for the Leu44→Phe+ Phe132→Trp double mutant. These four mutations within the core region are accommodated with essentially no detectable change in the overall structural backbone. An overlay of the set of the main chain atoms within 5 Å from positions 44, 83, 117 and 132 yields a root-mean-square deviation of 0.23 Å (see FIG. 20B).

Isothermal Equilibrium Denaturation and Differential Scanning Calorimetry:

The isothermal equilibrium data for the mutant proteins, exhibit excellent agreement in each case with a 2-state model. The Trp mutations at positions 44, 85 and 132 exhibit differential effects upon protein stability. Leu44→Trp is destabilizing by 3.4 kJ/mol and Phe85→Trp is essentially neutral, whereas Phe132→Trp stabilizes the protein by −1.6 kJ/mol (see table in FIG. 14). Both the Val31→Ile (4.0 kJ/mol) and Cys117→Ile (1.5 kJ/mol) mutations destabilize the protein. The combined double mutant of Leu44→Phe+ Phe132→Trp stabilize the protein by −3.9 kJ/mol and therefore yields essentially additive effects upon stability in comparison to the constituent point mutations.

As reported, the Cys117→Val mutation, which effectively removes this buried free cysteine, is only slightly destabilizing (1.2 kJ/mol), while the Cys83→Thr mutation substantially (5.2 kJ/mol) destabilizes the protein. The combined Cys83→Thr+Cys117→Val double mutant, which eliminates two of the three buried free cysteine residues in the protein, destabilizes by 6.1 kJ/mol (see table in FIG. 14). This is essentially an additive effect of the constituent point mutations. Notably, combining the destabilizing Cys83→Thr+Cys117→Val double mutant with the stabilizing Leu44→Phe+Phe132→Trp double mutant yields a quadruple mutant whose stability is indistinguishable from that of the wild-type protein (see table in FIG. 14). Thus, in the Leu44→Phe+Cys83→Thr+Cys117→Val+Phe132→Trp quadruple mutant, two of the three buried free-cysteines are eliminated while wild-type-equivalent stability is effectively maintained. The Lys12→Val+Cys83→Thr+Cys117→Val triple mutant combines the destabilizing double cysteine mutant with a point mutation (Lys12→Val; located in a partially solvent-accessible surface position) that has been shown to stabilize the protein by −7.8 kJ/mol (and fills adjacent cav1). See, e.g., Dubey V. K. (2007), supra. The resulting Lys12→Val+Cys83→Thr+Cys117→Val triple mutant exhibits a stability (−1.9 kJ/mol) that is slightly better than wild-type FGF-1 and is essentially the sum of the individual point mutations. Thus, this combined mutant eliminates two of the three buried free-cysteine residues but has improved stability relative to wild-type FGF-1.

Differential scanning calorimetry data was collected for the Leu44→Trp, Phe85→Trp, and Phe132→Trp point mutations, as well as the Leu44→Phe+Phe132→Trp double mutant (See table in FIG. 15). The ΔΔG values derived from differential scanning calorimetry measurements are in excellent agreement with the isothermal equilibrium denaturation data (See table in FIG. 14). The results show that both ΔH and ΔS increase for the stabilizing mutations, and both decrease for the destabilizing Phe85→Trp. The ΔΔG values for these mutations positively correlate with ΔΔH and negatively correlate with −T*ΔΔS in each case. Thus, the observed changes in stability for these mutations reflect an enthalpy-driven process. The DSC data is consistent with the introduction of favorable van der Waals interactions for the Leu44→Phe and Phe132→Trp mutants, but not the Phe85→Trp mutant. The DSC data also confirm the isothermal equilibrium data in showing that the effects upon melting temperature and ΔG for the Leu44→Phe+ Phe132→Trp double mutant are essentially additive with respect to the constitutive point mutations.

Mitogenic Activity and Functional Half-Life in Unconditioned Medium:

The mitogenic response or activity of NIH 3T3 cells with wild-type, Cys117→Val (C117V), Cys83→Thr+ Cys117→Val (C83T/C117V), Leu44→Phe+Cys83→Thr+ Cys117→Val+Phe132→Trp (C83T/C117V/L44F/F132W), and Lys12→Val+Cys83→Thr+Cys117→Val (C83T/C117V/K12V) mutant proteins (in the presence and absence of heparin sulfate) is shown in FIG. 21. Both the wild-type and Cys117→Val mutant proteins exhibit a marked decrease in mitogenic activity in the absence of 10 U/ml exogenously added heparin (see table in FIG. 16). However, the Cys83→Thr+Cys117→Val, Leu44→Phe+Cys83→Thr+ Cys117→Val+Phe132→Trp, and Lys12→Val+ Cys83→Thr+Cys117→Val mutant proteins exhibit substantial mitogenic potency, even in the absence of exogenously added heparin.

Furthermore, the mitogenic response or activity of wild-type FGF-1 and Ala66→Cys (A66C) mutant FGF-1 protein in both the absence or presence of heparin is shown in FIGS. 22A and 22B. The $EC_{50}$ value of wild-type FGF-1 in the absence of heparin is 58.4 ng/ml, while the Ala66→Cys mutant exhibits an $EC_{50}$ value of 5.43 ng/ml. Thus, the Ala66→Cys mutant exhibits ~10-fold increase in mitogenic activity relative to wild-type FGF-1 in the absence of added heparin. In the presence of heparin the wild-type FGF-1 and Ala66→Cys mutant are essentially indistinguishable, with $EC_{50}$ values of 0.48 ng/ml and 0.36 ng/ml, respectively (see table in FIG. 17). These results show that the Ala66→Cys mutant has enhanced mitogenic activity in the absence of added heparin.

The mitogenic half-life of wild-type, Cys117→Val, Cys83→Thr+Cys117→Val, Leu44→Phe+Cys83→Thr+ Cys117→Val+Phe132→Trp, and Lys12→Val+ Cys83→Thr+Cys117→Val mutant FGF-1 proteins in response to pre-incubation in unconditioned DMEM is shown in FIG. 23. The wild-type protein displays a pre-incubation half-life of 1.0 hour. However, with the inclusion of the Cys117→Val mutation the half-life increases to 9.4 hours. Subsequent addition of the Cys83→Thr mutation increases the pre-incubation half-life to 14.9 hours. When this Cys117→Val+Cys83→Thr double mutant is modified further by the addition of either the stabilizing Leu44→Phe+ Phe132→Trp double mutant or the stabilizing Lys12→Val point mutant, the half-life increases further to 42.6 and 40.4 hours, respectively (see table in FIG. 16).

Furthermore, the residual activity of wild-type FGF-1 and the Ala66→Cys (A66C) mutant as a function of pre-incubation period in DMEM/0.5% NCS medium at 37° C. is shown in FIG. 24 and FIG. 17. Under these conditions wild-type FGF-1 exhibits a functional half-life of 1.0 hr; however, the Ala66→Cys mutant exhibits ~14-fold increase (yielding a functional half-life of 14.2 hr) (see table in FIG. 17).

Resistance to Thiol Reactivity, Aggregation and Trypsin Proteolysis in TBS:

The wild-type protein, and to a lesser extend the Cys117→Val mutant, exhibited visible precipitation after 24 and 48 hours incubation at 37° C. in TBS. The wild-type protein exhibits a general reduction in total soluble protein as a function of incubation time in TBS (see FIG. 25A). Furthermore, the non-reduced samples indicate the formation of higher-molecular mass forms, consistent with disulfide-linked dimers and trimers, as a function of time. The Cys117→Val mutant (see FIG. 25B) yields a slight improvement in recovery of soluble material as a function of incubation time (see reduced lanes in FIG. 25B), although the presence of higher-mass disulfide-linked forms is evident (see non-reduced lanes in FIG. 25B). The Cys83→Thr+ Cys117→Val double mutant improves upon both the recovery of soluble protein (see reduced lanes in FIG. 25C) and the majority of the soluble protein is present as a monomeric form (see non-reduced lanes in FIG. 25C). This mutant has a single Cys residue at position 66. Thus, the higher-mass form visible under non-reducing conditions is consistent with formation of an inter-molecular Cys16-Cys16 disulfide bonded dimer (i.e., about 36 kDa). The Leu44→Phe+ Cys83→Thr+Cys117→Val+Phe132→Trp (FIG. 25D) and Lys12→Val+Cys83→Thr+Cys117→Val (FIG. 25E) mutant proteins show improvements in both recovery of soluble material and fraction of monomeric form in comparison to the Cys83→Thr+Cys17→Val mutant, with the Lys12→Val+ Cys83→Thr+Cys117→Val mutant yielding the greatest recovery of soluble monomeric protein after incubation.

The resistance to trypsin digestion for the wild-type, Cys117→Val, Cys83→Thr+Cys117→Val, Leu44→Phe+ Cys83→Thr+Cys117→Val+Phe132→Trp, and Lys12→Val+Cys83→Thr+Cys117→Val mutant proteins is shown in FIG. 26. The associated half-life of the intact protein is given in the table in FIG. 16. The Lys12→Val+ Cys83→Thr+Cys117→Val exhibits the greatest resistance to trypsin digestion (with a half-life of 19.1 min under the conditions tested), while the Cys117→Val mutant exhibits the greatest susceptibility to trypsin digestion (with a half-life of 9.1 min).

Example 2 Discussion

The in vitro characterization of the functional half-life of the FGF-1 protein demonstrates an interactive relationship between the reactivity of buried free cysteine residues and the thermodynamic stability of the protein. Core packing mutations are shown to increase thermostability and counteract the minor destabilization associated with removal of free cysteine residues, while elimination of the free cysteines avoids irreversible formation of disulfide bonds that are incompatible with the native structure of FGF-1. Thus, stabilizing core packing mutations may be combined with mutations that eliminate buried free cysteines to produce substantial gains in functional half-life without heparin, while maintaining wild-type surface features and solvent structure that avoid potential immunogenicity.

The previously reported X-ray structure of wild-type FGF-1 shows that the three free cysteines (at positions 16, 83, and 117) are each buried within the protein interior and are 11-19 Å distal to each other. See, e.g., Blaber, M. (1996), supra. Formation of inter- or intra-molecular disulfide bonds therefore requires substantial structural rearrangement (as would occur with protein unfolding), and is incompatible with native protein structure and function. The half-life study of wild-type FGF-1 in unconditioned DMEM indicates a functional half-life of about 1.0 hour. Although the related incubation studies in TBS are not directly comparable on the same time scale (due principally to concentration differences utilized in these assays) the TBS study identifies a physical basis for the observed loss of function (i.e., the incubation study of wild-type FGF-1 in TBS demonstrates loss of soluble monomeric protein as a function of time due to irreversible aggregation). Furthermore, the soluble material that is recovered shows the formation of higher-mass disulfide adducts.

The Cys117→Val mutant eliminates one of three buried free cysteine residues in FGF-1 and is associated with an increase in functional half-life in unconditioned DMEM from 1.0 to 9.4 hours. This point mutant is essentially neutral with regard to its effects upon thermostability. Thus, the observed increase in functional half-life is likely due exclusively to the elimination of a buried reactive thiol. The incubation of the Cys117→Val mutant in TBS is associated with a marked reduction in visible aggregation, and the gel assay shows an increase in recovery of soluble protein (although disulfide adducts involving Cys16 and Cys83 are clearly present). (See FIG. 25) Elimination of a second buried reactive thiol at position Cys83, with the Cys83→Thr+Cys117→Val double mutant, increases the half-life in unconditioned DMEM to 14.9 hr. The TBS incubation of this mutant shows improved recovery of soluble monomeric protein, and the disulfide adduct is now limited to inter-molecular dimer formation involving the remaining thiol at position Cys16. The Cys83→Thr+ Cys117→Val mutant is destabilizing compared to the Cys117→Val mutant, and so the observed increase in half-life of this double mutant is due to the elimination of the second buried reactive thiol and not due to an increase in thermostability. The Cys117→Val and Cys83→Thr+ Cys117→Val mutants show that the elimination of buried free cysteines within the structure is associated with a substantial and combinatorial increase in the in vitro half-life. Accessibility of buried thiols requires unfolding of the protein, and disulfide bond formation is an irreversible pathway from the denatured state. Such pathways shift the folding equilibrium (via Le Chatelier's principle) in the direction of the denatured state.

Comparing the Cys83→Thr+Cys117→Val, Leu44→Phe+Cys83→Thr+Cys117→Val+Phe132→Val and Lys12→Val+Cys83→Thr+Cys117→Val mutant proteins provides an opportunity to evaluate the effects of increasing thermostability, respectively, under conditions where the number and type of buried reactive thiols is held constant (in this case, to the single remaining Cys16 residue). In comparison to the Cys83→Thr+Cys117→Val mutant, the Leu44→Phe+Cys83→Thr+Cys117→Val+Phe132→Val mutant stabilizes the protein by −6.5 kJ/mol, and the Lys12→Val+Cys83→Thr+Cys117→Val mutant stabilizes the protein by −7.8 kJ/mol. Both of these mutants increase the functional half-life in unconditioned DMEM in comparison to the Cys83→Thr+Cys117→Val mutant by a factor of three (from 14.9 hr to 42.6 and 40.4 hr, respectively). This increase in functional half-life is therefore due exclusively to the increase in thermostability, as no changes to buried thiols have been made. The incubation in TBS shows that this increase in thermostability is associated with a reduction in the formation of disulfide-bonded dimer and a corresponding increase in the soluble monomeric form of the protein (FIGS. 22C through 22E). These results are consistent with the hypothesis that denaturation is necessary for buried free cysteines to become available for disulfide bond formation, and increasing protein stability shifts the folding equilibrium towards the native state, thereby limiting the availability of the buried thiol for reactivity.

The addition of heparin to FGF-1 is known to stabilize the protein and increase its melting temperature by about 20° C. See, e.g., Copeland, R. A. et al. (1991), supra. The addition of heparin to wild-type FGF-1 increases its potency in the 3T3 fibroblast mitogenic assay by almost two orders of magnitude (see table in FIG. 16). However, the results show that a similar enhancement in mitogenic activity is achieved in the absence of added heparin for those FGF-1 mutant proteins that include the Cys83→Thr+Cys117→Val double mutation (see FIG. 21). Furthermore, the Cys117→Val mutation alone provides some enhancement in activity in the absence of added heparin (although not to the extent observed for the double Cys mutants or in comparison to wild-type FGF-1 in the presence of heparin). These results indicate that one of the major effects of the heparin-induced stabilization of FGF-1 is to effectively curtail buried thiol reactivity. Point mutations that substantially stabilize the FGF-1 protein have been shown to increase the mitogenic potency in the absence of added heparin (see, e.g., Dubey, V. K. et al. (2007), supra), and the present results suggest that this stability effect upon mitogenic activity is due principally to the abolishment of buried thiol reactivity.

Wild-type FGF-1 exhibits relatively poor thermal stability and contains three free cysteines within the solvent-excluded core region. The present results demonstrate a functional connection between buried free cysteines and thermostability, such that mutations affecting these properties may modulate the functional half-life. The results show that in spite of potentially destabilizing effects, if buried thiols are eliminated by mutation, a significant increase in functional half-life is possible. Conversely, if the protein realizes a substantial gain in thermostability (i.e., due to mutation), the contribution of buried free cysteines in limiting functional half-life would be significantly diminished. Thus, the combination of relatively low thermal stability and buried free cysteine residues in FGF-1 may represent co-evolved properties that cooperate to effectively regulate functional half-life. On the other hand, these two properties might be intentionally manipulated in protein design efforts to achieve a desired target functional half-life. Mutants with enhanced stability and functional half-life offer potential advantages over the wild-type protein. However, there may be therapeutic applications where rapid clearance of the applied FGF protein is desirable. In this case, mutants forms with reduced half-life can potentially be designed by lowering thermostability and introducing additional buried cysteine residues.

Other properties, including susceptibility to proteolytic degradation, may contribute to the observed 3T3 fibroblast mitogenic half-life of the mutant FGF-1 proteins. For the set of mutants tested, the resistance to trypsin digestion directly correlates with the thermodynamic stability of the protein (see tables in FIGS. 14 and 16). Thus, in addition to limiting the accessibility of buried reactive thiols, increasing thermostability protects the FGF-1 protein from loss of function due to proteolytic degradation. If mutation of buried free cysteines lowers thermodynamic stability, it can increase susceptibility to proteolytic degradation and thereby contribute to a decrease in functional half-life. In the case of Cys83 in FGF-1, a detailed X-ray structure and thermodynamic study shows that the local structural environment is optimized to accept a cysteine at this position, and substitution by other residues results in significant destabilization (with the least-disruptive mutation being Cys83→Thr). Thus, combining mutations that eliminate buried free cysteine residues with mutations that increase thermostability may offset instability associated with cysteine mutations and may have a synergistic effect upon functional half-life.

The manipulation of thermostability and/or buried free thiols is of particular interest in the design of "second generation" protein biopharmaceuticals. However, the immunogenic potential as a consequence of mutational change is an important consideration. Substitution of buried free cysteines may be constructed with stabilizing secondary mutations, such that these mutations are solvent inaccessible and accommodated with minimal perturbation of the overall wild-type structure. Mutations in FGF-1 may be designed to eliminate buried thiols and/or contribute to protein stability, but leave the protein's surface features, including the solvent structure, indistinguishable from that of wild-type. In attempting to achieve this goal, mutations to fill core-packing defects may be made to thereby stabilize the protein without introducing changes to the surface structure. In evaluating a total of six core mutations, two are shown to be successful (i.e., Phe132→Trp, and a previously described Leu44→Phe mutation), and one "broke even" (i.e., Phe85→Trp) (see table in FIG. 14). The DSC data indicates that a net gain in van der Waals interactions is realized by the successful subset of aromatic side chain mutations (i.e., Phe132→Trp and Leu44→Phe), but that the others (e.g., Phe85→Trp) are accommodated with an actual loss of favorable van der Waals interactions. Thus, the disruption of local van der Waals interactions to accommodate the larger aromatic mutant side chains may offset any gain from the additional buried area.

The two successful core mutations are combined to provide about 4 kJ/mol of increased thermostability that may be used to offset an equivalent decrease incurred by the elimination of two of the three buried free cysteines (Cys83→Thr, Cys117→Val). Thus, the elimination of two buried thiols may be accomplished while maintaining overall thermostability, resistance to proteolysis, and most notably, achieving an approximately 40× increase in functional half-life that eliminates the need for exogenously added heparin to achieve full mitogenic potency. An overlay of the main chain atoms of this quadruple mutant with those of wild-type FGF-1 from the X-ray structures yields a root-mean-square deviation of 0.25 Å, essentially identical to a similar overlay involving only those positions within 5.0 Å of the sites of mutation, and equivalent to the estimated error of the mutant X-ray data set. Furthermore, a total of 52 conserved solvent molecules distributed over the surface of the wild-type and quadruple mutant proteins are in essentially identical positions when comparing the two structures (FIG. 27). Thus, the designed mutations within the solvent-excluded region of the protein are incorporated without perturbing the wild-type surface features, including solvent structure, and consequently, the immunogenic potential of this mutant may be correspondingly minimized. This successful design principle may be applicable to a broad range of globular proteins that contain a buried free cysteine residue and core-packing defects.

FIG. 28 shows the mutant protein C83T/C117V/L44F/F132W (SEQ ID NO: 13).

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

That which is claimed is:

1. A method of treating a wound and/or tissue damage associated with an ischemic condition or disease, the method comprising improving blood flow, angiogenesis, and/or vascularization to the wound and/or tissue damage by triggering cell growth at a site of the wound and/or tissue damage of a patient in need thereof by administering to the patient a therapeutically effective amount of a composition comprising a mutant fibroblast growth factor (FGF) protein having a polypeptide sequence comprising SEQ ID NO: 13.

2. The method of claim 1, wherein the wound and/or tissue damage is due to at least one of a stroke and myocardial infarction.

3. The method of claim 1, wherein the composition is administered locally within the patient's body.

4. The method of claim 1, wherein the therapeutically effective amount of the composition is an amount therapeutically effective to increase angiogenesis in the patient's body.

* * * * *